US011173212B2

(12) United States Patent
Britto et al.

(10) Patent No.: US 11,173,212 B2
(45) Date of Patent: Nov. 16, 2021

(54) SUPRAMOLECULAR PROTEIN ASSEMBLIES WITH ADVANCED FUNCTIONS AND SYNTHESIS THEREOF

(71) Applicant: INDIAN INSTITUTE OF SCIENCE EDUCATION AND RESEARCH, Pune (IN)

(72) Inventors: Sandanaraj Selvaraj Britto, Pune (IN); Pavankumar Janardhan Bhandari, Pune (IN); Mullapudi Mohan Reddy, Pune (IN)

(73) Assignee: Indian Institute of Science Education and Research, Maharashtra Pune (IN)

( * ) Notice: Subject to any disclaimer, the term of this patent is extended or adjusted under 35 U.S.C. 154(b) by 196 days.

(21) Appl. No.: 16/146,891

(22) Filed: Sep. 28, 2018

(65) Prior Publication Data
US 2019/0134212 A1 May 9, 2019

(30) Foreign Application Priority Data

Sep. 28, 2017 (IN) .............................. 201721034557

(51) Int. Cl.
| | | |
|---|---|---|
| A61K 47/64 | (2017.01) | |
| A61K 38/48 | (2006.01) | |
| A61K 47/54 | (2017.01) | |
| C12N 9/96 | (2006.01) | |
| A61K 41/00 | (2020.01) | |
| A61K 38/00 | (2006.01) | |

(52) U.S. Cl.
CPC .......... *A61K 47/64* (2017.08); *A61K 38/4826* (2013.01); *A61K 41/0042* (2013.01); *A61K 47/54* (2017.08); *C12N 9/96* (2013.01); *C12Y 304/21004* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,531,191 B2 | 5/2009 | Zion et al. | |
| 7,625,764 B2 | 12/2009 | Stayton et al. | |
| 10,188,136 B2 * | 1/2019 | Britto | ........................ A61K 8/66 |
| 2002/0032281 A1 * | 3/2002 | Harris | ................ A61K 47/6903 |
| | | | 525/117 |
| 2010/0189643 A1 | 7/2010 | Chilkoti et al. | |

(Continued)

FOREIGN PATENT DOCUMENTS

WO 2016/143989 A1 9/2016

OTHER PUBLICATIONS

Jonathan K. Dozier and Mark D. Distefano. "Site-Specific PEGylation of Therapeutic Proteins." International Journal of Molecular Sciences, vol. 16, 2015, pp. 25831-25864. (Year: 2015).*

(Continued)

*Primary Examiner* — Isaac Shomer
(74) *Attorney, Agent, or Firm* — Kramer Amado

(57) ABSTRACT

The present invention discloses stimuli-sensitive protein conjugate which can make supramolecular protein assemblies and methods for using the same. The present invention provides simple and rational process for construction of said stimuli-sensitive spherical protein assemblies through supramolecular chemical strategy.

12 Claims, 17 Drawing Sheets

(1A')

(56) References Cited

U.S. PATENT DOCUMENTS

2013/0079277 A1    3/2013    Chilkoti
2017/0231260 A1*    8/2017    Britto ............. C12Y 304/21001
                                                          424/1.69

OTHER PUBLICATIONS

Zhaoxing Liu, Lei Wang, Chunyan Bao, Xinxin Li, Lei Cao, Kerong Dai, and Linyong Zhu. "Cross-Linked PEG via Degradable Phosphate Ester Bond: Synthesis, Water-Swelling, and Application as Drug Carrier." Biomacromolecules, 2011, vol. 12, 2389-2395. (Year: 2011).*

M. V. Badiger, V. S. Kadam, A. K. Lele, P. P. Wadgaonkar, D. Hourdet. "Synthesis and Characterization of Novel Hydrophobically End-Capped Poly(ethylene oxide)s [PEOs]." Macromolecular Symposia, vol. 241, 2006, pp. 9-13. (Year: 2006).*

Dmitry Shamshurin, Oleg V. Krokhin, David Levin, Richard Sparling, John A.Wilkins. "In situ activity-based protein profiling of serine hydrolases in E. coli." EuPA Open Proteomics, vol. 4, 2014, pp. 18-24. (Year: 2014).*

Chaoliang He, Xiuli Zhuang, Zhaohui Tang, Huayu Tian, and Xuesi Chen. "Stimuli-Sensitive Synthetic Polypeptide-Based Materials for Drug and Gene Delivery." Advanced Healthcare Materials, vol. 1, 2012, pp. 48-78. (Year: 2012).*

Robert J. Robson and Edward A. Dennis. "The Size, Shape, and Hydration of Nonionic Surfactant Micelles. Triton X-100." The Journal of Physical Chemistry, vol. 81, No. 11, 1977, pp. 1075-1078. (Year: 1977).*

Matthew R. Deher, et al. "Temperature Triggered Self-Assembly of Polypeptides into Multivalent Spherical Micelles", J. Am. Chem. Soc., 130, pp. 687-694. (2008).

Jonathan R. McDaniel, et al. "Noncanonical Self-Assembly of Highly Asymmetric Genetically Encoded Polypeptide Amphiphiles into Cylindrical Micelles", Nano Lett., 14, pp. 6590-6598. (2014).

Mauri A. Kostianinen, et al. "Self-assembly and optically triggered disassembly of hierarchical dendron-virus complexes", Nature Chemistry, vol. 2, pp. 394-399. (May 2010).

J. Andrew Mackay, et al. "Self-assembling chimeric polypeptide-doxorubicin conjugate nanoparticles that abolish tumours after a single injection", Nature Materials, vol. 8, pp. 993-999. (Dec. 2009).

Carla S. Thomas, et al. "Solid-State Nanostructured Materials from Self-Assembly of a Globular Protein-Polymer Diblock Copolymer", ACSNANO, vol. 5, No. 7, pp. 5697-5707. (2011).

* cited by examiner

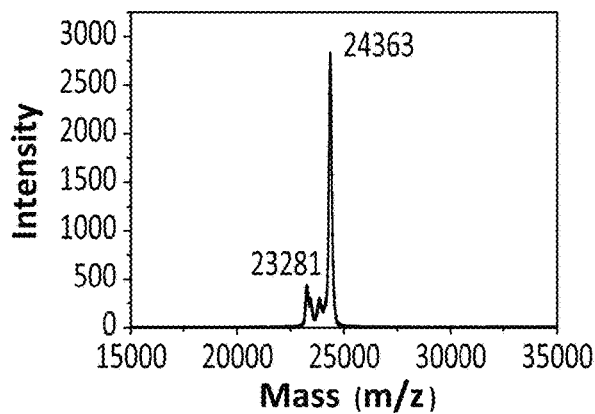
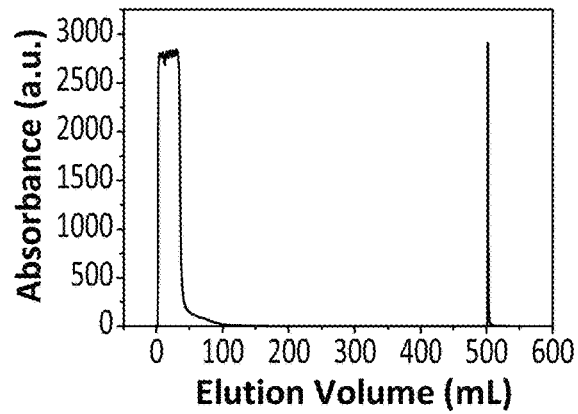
FIG. 7A
FIG. 7B
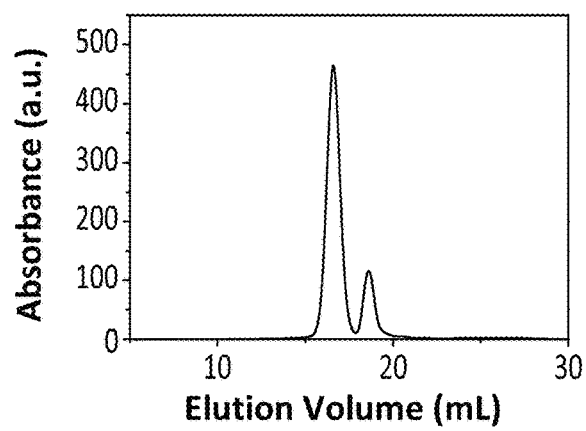
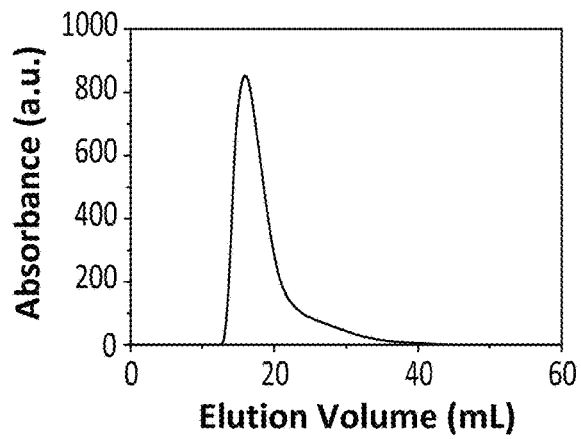
FIG. 7C
FIG. 7D
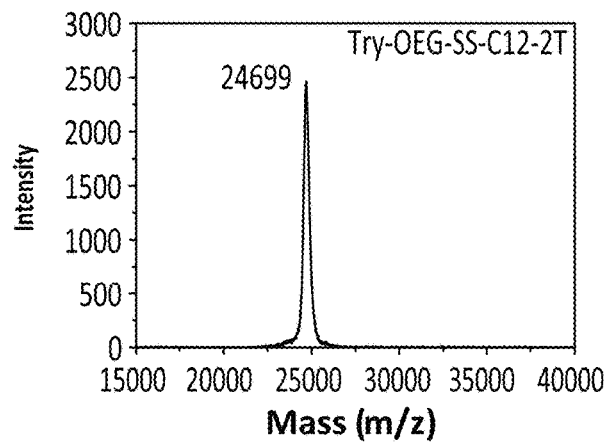
FIG. 7E (I)

(IA')

(IA'''')

SUPRAMOLECULAR PROTEIN ASSEMBLIES WITH ADVANCED FUNCTIONS AND SYNTHESIS THEREOF

TECHNICAL FIELD

The present invention relates to stimuli-sensitive protein conjugate which can make supra molecular protein assemblies and methods for using the same. The present invention provides simple and rational process for construction of said stimuli-sensitive spherical protein assemblies through supra molecular chemical strategy.

BACKGROUND AND PRIOR ART

Natural protein complexes are evolved to perform advanced functions in vivo. This is achieved through several irreversible post-translational modifications of protein complexes, thus converting static structure into dynamic one. Protein engineering using chemical strategies offers excellent possibilities to build protein super structures capable of performing advanced functions.

In the past several years there has been a spurt of interest in the development of dual and multi stimuli-sensitive synthetic protein assemblies for various applications. There is ample literature available on the stimuli-sensitive synthetic protein assemblies.

The article titled 'Noncanonical Self-Assembly of Highly Asymmetric Genetically Encoded Polypeptide Amphiphiles into Cylindrical Micelles' by Jonathan R. McDaniel et. al published in Nano Letters, 2014, 14, 6590-6598 discloses simple approach to driving the spontaneous self-assembly of high molecular weight Elastin-like polypeptides (ELPs) into nanostructures by genetically fusing a short 1.5 kDa (XGy)z assembly domain to one end of the ELP. The highly asymmetric polypeptides self-assemble into cylindrical micelles whose length can be tuned by the sequence of the morphogenic tag.

Thermally responsive elastin-like polypeptides (ELPs) in a linear AB diblock architecture with an N-terminal peptide ligand that self-assemble into spherical micelles when heated slightly above body temperature is disclosed in the article 'Temperature Triggered Self-Assembly of Polypeptides into Multivalent Spherical Micelles' by Matthew R. Dreher et. al published in J. AM. CHEM. SOC. 2008, 130, 687-694.

The article titled 'Self-assembly and optically triggered disassembly of hierarchical dendron-virus complexes' by Mauri A. Kostiainen et. al published in Nature Chemistry, VOL 2, MAY 2010 reports the assembling of virus particles into well-defined micrometre-sized objectsusing photosensitive dendrons that bind on the virus surface through multivalent interactions. The viruses are released by controlled decomposition of the complex by short optical stimuli. It is further disclosed in said article that assembling and disassembling can be also applied to other functional protein cages such as magneto ferritin.

Synthesis of protein-polymer diblock copolymers composed of mCherryS131C and PNIPAM and self-assembling in to nano structured materials induced by solvent evaporation is demonstrated in 'Solid-State Nanostructured Materials from Self-Assembly of a Globular Protein Polymer Diblock Copolymer' by Carla S. Thomas et. al published in ACS Nano, vol. 5, no. 7, 5697-5707.

In the article 'Self-assembling chimeric polypeptide-doxorubicin conjugate nanoparticles that abolish tumours after a single injection' by J. Andrew MacKay et. al in Nature Materials, VOL 8, December 2009 strategies are disclosed to self-assemble biocompatible materials into nanoscale, drug-loaded packages with improved therapeutic efficacy for use in nano medicine. Accordingly, artificial recombinant chimeric polypeptides (CPs) that spontaneously self-assemble into sub-100-nm-sized, near-mono disperse nanoparticles on conjugation of diverse hydrophobic molecules, including chemotherapeutics are provided. The CPs consist of two segments, a hydrophilic, biodegradable elastin-like polypeptide (ELP) and a short segment for the attachment of drugs including a cancer chemotherapeutic—doxorubicin (Dox)—through a pH-labile linker.

U.S. Pat. No. 7,531,191 disclose a method of delivering a therapeutic agent by providing a cross-linked polymer encapsulating the therapeutic agent to a site in a patient. The degradation rate of the cross-linked polymer is correlated with a local concentration of an indicator, and the therapeutic agent is released as the cross-linkedpolymer degrades.

U.S. Pat. No. 7,625,764 reports conjugates that include polymers that are reversibly self-associative in response to a stimulus and methods for using the conjugates.

US2010/0189643 describes a conjugate compound which comprises (a) an active compound; (b) an affinity binding agent; and (c) a block copolymer, said block copolymer consisting of: (i) a first elastin-like polypeptide having a first transition temperature and (ii) a second elastin-like polypeptide having a second transition temperature which is greater than said first transition temperature.

US2013217621 disclose a supramolecular insulin assembly and supramolecular exendin-4 assembly, useful as a protein therapeutic agent for the treatment of metabolic disorders particularly diabetes. The supramolecular assemblies disclosed in US'621 consist of insoluble and aggregated oligomers of protein.

WO2016143989 discloses a method of producing a protein supramolecular assembly comprising the steps of: (a) (i) providing a first splice fragment comprising a β-strand 1-10 of a green fluorescent protein (GFP) (ii) a second split fragment comprising a beta strand 11 of GFP bound to the end of said first split fragment, a plurality of assembly monomers; and (b) self-assembling the plurality of assembly monomers to produce a protein supramolecular assembly.

While the incorporation of unnatural amino acid onto protein is known in the art, hitherto there are no reports on use of unnatural amino acids for construction of synthetic protein complexes through bottom-up approach. The genetic engineering approaches which include both computational and rational design methods though are the emerging methods for building protein super-structures with high accuracy, they are however engineering-intensive. These methods are also limited because of high failure rates and sometime yield protein complexes which are intended by design. In addition, most of the reported protein complexes are static structure and only a limited number of building blocks (standard 20 canonical amino acids) can be used for constructing the protein complexes.

Though protein engineering using chemical strategies offers excellent possibilities to build protein super structure capable of performing advanced functions, the reported chemical strategies are not mature enough to yield monodisperse protein complexes that can be characterized through both high and low resolution structural biology tools. Because of these reasons, underlying principle of design rules to make protein complexes through chemical strategy is still elusive.

The present applicant has reported in their early publication US 20170231260 A1 the site-selective modification by attaching small amphiphilic activity-based probe (AABP) (molecular weights ranging from 500 daltons to 1500 daltons) to the active site of a protein. These conjugates are capable of forming static supramolecular protein assemblies in the range of 8-12 nm.

The need therefore remains in the art for construction of spherical protein assemblies, through supramolecular chemical strategy, that can disassemble in irreversible fashion in response to endogenous and exogenous stimuli.

It is the further objective to provide supramolecular protein complexes wherein the size, shape, molecular mass, oligomeric state, surface charge could be easily programmed by molecular design for applications in the area of in vivo diagnostics, targeted drug delivery, biomaterials and synthetic biology.

SUMMARY OF THE INVENTION

In view of the above, the present invention provides chemical strategies to make protein conjugates that can irreversibly disassemble in response to stimuli.

Accordingly, the protein conjugate which can make supramolecular protein assemblies of the present invention comprises; (a) hydrophilic protein; (b) the linker; (c) hydrophobic group and (d) stimuli-sensitive moiety which can be located anywhere in the supramolecular protein assembly; wherein said supramolecular assemblies can irreversibly disassemble in response to exogenous or endogenous stimuli or combination thereof useful for various application like nanocarriers for target drug delivery, in vivo diagnostics, in biomaterials and synthetic biology etc.

The protein complex size, shape, molecular mass, oligomeric state, surface charge can be easily programmed by molecular design of the present invention.

In an aspect, these stimuli-sensitive protein conjugates are synthesized by attaching amphiphilic activity-based probe (AABP) of molecular weight in the range of 1 kDa to 35 kDa (composed of a flurophosphonate (FP) as a reactive group, hydrophilic linker, hydrophobic dendrimer or tails, and stimuli-sensitive group) to the proteins using micelle-assisted protein bioconjugation strategy.

Accordingly, amphiphilic AABPs were solubilized using triton X-100 as a solubilizing agent due to the formation of mixed micelles; where hydrophobic dendrimer or tails are buried in the hydrophobic micellar interior whereas hydrophilic PEG/OEG with the flurophosphonate (FP) group becomes part of hydrophilic portion of a micelle, which is displayed to the bulk solvent. This is followed by addition of protein to the mixed micelle solution and allowed to react.

In another aspect, the present invention provides purification of stimuli-sensitive conjugate from the reaction mixture.

DESCRIPTION OF THE FIGURES

FIG. 7A depicts MALDI-TOF MS spectrum of reaction mixture of trypsin and redox-sensitive probe (9).

FIG. 7B depicts IEX chromatogram showing separation of triton X-100 and protein mixture.

FIG. 7C depicts SEC chromatogram showing separation of protein conjugate (IA''') and native protein.

FIG. 7D depicts Desalting chromatogram of purified protein conjugate (IA''')

FIG. 7E depicts MALDI-TOF MS of purified protein conjugate (IA''')

DETAILED DESCRIPTION OF THE INVENTION

The invention will now be described in its various preferred as well as optional embodiments, so that the various aspects therein will be more clearly understood and appreciated.

Figure 15:
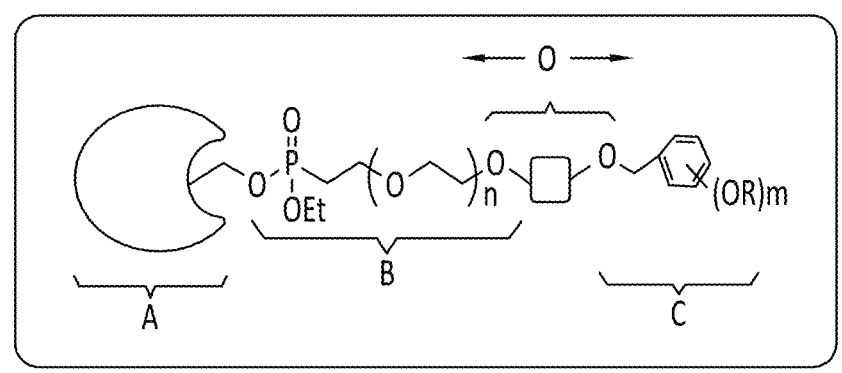
FIG. 15 shows a stimuli-sensitive protein conjugate.

In an embodiment, the present invention relates to stimuli-sensitive protein conjugates which can make supramolecular protein assembly useful for various applications like nano-carriers for drug delivery, in vivo diagnostics, in biomaterials and synthetic biology represented by the general formula (I), shown in FIG. 15.

The compound of general formula (I) comprises;
a hydrophilic protein head group (A) with a length of up to 500 amino acids selected from the group consisting of serine proteases, cysteine proteases, aspartic proteases, metalloproteases such as trypsin, chymotrypsin, subtilisin, elastase, and mixtures thereof; a hydrophilic spacer (B) comprising phosphonate ester of oligoethylene glycol; hydrophobic tails or dendrons (C) wherein the group 'R' represents C4-C20 (un)substituted or substituted straight, branched, cyclic or acyclic aliphatic, aromatic or alkyl or alkoxy phenyl moieties, linear or branched polymers, dendrimers, hydrophobic peptides or proteins; and the stimuli-sensitive moiety (D) that can be located anywhere in the supra molecular protein assembly; 'n' represents the integer 1 to 20; 'm' represents the integer 1 to 4;

wherein said stimuli-sensitive protein conjugate disassembles irreversibly in response to exogenous or endogenous stimuli or combination thereof.

Figure 16:
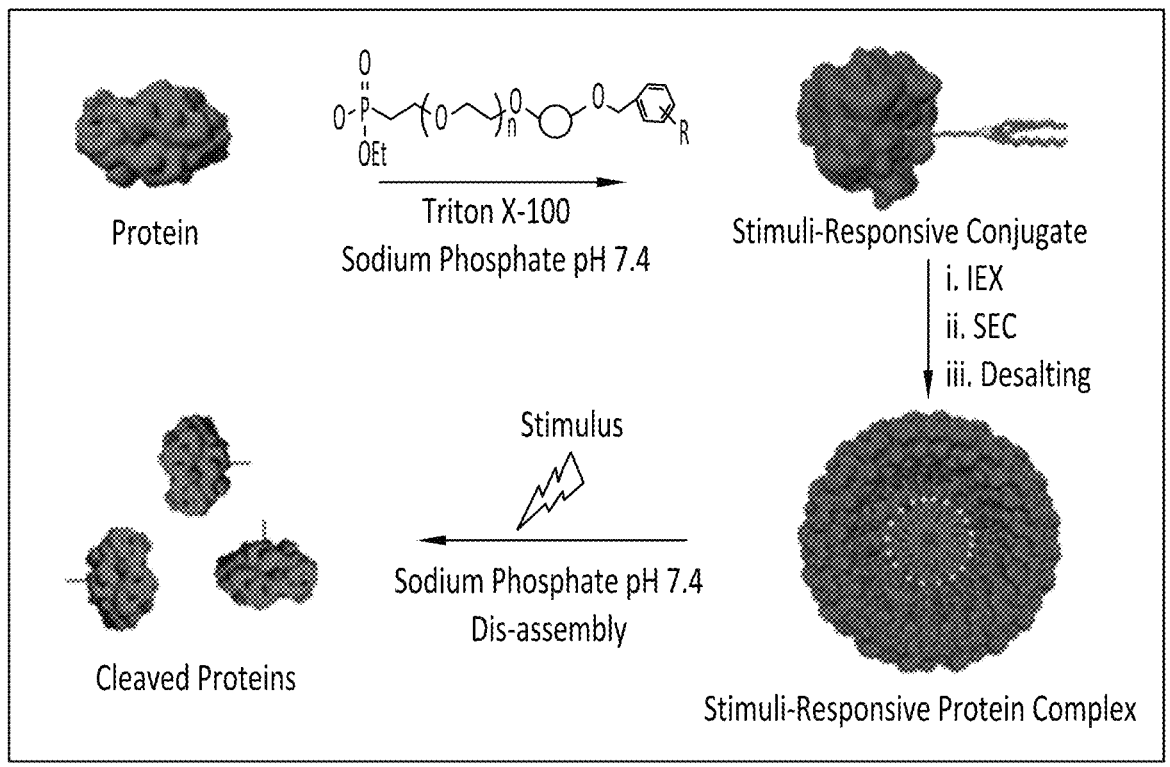
FIG. 16 shows stimuli-sensitive protein conjugates which make supramolecular protein assemblies that disassembles irreversibly on stimulation.

The stimuli-sensitive protein conjugates which can make supramolecular protein assembly that disassembles irreversibly on stimuli are shown in FIG. 16.

The exogenous stimuli include but is not limited to temperature, magnetic field, ultrasound intensity, light or electric pulses; the endogenous stimuli include but is not limited to pH, and enzyme concentration or redox gradients.

In another embodiment, the present invention discloses the process variants for synthesis of stimuli-sensitive protein conjugate of general Formula (I) which can make supramolecular protein assemblies that can disassemble upon stimuli.

In an embodiment, the process for synthesis and purification of stimuli-sensitive protein conjugates comprises;
(i) Homogenizing the stimuli-sensitive amphiphilic activity based probes (AABP) in triton X-100 and sodium phosphate buffer at pH 7.4 followed by addition of the protein solution to the homogenized solution in sodium phosphate buffer at pH 7.4 and allowing it to react;
(ii) Removing triton X-100 from the above mixture using Ion exchange chromatography (IEX) and eluting the native and supramolecular protein assembly using eluting buffer solution;
(iii) Removing the native protein in high salt concentration using size exclusion chromatography followed by desalting and lyophilizing to obtain pure protein conjugate of formula (IA).

Accordingly, the protein modification/conjugation was carried out at the concentration of about 100 μM, which was found to be optimum for MALDI-ToF MS monitoring. Triton X-100 was used to solubilize the said stimuli-sensitive AABPs at concentrations 100 times (20 mM) more than CMC or 2% of total volume of reaction mixture. Proteins were weighed (in the range of 2.3 to 2.9 mg, depending on protein) and 500 μL of 50 mM sodium phosphate pH 7.4 was added and mixed gently to make 200 μM solutions. Then AABPs (1 or 2 equivalents) were weighed followed by addition of about 20 μL of triton X-100 and about 480 μL of 50 mM sodium phosphate pH 7.4 and vortexed for 15 minutes. When the AABP solution becomes clear, the protein solution was added into AABP solution to get about 100 μM (1 mL) protein solutions and allowed to react for 20-24 hrs at 25° C.

The protein conjugate was further purified by three-step purification i.e. IEX, SEC and desalting. The IEX was performed to remove triton X-100 depending on isoelectric point (pI) and surface charges of proteins. The obtained IEX fractions were subjected to SEC immediately to remove the native proteins from the protein conjugates using 50 mM sodium phosphate pH 7.4, 1 M NaCl as buffer. The NaCl was further removed by desalting. The desalted fractions were quickly lyophilized and later dissolved in required buffer when required.

Design of Photo-Sensitive Supramolecular Protein Conjugate

Figure 17:
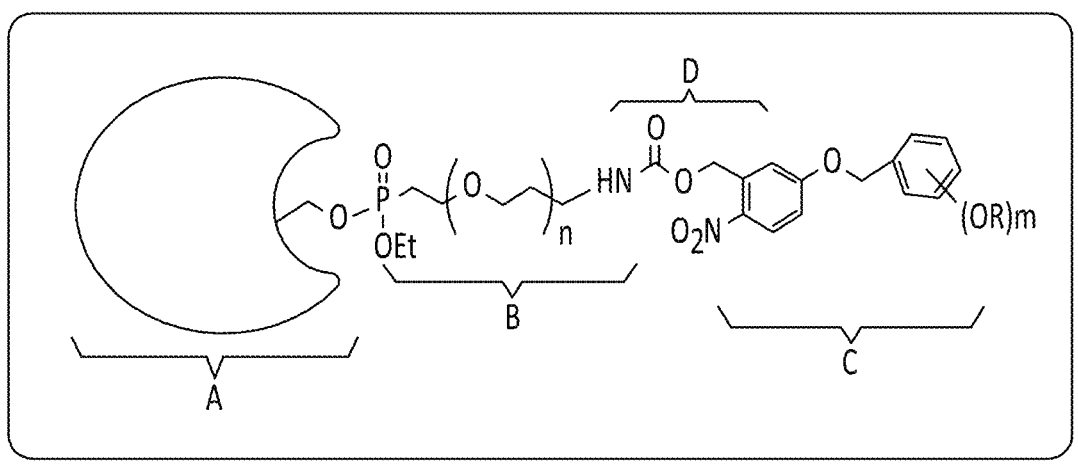
FIGS. 17 and 18 show stimuli-sensitive protein conjugates, which disassemble irreversibly upon photo irradiation.

In another embodiment, the present invention discloses stimuli-sensitive protein conjugate, which can make supramolecular protein assembly, of formula (IA') shown in FIG. 17, which can disassemble irreversibly upon photo irradiation.

a hydrophilic protein head group (A) with a length of up to 500 amino acids selected from the group consisting of serine proteases, cysteine proteases, aspartic proteases, metalloproteases such as trypsin, chymotrypsin, subtilisin, elastase, or mixtures thereof;

a hydrophilic spacer (B) comprising phosphonate ester of oligoethylene glycol;

hydrophobic tails or dendrons (C) wherein 'R' represents C4-C20 (un)substituted or substituted straight, branched, cyclic or acyclic aliphatic, aromatic or alkyl or alkoxy aryl moieties; linear or branched polymers, dendrimers, hydrophobic peptides or proteins;

the photo-sensitive 2-nitrobenzyl moiety (D) located between the hydrophilic portion (B) and the hydrophobic tail (C);

'n' represents the integer 1 to 20;
'm' represents the integer 1 to 4;

wherein said supramolecular protein assembly disassembles irreversibly upon exposure to light/photoirradiation.

Accordingly, the stimuli-sensitive protein conjugate, which can make supramolecular protein assembly, that can disassemble upon photo irradiation comprises Try-OEG-NB-C12-2T of formula (IA') given below;

In an embodiment, the photo-sensitive protein conjugate, which can make supramolecular protein assembly, of Formula (IA"), where PROT is a hydrophilic protein head group, prepared by the process of the present invention have the particle size in the range of 10-1000 nm.

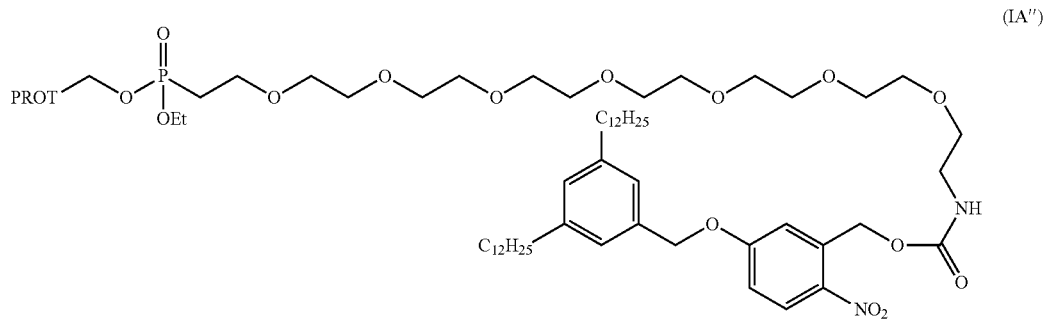

(IA")

Figure 18:
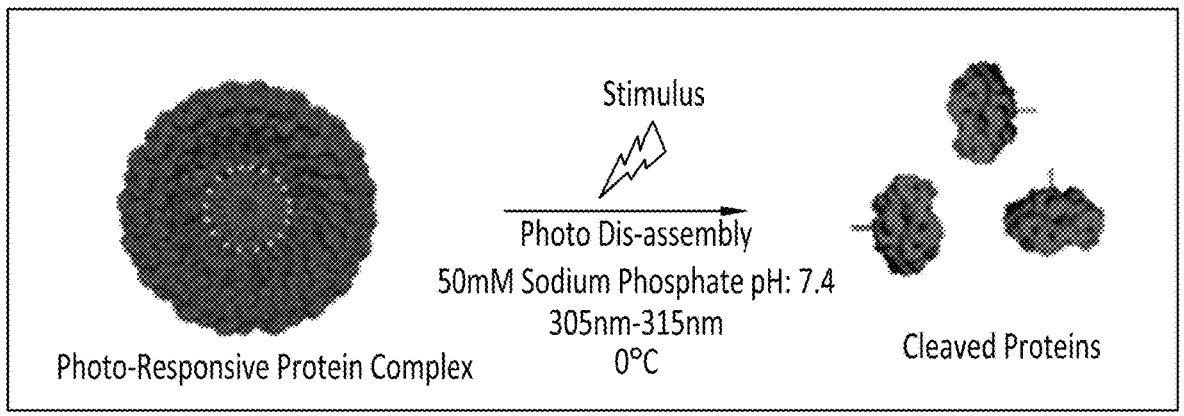

In another embodiment, the present invention relates to the dis-assembly of protein conjugate which make supramolecular protein assembly of formula (IA') having photo-sensitive probe (9), as shown in FIG. 18. Accordingly, the protein conjugate which make supramolecular protein assembly of formula (IA') was dissolved in 50 mM sodium phosphate at pH: 7.4 and temperature was maintained using ice bath during entire reaction, as shown in FIG. 18. The sample was exposed to the ultraviolet rays between 280 nm and 360 nm (peak at 305 nm-315 nm). Samples were withdrawn from time to time using a pipette and analysed using SEC or DLS or MALDI-TOF MS. The supramolecular protein assembly of formula (IA') was observed fully cleaved after about 150 minutes.

Synthesis of Photo-Sensitive Supramolecular Protein Conjugate

In another embodiment, the process for preparing the protein conjugate, which can make supramolecular photo-sensitive protein assembly, of formula (IA') comprises of following steps;

(i) Homogenizing the photo-sensitive AABP probe, 5-((3, 5-bis(dodecyloxy)benzyl)oxy)-2-nitrobenzyl(2-(2-(ethoxyfluoro phosphoryl) ethoxy) ethyl)carbamate (9) in triton X-100 and sodium phosphate buffer at pH 7.4 followed by addition of the protein solution to the homogenized solution in sodium phosphate buffer at pH 7.4 and allowing it to react;

(ii) Removing triton X-100 from the above mixture using Ion exchange chromatography and eluting the native and supramolecular protein assembly using eluting buffer solution;

(iii) Removing the native protein in high salt concentration using size exclusion chromatography followed by desalting and lyophilizing to obtain pure protein conjugate of formula (IA').

The protein in step (i) is selected from hydrophilic protein with a length of up to 500 amino acids, preferably the protein is trypsin. The process is schematically shown below in Scheme 1, where TRYP is trypsin:

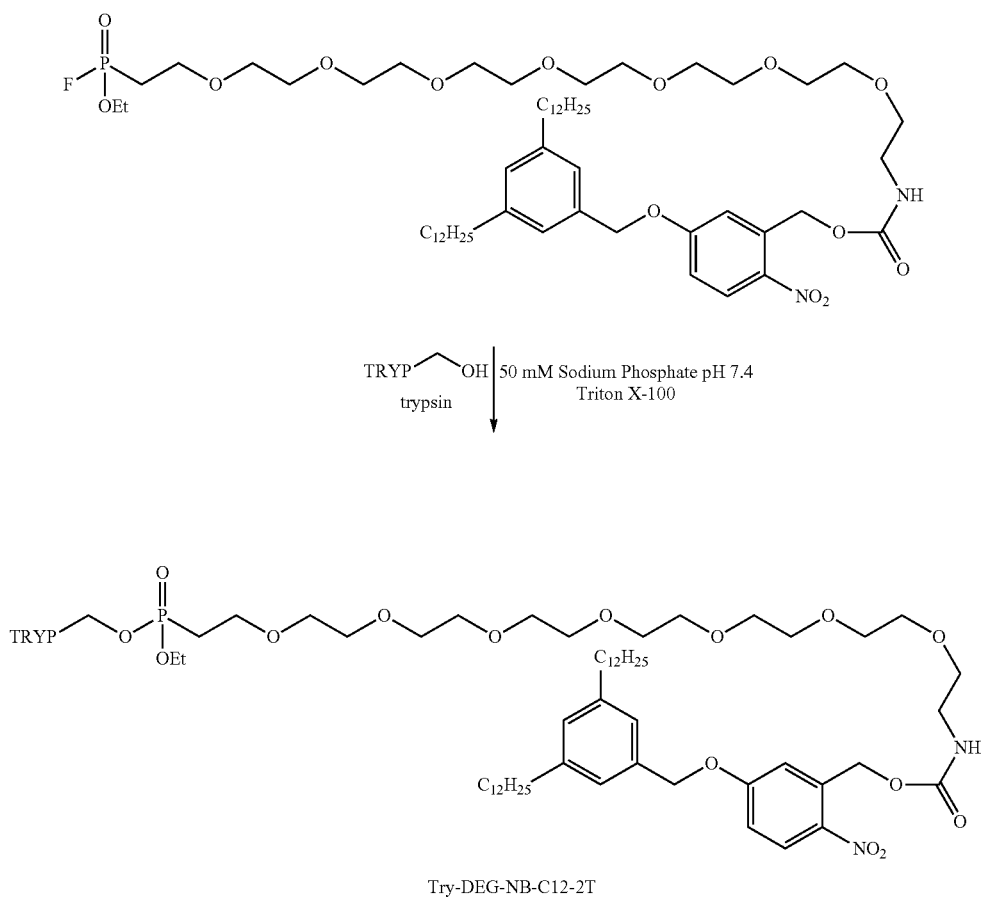

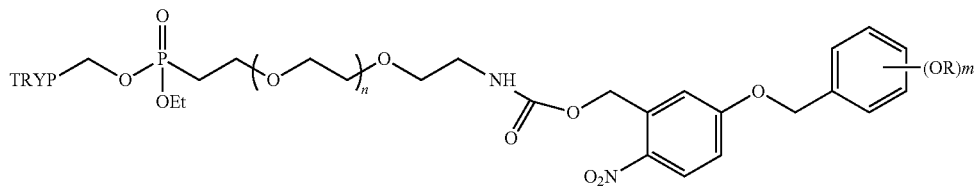

wherein 'R' and 'm' are as defined above.

Synthesis of Photo-Sensitive Probe:

In another embodiment, the process for synthesis of photo-sensitive probe (9) useful for coupling with the protein molecule comprises;
  (i) Reacting 3-hydroxybenzaldehyde with ethyl chloroformate in anhydrous pyridine to obtain ethyl (3-formylphenyl) carbonate (1); nitrating the compound (1) with nitrating agent at 0° C. to obtain nitro compound (2);
  (ii) Hydrolysing nitro compound (2) in presence of base to obtain phenolic compound (3); reacting compound (3) with di-substituted benzyl bromide in presence of base to obtain compound (4);
  (iii) Reducing compound (4) in presence of alkali metal borohydride in solvent mixture to yield alcohol (5); esterifying alcohol (5) with N,N'-disuccinimidyl carbonate in presence of base and solvent to obtain ester (6);
  (iv) Condensing ester (6) with diethyl (2-(2-(2-aminoethoxy)ethoxy)ethyl) phosphonate in presence of base to obtain diphosphonate ester (7);
  (v) Deprotecting diphosphonate ester (7) in presence of LiBr to monophosphonate compound (8) and fluorinating the monophosphonate ester (8) with DAST to obtain photo-sensitive probe (9).

The process is schematically shown in Scheme 2 below:

Scheme 2

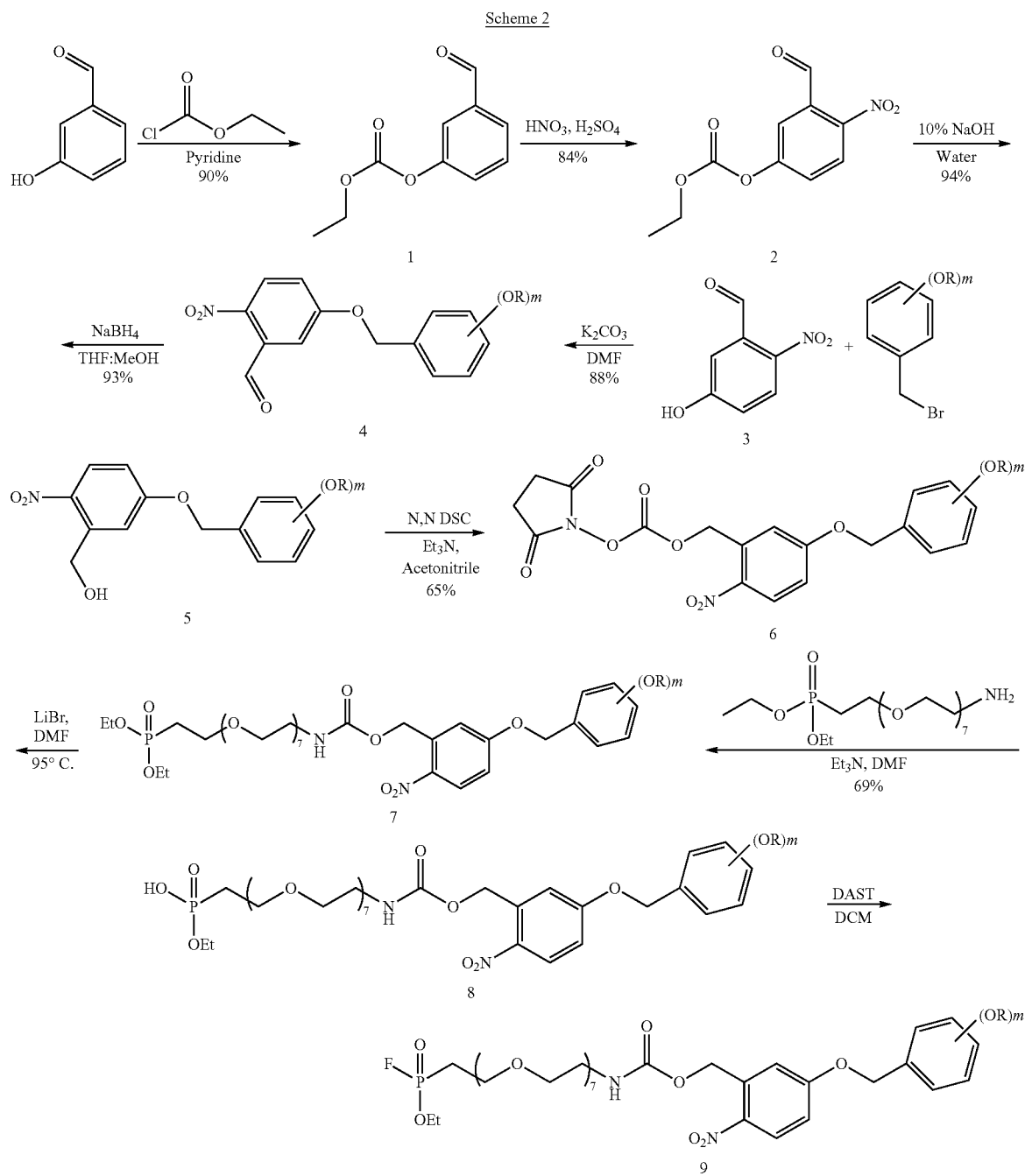

wherein 'R' and 'm' are as defined above.

According to the process, step (i) comprises dissolving 3-hydroxybenzaldehyde in anhydrous pyridine under stirring at 0° C. followed by dropwise addition of ethyl chloroformate under nitrogen atmosphere over a period of about 30 minutes resulting in the precipitation of ethyl (3-formylphenyl) carbonate (1) as white solid. The reaction was allowed to react at room temperature under stirring until clear solution was obtained. The solvent pyridine was concentrated under vacuum, water was added to the residue and the aqueous layer was extracted in organic solvent such as ethers, esters, ketones and the like. The combined organic layers were washed, dried, filtered and concentrated to yield analytically ethyl (3-formylphenyl) carbonate (1).

The compound (1) was nitrated with conc.$H_2SO_4$ and conc.$HNO_3$ at 0° C. under stirring for about 4 hours. Upon completion, the reaction mixture was slowly added to crushed ice. The precipitated, light brown solid was filtered and washed thoroughly with ice cold water during filtration and dried under vacuum to get crude ethyl (3-formyl-4-nitrophenyl) carbonate (2) which was further purified.

Step (ii) comprises alkaline hydrolysis of compound (2) in 10% aqueous NaOH at room temperature followed by neutralization with 4N HCL. The resulting aqueous layer was extracted in organic solvents such as ether, esters, ketones and the like; the combined organic layer was washed, filtered, concentrated and purified to obtain pure 5-hydroxy-2-nitrobenzaldehyde (3).

The 5-hydroxy-2-nitrobenzaldehyde, inorganic base selected from alkali or alkaline metal carbonates, bicarbonates such as sodium carbonate, potassium carbonate, magnesium carbonate, potassium bicarbonate and the like; preferably potassium carbonate and disubstituted benzyl bromide were taken and dissolved in polar aprotic solvent such as THF, ethyl acetate, DMF, MeCN and the like under stirring at RT and allowed to react for about 24 hours. Upon completion of reaction, water was added and extracted in organic solvent. The combined organic layer was dried and evaporated under vacuum, purified to get compound (4).

The step (iii) comprises dissolving compound (4) in polar aprotic solvent such as THF, ethyl acetate, DMF, MeCN and the like. To the mixture was further added polar organic solvent such as lower alcohols, ketones, ethers and the like; preferably lower alcohol. The mixture was cooled to 0° C. and small portions of reducing agent selected from metal borohydride such as $NaBH_4$ was allowed to react for about an hour. Upon completion, reaction was quenched with $Na_2CO_3$ and extracted in organic solvent, the combined organic layer was dried, concentrated and purified to yield alcohol (5).

The compound (5) dissolved in alcohol was esterified using N,N'-Disuccinimidyl carbonate in polar aprotic solvent such as THF, ethyl acetate, DMF, MeCN and the like under stirring. Triethyl amine was then added slowly at RT and allowed to react for about 12 hours until completion of the reaction. Upon completion of reaction, the solvent and triethyl amine was evaporated under vacuum and the obtained residue was purified to yield ester (6).

In condensation step (iv), the ester compound (6) and amine terminated octaethylene glycol spacer (16) (i.e. diethyl (2-(2-(2-aminoethoxy)ethoxy)ethyl) phosphonate) were dissolved in non-polar organic solvent such as polar aprotic solvent such as DMF, MeCN and the like under stirring. Triethyl amine was then added slowly at RT and allowed to react for about 12 hours. Upon completion of reaction, the solvent and triethyl amine was evaporated under vacuum and the obtained residue was extracted using organic solvents. The combined organic layers were dried, concentrated under vacuum and purified to obtain diphosphonate ester (7).

According to step (v), to the mixture of diphosphonate ester (7) and LiBr was added DMF, heated at temperature in the range of 90–95° C. for about 20 hours. Upon completion, water was added and extracted with organic solvents such as ethers, esters, ketones and the like.

The aqueous layer was collected and 2N HCl was added and stirred. The mixture was then extracted in organic solvent and the organic layer was dried, concentrated under vacuum to get crude monophosphonate ester (8) which was further used without purification.

To the stirring solution of monophosphonate ester (8) in organic solvent selected from polar protic or aprotic solvent was added Diethylaminosulfurtrifluoride (DAST) dropwise and the reaction was allowed to react at −78° C. for about 10-15 minutes. Excess of DAST and solvent were evaporated under vacuum. To the residue obtained was added water and stirred to quench any residual DAST. The reaction mixture was extracted in solvent and the combined organic layers were dried, and concentrated under vacuum to obtain photo-sensitive probe (9).

Synthesis of Amine Terminated Octa Ethylene Glycol Spacer (16):

In yet another embodiment, the amine terminated octa ethylene glycol spacer, diethyl (2-(2-(2-aminoethoxy)ethoxy)ethyl)phosphonate (16) was prepared by a process which comprises;

(i) Reacting a mixture of mono benzyl teraethylene glycol (9) and tosylated-tetraethylene glycol (9') in presence of base and solvent to obtain TsO-(OEG) compound (10);
(ii) Refluxing compound (10) with KI in acetone to yield iodo compound (11);
(iii) Refluxing iodo compound (11) and triethylphophite to yield compound (12);
(iv) Reducing compound (12) with suitable reducing agent to obtain hydroxyl compound (13);
(v) Tosylating hydroxyl compound (13) in presence of base and solvent to yield tosylated diphosphonate ester (14);
(vi) Reacting tosylated diphosphonate ester (14) with sodium azide in solvent to obtain azido compound (15);
(vii) Reacting azido compound (15) with Triphenyl phosphine in solvent to yield diethyl (2-(2-(2-aminoethoxy)ethoxy)ethyl)phosphonate(16).

The process is depicted in below in Scheme 3:

Scheme 3

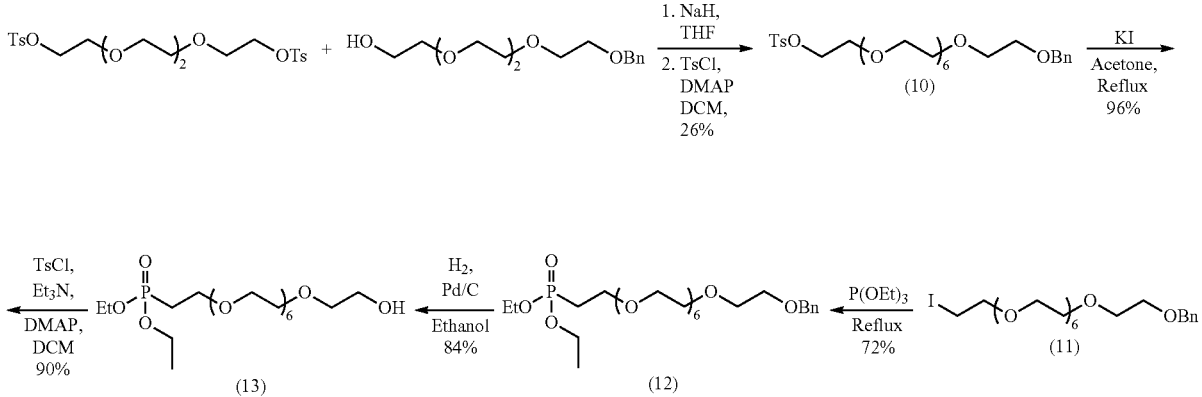

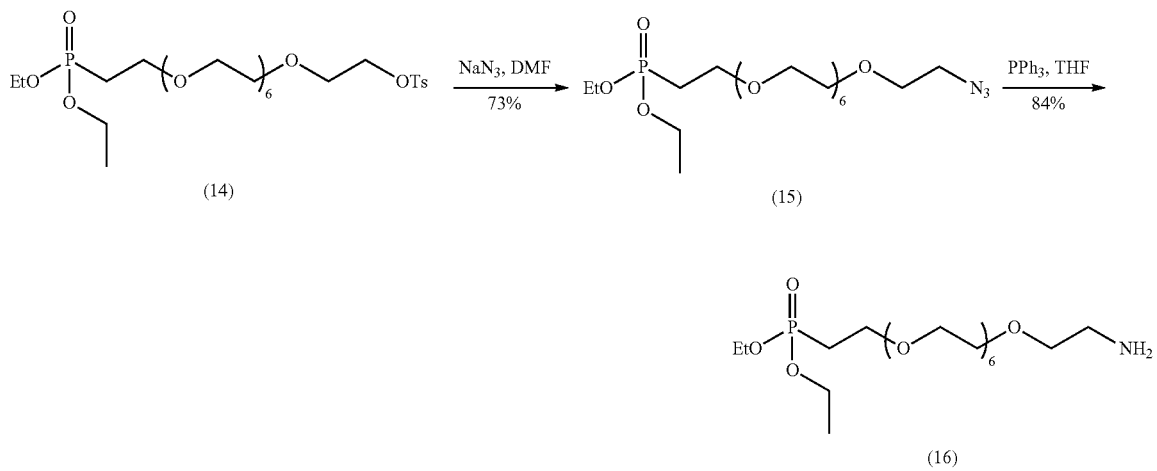

According to the process, in step (i) a mixture of monobenzyl TEG (9) and tosylated tetraethylene glycol (9') was taken and dissolved in THF under stirring. Reaction mixture was cooled to 0° C. and NaH was added in a small portions. Resultant mixture was stirred at RT for 12 hours. Upon completion of reaction, excess of NaH was quenched by dropwise addition of water. Resultant mixture was concentrated under reduced pressure. To the obtained residue, water was added and washed with ethyl acetate thoroughly (about at least for eight times). The aqueous layer was concentrated under reduced pressure and to the obtained residue, fresh ethyl acetate was added and filtered to remove salts. Finally, the resulting ethyl acetate layer was dried and concentrated under reduced pressure to get crude product 2-(2-(2-(benzyloxy)ethoxy)ethoxy)ethyl 4-methylbenzenesulfonate (10) along with TEG contamination. The crude product (10) with TEG, DMAP and tosyl chloride were taken and dissolved in DCM under stirring. Mixture was cooled to 0° C. and triethyl amine was added drop wise. The resultant mixture was then stirred for about 12 hours at RT. Upon completion, reaction was quenched by dropwise addition of water and extracted with DCM.

The combined organic layer was dried and concentrated under reduced pressure to get crude 2-(2-(2-(benzyloxy)ethoxy)ethoxy)ethyl 4-methylbenzenesulfonate (10) which was further purified using silica gel column chromatography.

In step (ii) a mixture of compound (10) and KI were refluxed in polar aprotic solvent for about 18 hours. Upon completion, excess KI was filtered and washed with same solvent. The solvent fractions were collected, evaporated under vacuum to obtain the residue which was further washed with water and extracted in organic solvent. The combined organic layers were washed with aqueous base and concentrated under vacuum, purified to get (2-(2-(2-iodoethoxy)ethoxy)ethoxy)methyl)benzene (11).

The step (iii) comprises refluxing the above compound (11) and triethylphosphite P(OEt)$_3$ for about an hour at temperature in the range of 140–155° C. Upon completion of reaction, the excess P(OEt)$_3$ was removed under vacuum and the reaction mixture was purified to obtain diethyl (2-(2-(2-(benzyloxy)ethoxy)ethoxy)ethyl)phosphonate(12).

In step (iv) the disphosphonate ester (12) was dissolved in alcohol, Pd/C was added and stirred under hydrogen for about 18 hours. Upon completion, the mixture was filtered through celite and washed with alcohol; the filtrate was concentrated under vacuum to get crude mixture (13) and used for next step without purification.

The step (v) comprises dissolving the crude compound (13) of step (v), DMAP and tosyl chloride in non-polar solvent such as hydrocarbons, halogenated hydrocarbons and the like with stirring. The mixture was cooled to 0° C. and triethyl amine was added drop wise. The resultant mixture was stirred for about 12 hours at RT. Upon completion, reaction was quenched by dropwise addition of water and extracted in organic solvent. The combined organic layer were dried, concentrated and purified to yield pure 2-(2-(2-(diethoxyphosphoryl)ethoxy)ethoxy)ethyl 4-methylbenzenesulfonate (14).

In step (vi), to compound (14) was added sodium azide (NaN$_3$) followed by addition of polar aprotic solvent such as THF, DMF, DMSO, acetone and the like and stirred. Upon completion, water was added to the reaction mixture and extracted in solvent. The combined organic layers were dried, concentrated under vacuum and purified to obtain diethyl (2-(2-(2-azidoethoxy)ethoxy)ethyl)phosphonate (15).

The step (vii) comprises adding Triphenyl phosphine to a solution of compound (15) in polar aprotic solvent such as THF, DMF, DMSO, acetone and the like at 0° C. The reaction mixture was allowed to warm to room temperature and stirred for about 18 hours. Water (10-12) drops was added to the reaction mixture and the solution was stirred for about 1 hour. The solvent was concentrated in vacuum. To the obtained residue water was added and washed with organic solvent. The aqueous layer was concentrated under reduced pressure to get crude product which was purified to obtain diethyl (2-(2-(2-aminoethoxy)ethoxy)ethyl)phosphonate(16).

17

Design of pH-Sensitive Supramolecular Protein Conjugate

In yet another embodiment, the present invention discloses protein conjugate, which can make supramolecular protein assembly, of formula (IA") which disassembles irreversibly in response to pH change;

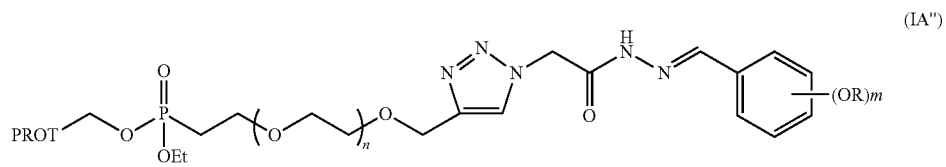
(IA")

comprising;
a hydrophilic protein head group PROT with a length of up to 500 amino acids selected from the group consisting of serine proteases, cysteine proteases, aspartic proteases, metalloproteases such as trypsin, chymotrypsin, subtilisin, elastase, and mixtures thereof;
a hydrophilic spacer comprising phosphonate ester of oligoethylene glycol;
hydrophobic tails or dendrons including a substituted phenyl group, wherein 'R' represents C4-C20 (un)substituted or substituted straight, branched, cyclic or acyclic aliphatic, aromatic or alkyl or alkoxy aryl moieties; linear or branched polymers, dendrimers, hydrophobic peptides or proteins; and
a pH sensitive probe comprising a hydrazine moiety located between the hydrophilic spacer and the hydrophobic tail;
'n' represents the integer 1 to 20;
'm' represents the integer 1 to 4;
wherein said supramolecular protein assembly disassembles irreversibly in response to pH change.

Accordingly, the present invention discloses pH-sensitive supramolecular protein assembly which comprises Try-OEG-NN-C12-2T of the formula (IA").

In another embodiment, the pH-sensitive protein conjugate, which can make supramolecular protein assembly, of Formula (IA") prepared by the process of the present invention have the particle size in the range of 10-1000 nm.

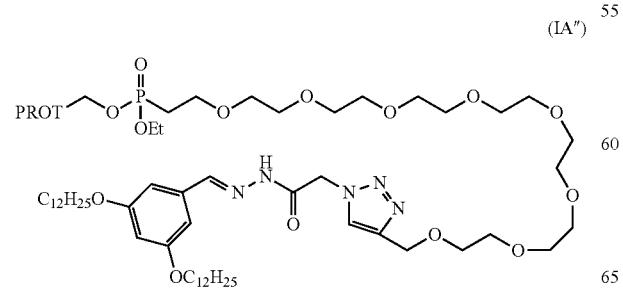
(IA")

18

Figure 19:
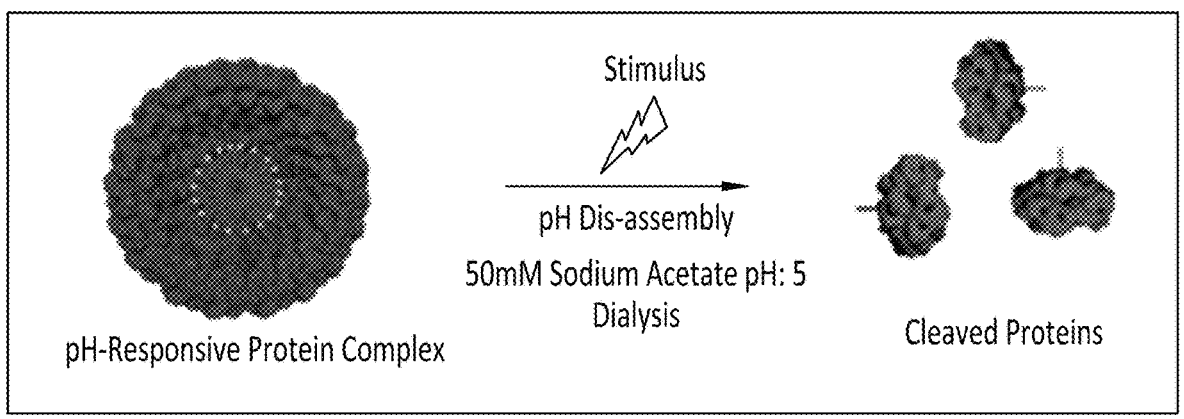
FIG. 19 shows dis-assembly study of protein conjugates when subjected to dialysis based cleavage conditions.

In yet another embodiment, the present invention provides the dis-assembly study of the protein conjugate which make supramolecular protein assembly of Formula (IA") with pH-sensitive probe (17'), as shown in FIG. 19. Accordingly, the supramolecular protein assembly of Formula (IA") was subjected to dialysis based cleavage conditions. The sample was dissolved in milli-Q and taken in 3.5 kDa dialysis bag and dialyzed in 50 mM sodium acetate pH:5 at room temperature or at 35° C. Samples were withdrawn from the dialysis bag from time to time and analysis of the sample was carried out using SEC or MALDI-TOF MS. The supramolecular protein assembly of formula (IA") was observed fully cleaved after 7 days.

Synthesis of pH-Sensitive Supramolecular Protein Conjugate

In an embodiment, the process for preparing the supramolecular pH-sensitive protein assembly of formula (IA") comprises of following steps;

(i) Homogenizing the probe (17') in triton X-100 and sodium phosphate buffer at pH 7.4 followed by addition of the protein solution to the homogenized solution in sodium phosphate buffer at pH 7.4 and allowing it to react;

(ii) Removing triton X-100 from the protein mixture using Ion exchange chromatography and eluting the native and smart protein conjugate using eluting buffer solution;

(iii) Removing the native protein from the conjugate in high salt concentrations using size exclusion chromatography followed by desalting and lyophilizing to obtain pure protein conjugate(IB).

The protein in step (i) is selected from hydrophilic protein with a length of up to 500 amino acids, preferably the protein is trypsin.

The process is depicted below in Scheme 4, where TRYP is trypsin.

Scheme 4

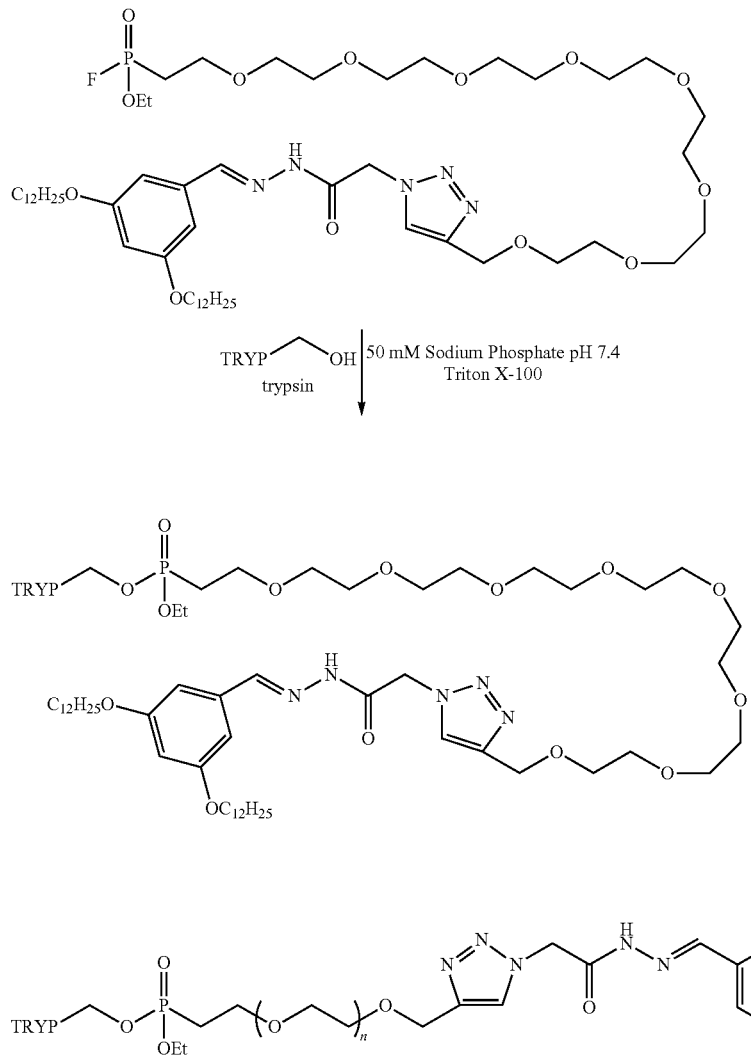

wherein 'R' and 'm' are as defined above

Synthesis of pH-Sensitive Probe:

In an embodiment, The pH sensitive probe (17') was synthesized by the process which comprises;
  (i) Azidation of ethyl bromo acetate in 1:3 water-acetone mixture to yield ethyl 2-azidoacetate followed by reacting with alkyne terminated oligo ethylene glycol spacer (12') using click chemistry to obtain triazol ester compound (13');
  (ii) Reacting above ester (13') with hydrazine in absolute alcohol to obtain triazole phosphate compound (14');
  (iii) Reacting triazole phosphate compound (14') and substituted benzaldehyde in alcohol followed by addition of acid to obtain imine (15');
  (iv) Deprotecting partially the imine (15') with azide to obtain monophosphonate ester (16'); and
  (v) Fluorinating the monophosphonate ester (16') with DAST to obtain fluorinated monophosphonate ester of pH-sensitive probe (17').

The process is depicted below as Scheme 5

Scheme 5

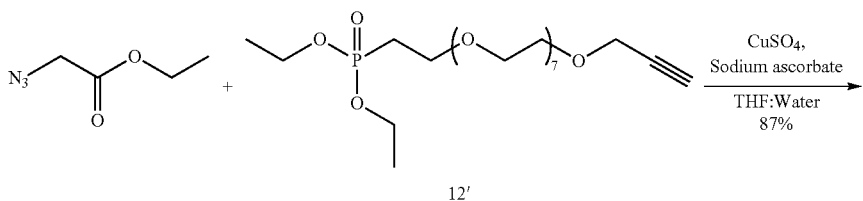

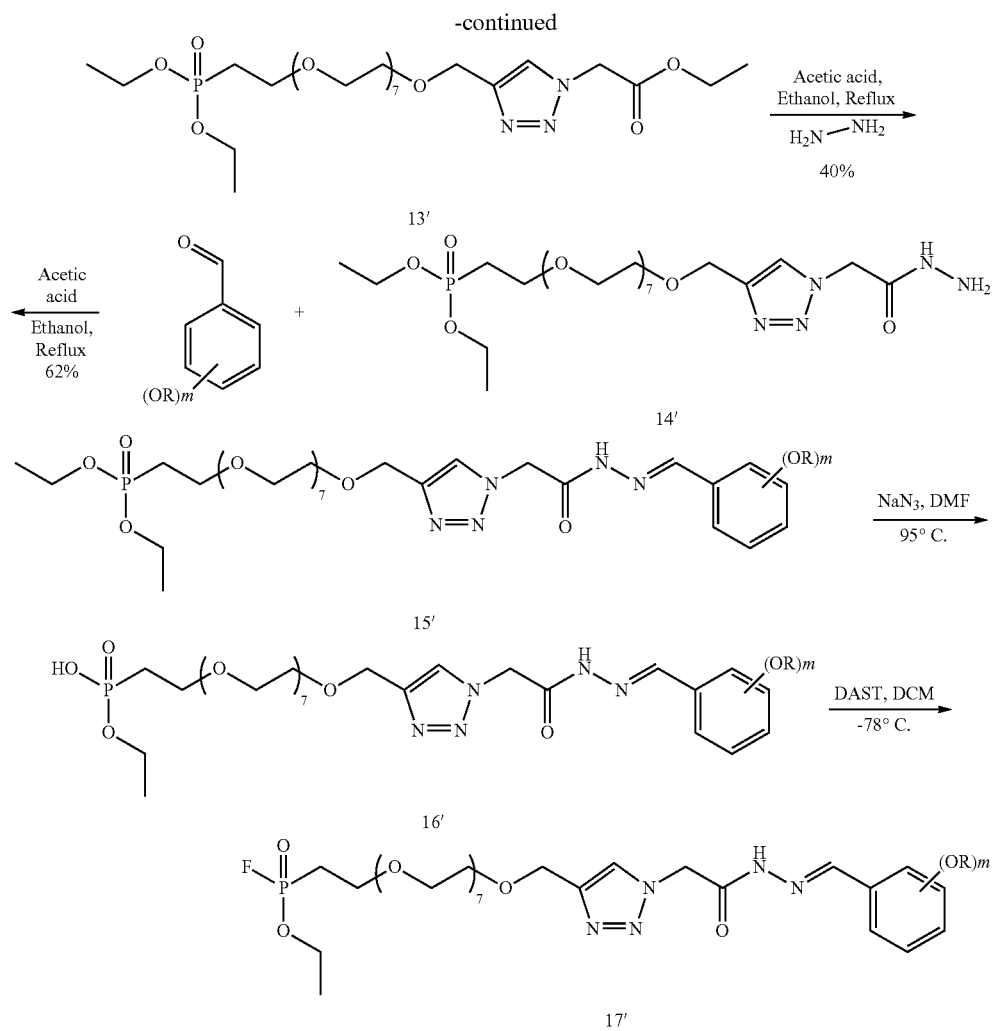

wherein 'R' and 'm' are as defined above.

According to Scheme 5, the first step comprises reacting ethyl bromo acetate with sodium azide in water acetone mixture in the ratio 1:3 at temperature of about 60° C. for 3-4 hours. The reaction mixture was quenched with water and extracted in solvent. The combined organic layer was dried and purified to obtain ethyl 2-azidoacetate. To the azido compound was further added alkyne terminated OEG spacer (12') in equimolar ratio in degassed polar aprotic solvent selected from THF, DMF and the like and the mixture was stirred until clear solution. To the clear solution was added degassed water, stirred, followed by addition of freshly prepared 1M sodium ascorbate and 1M CuSO$_4$ at least thrice in an interval of 45 minutes and allowed to react for about 16 hours at RT. Upon completion, reaction mixture was extracted in solvent, the combined organic layers were dried, filtered and purified to obtain ethyl4-((2-(2-(diethoxyphosphoryl)ethoxy)methyl)-1H-1,2,3-triazol-1-carboxylate (13').

The step (ii) comprises dissolving the ester (13') and hydrazine in excess amount in absolute ethanol with stirring and refluxing for about 12 hours. Upon completion of reaction, excess of ethanol and hydrazine was removed under vacuum. To the obtained residue water was added and washed with organic solvent. The water layer was evaporated under vacuum to get crude product which was purified to obtain pure compound (14').

In step (iii) to the mixture of compound (14') and substituted benzaldehyde in 1:2 molar ratio was added ethanol followed by addition of acetic acid and refluxing the mixture for about 10-13 hours. Upon completion of reaction, ethanol was removed under vacuum and the obtained residue was loaded and purified to get diphosphonate ester (15').

Step (iv) comprises conversion of imine diphosphonate ester (15') to imine monophosphonate(16'). Accordingly, mixture of imine diphosphonate ester (15') and sodium azide (excess) were dissolved in polar aprotic solvent, stirred, heated in the range of 90-100° C. for 15-20 hours. Upon completion of reaction, the solvent was evaporated under vacuum. Water was added to the residue and extracted in solvent, concentrated the combined organic layers, and the crude product ethyl hydrogen imine phosphonate(16') was used as such in the next step without purification.

According to Step (vii), to stirred solution of compound (16') in solvent maintained at temperature in the range of −70° C. to −80° C., Diethyl amino sulphur trifluoride (DAST) was added dropwise at RT and allowed to react for about 10 to 15 minutes. Excess of DAST and the solvent were evaporated under vacuum. The obtained residue was extracted in solvent and the combined organic layers were dried, concentrated under vacuum to yield pH-sensitive probe (17').

Synthesis of alkyne terminated octa ethylene glycol spacer: In yet another embodiment, the Alkyne terminated octa ethylene glycol spacer, (12') was prepared by a process which comprises;
- (i) Reaction of tetraethylene glycol and NaH to yield compound (8');
- (ii) Reaction of Tetraethylene glycol with Tosyl chloride to yield compound (9');
- (iii) Dimerization of compounds 8' and 9' to obtain compound (10') as tosylate;
- (iv) Refluxing compound (10') with KI in acetone to yield iodo compound (11');
- (v) Refluxing iodo compound (11') and triethylphophite to yield compound (12'); The process is depicted in Scheme 6 below:

mixture was stirred for another 10-12 hours until completion of the reaction. Upon completion, reaction was quenched with aqueous ammonium chloride, and extracted in solvent to get crude product which was further purified to obtain ditosyl tetraethylene glycol((i.e. oxybis(ethane-2,1-diyl))bis(oxy))bis(ethane-2,1-diyl) bis(4-methylbenzenesulfonate) (9').

The mono benzyl tetraethylene glycol(8') and ditosyl tetraethylene glycol(9') in 1:2 ratio were dissolved with stirring in organic solvent at 0° C. and sodium hydride was added instantly to the mixture in portions and stirred for 30-40 hours at RT. Upon completion, NaH was quenched by addition of water at 0° C. and extracted in solvent to get crude product which was further purified to obtain 3,6,9,12,

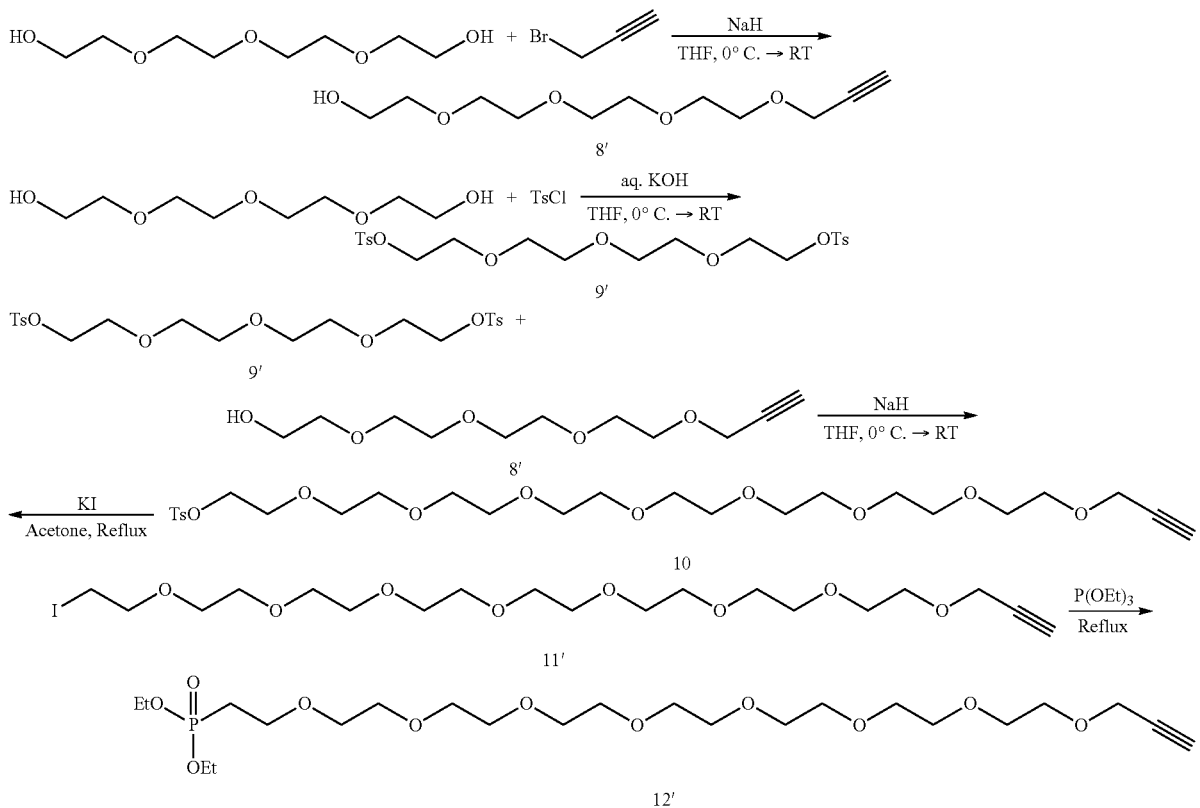

Scheme 6

According to Scheme 6, one portion of tetraethylene glycol was dissolved with stirring in polar aprotic solvent at 0° C. Sodium hydride (NaH) was added in small portions immediately followed by drop wise addition of propargyl bromide at same temperature. The reaction was stirred at RT and upon completion of the reaction, excess NaH was quenched with drop wise addition of water. The resulting reaction mixture was extracted in solvent, the combined organic layers were dried, concentrated and purified to obtain monobenzyltetraethylene glycol (i.e. 3,6,9,12-tetraoxapentadec-14-yn-1-ol)(8').

To the other portion of tetra ethylene glycol dissolved in organic solvent selected from polar aprotic solvent was added aq. KOH in small portions immediately. After about 10 minutes, tosyl chloride was added drop wise and the 15,18,21,24-octaoxaheptacos-26-yn-1-yl 4-methylbenzenesulfonate (10').

A mixture of compound (10') and KI (excess) was refluxed in acetone for about 18 hours. Upon completion, excess KI was filtered and washed severally with acetone. The collected acetone fraction was evaporated under vacuum to get residue, which was washed with water and extracted in solvent. The combined organic layer was washed with aqueous $Na_2CO_3$, concentrated under vacuum to get crude product1-iodo-3,6,9,12,15,18,21,24-octaoxaheptacos-26-yne(11') which was further purified.

The iodide compound (11'), triethylphosphite, $P(OEt)_3$ (excess) were refluxed for about an hour at 100-150° C. The excess $P(OEt)_3$ was removed under vacuum and the reaction mixture was purified.

Design of Redox-Sensitive Supramolecular Protein Conjugate

In yet another embodiment, the present invention discloses redox-sensitive protein conjugate, which can make supramolecular protein assembly, of formula (IA'");

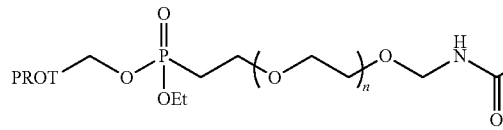 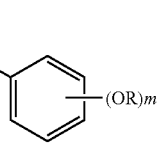

(IA''')

which comprises;
a hydrophilic protein head group PROT with a length of up to 500 amino acids selected from the group consisting of serine proteases, cysteine proteases, aspartic proteases, metalloproteases such as trypsin, chymotrypsin, subtilisin, elastase, and mixtures thereof;
a hydrophilic spacer comprising a phosphonate ester of oligoethylene glycol;
hydrophobic tails or dendrons comprising a substituted phenyl group, wherein 'R' represents C4-C20 (un)substituted or substituted straight, branched, cyclic or acyclic aliphatic, aromatic or alkyl or alkoxy aryl moieties; linear or branched polymers, dendrimers, hydrophobic peptides or proteins, and
a disulfane moiety (D) sensitive to redox change that is located between the hydrophilic spacer and the hydrophobic tail;
'n' represents the integer 1 to 20;
'm' represents the integer 1 to 4;
wherein said supramolecular protein assembly disassembles irreversibly in response to redox change.

Accordingly, the present invention discloses supramolecular protein assembly sensitive to redox change, which comprises Try-OEG-SS-C12-2T of the formula (IA''') given below, where TRYP is trypsin;

In another embodiment, the redox-sensitive protein conjugate, which can make supramolecular protein assembly, of Formula (IA''') prepared by the process of the present invention have the particle size in the range of 10-1000 nm.

Figure 20:
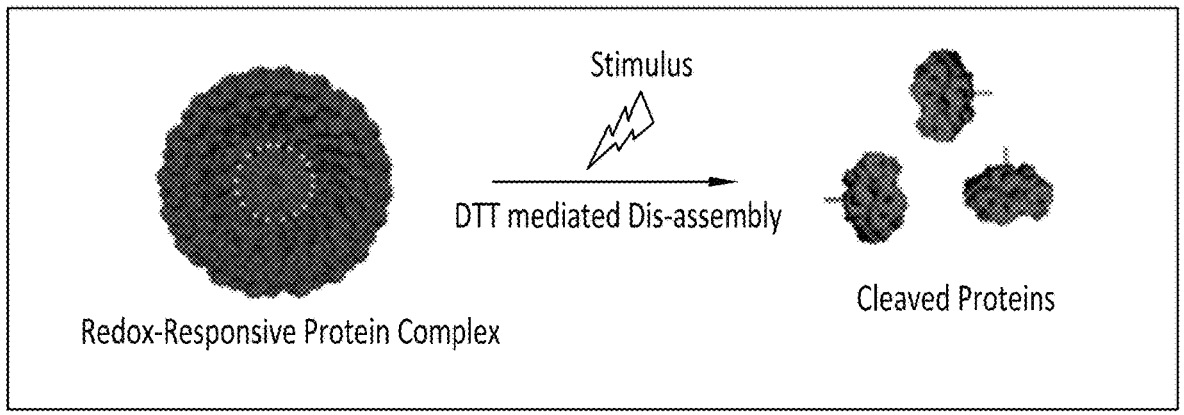
FIG. 20 shows disassembly of redox-sensitive protein conjugates.

SEC and MALDI-ToF MS. This study revealed that the 30 eq of DTT is sufficient to dis-assemble the complex completely due to the clipping of hydrophobic tail by DTT, as shown in FIG. 20. Further, the complex was incubated with 30 eq of DTT for different time points. The SEC studies reveals that, in 15 mins 80% of complex dis-assembles, whereas in 30 mins it disassembles to 90%; while the complete cleavage is observed in 60 mins.

Control Experiments for Redox Dis-Assembly Studies

In order to see the effect of DTT on the protein, we have carried out three control experiments. In the first experiment, we have incubated the native trypsin with DTT for 12 hours. The SEC profiles shows that the protein undergoes degradation in either due to the presence of DTT or autolysis. In the second experiment, we blocked the active site of protein with the flurophosphonate to prevent the autolysis and these sample was incubated with DTT. The SEC experiment revealed that the DTT alone has no effect on the elution volume. Further, the incubation of DTT with the Try-OEG-C12-2T (non-stimuli complex) also showed no effect on elution volume, indicating that complex is stable in presence of DTT.

Synthesis of Redox-Sensitive Supramolecular Protein Conjugate

In an embodiment, the process for preparing the supramolecular redox-sensitive protein assembly of formula (IA''') comprises of following steps;
(i) Homogenizing the AABP probe (18') in triton X-100 and sodium phosphate buffer at pH 7.4 and adding the homogenized mixture to the protein solution in sodium phosphate buffer at pH 7.4 and allowing to react;
(ii) Removing triton X-100 from the protein mixture using Ion exchange chromatography and eluting the native and smart protein conjugate using eluting buffer solution;

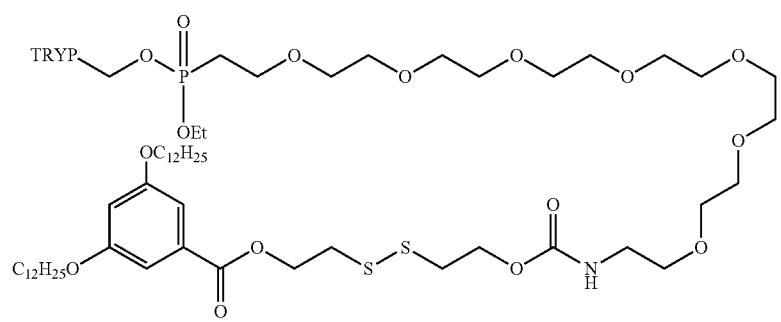

(IA''')

The redox-sensitive protein conjugate was dissolved in 50 mM sodium phosphate pH 7.4 in a 2 mL centrifuge tube and room temperature was maintained over the entire reaction. Different equivalent of DTT (aq. solution) was added and then the sample was incubated for 12 hours after gentle mixing with pipette. After that, sample was analysed using (iii) Removing the native protein from the conjugate in high salt concentrations using size exclusion chromatography followed by desalting and lyophilizing to obtain pure protein conjugate (IA''').

The protein in step (i) is selected from hydrophilic protein with a length of up to 500 amino acids, preferably the protein is trypsin. The complex size of the redox-sensitive protein conjugate was observed to be 11 nm.

The process is schematically shown below in Scheme 7:

Scheme 7

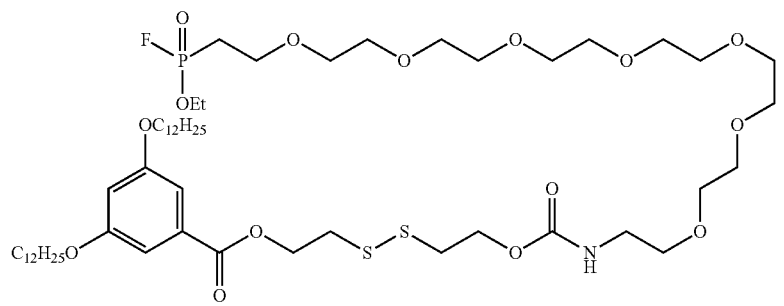

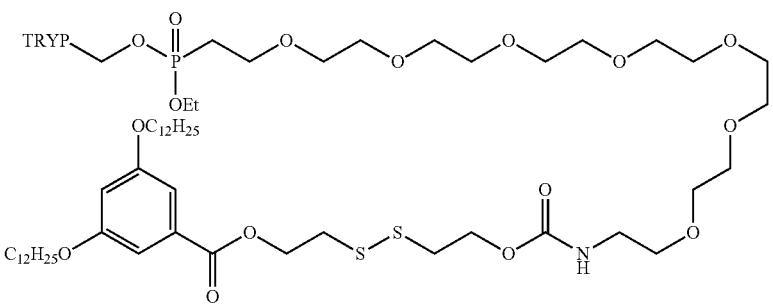

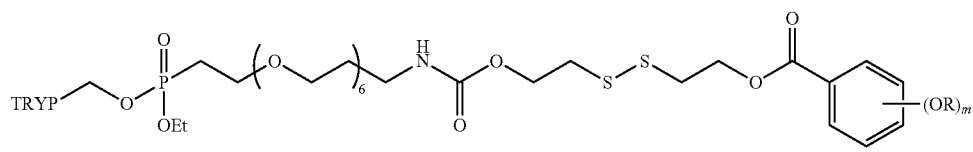

wherein 'R' and 'm' are as defined above.

Synthesis of Redox-Sensitive Probe

The redox-sensitive probe (18'f) is synthesized by the process which comprises;
(i) Reacting 2,2'-disulfanediylbis(ethan-1-ol) and 3,5-bis (dodecyloxy)benzoic acid (18'a) in presence of condensing agent and solvent(s) to obtain crude 3,5-bis (dodecyloxy)benzoic acid (18'b);
(ii) Activating the compound (18'b) of step (a) with coupling agent in the presence of base to yield activated ester 2-((2-((((2,5-dioxopyrrolidin-1-yl)oxy)carbonyl) oxy)ethyl)disulfaneyl)ethyl3,5-bis(dodecyloxy)benzoate (18'c);
(iii) Reacting activated ester (18'c) of step (b) with amine (Ii) in the presence of base and solvent to obtain diphosphonate ester, 3,3-(diethoxyphosphoryl)-8-oxo-7,13,16,19,22,25,28,31-octaoxa-3,4-dithia-9-azatritriacontyl 3,5-bis(dodecyloxy)benzoate (18'd);

(iv) Heating the diphosphonate ester (18'd) of step (iii) to get monophosphonate ester, 3,3-(ethoxy(hydroxy) phosphoryl)-8-oxo-7,13,16,19,22,25,28,31-octaoxa-3, 4-dithia-9-azatritriacontyl 3,5-bis(dodecyloxy)benzoate (18'e) and fluorination using DAST in solvent to yield redox-sensitive probe 33-(ethoxyfluorophosphoryl)-8-oxo-7,13,16,19,22,25,28,31-octaoxa-3,4-dithia-9-azatritriacontyl 3,5-bis(dodecyloxy)benzoate (18'f).

The process is depicted below as Scheme 8:

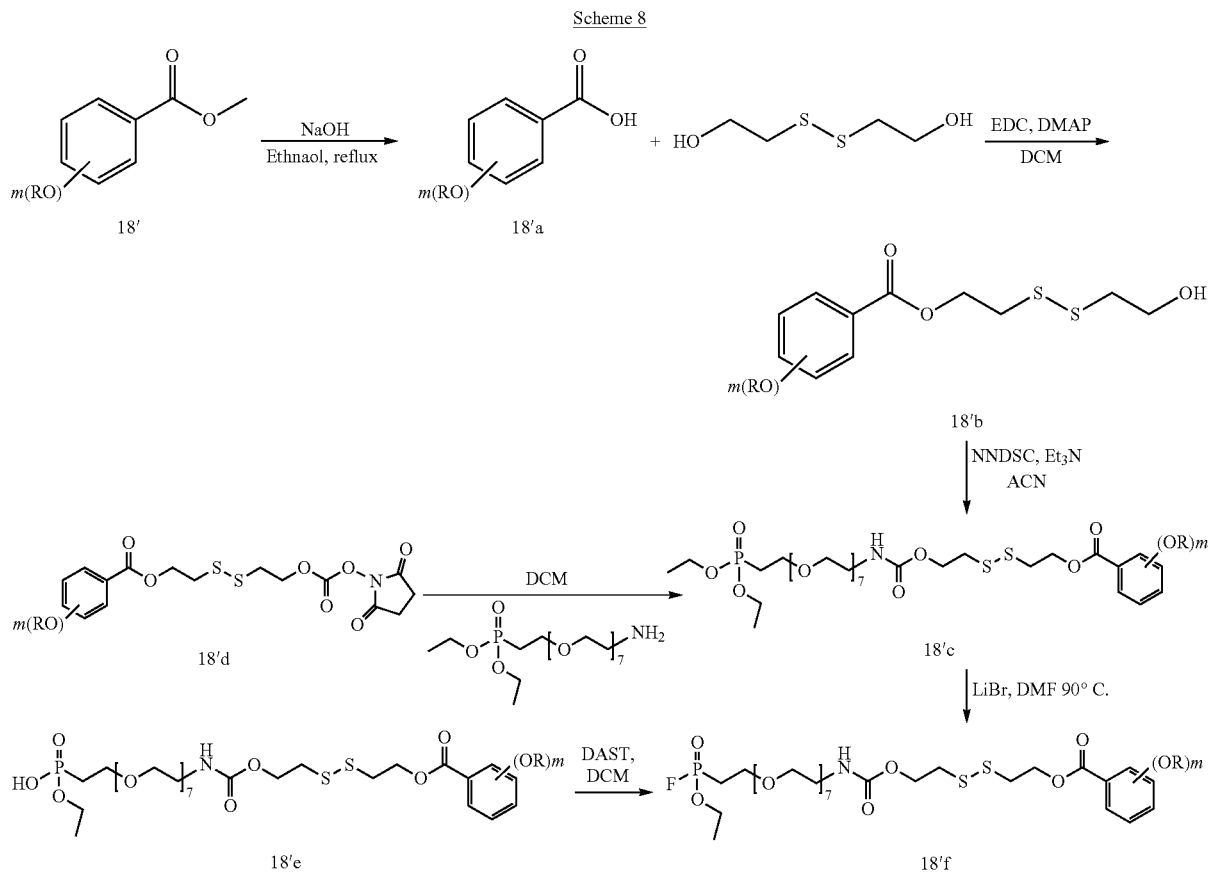

Scheme 8

According to the Scheme 8, the first step comprises basic hydrolysis of the ester compound (18') in alcohol under reflux. Quenching the product with dropwise addition of water and acidifying with conc. HCl. The obtained precipitate was filtered and washed with alcohol. The combined organic layer was dried and concentrated to get crude 3,5-bis(dodecyloxy)benzoic acid (18'a) which was utilized for next reaction without further purification.

In the first step, compound (18'a), 2,2'-disulfanediylbis(ethan-1-ol) and 4-Dimethylaminopyridine (DMAP) were taken and dissolved in dichloromethane (DCM) under stirring. Solution of 1-Ethyl-3-(3-dimethylaminopropyl)carbodiimide (EDC) in DCM was added slowly to above mixture and allowed to stir. Upon completion, reaction was quenched with water and resulting content was extracted in DCM, combined organic layers was dried and concentrated under reduced pressure to get crude2-((2-hydroxyethyl)disulfaneyl)ethyl 3,5-bis(dodecyloxy)benzoate (18'b) which was purified.

According to second step, the compound (18'b) was activated in presence of N,N'-DSC and organic base to obtain the compound 2-((2-((((2,5-dioxopyrrolidin-1-yl)oxy)carbonyl)oxy)ethyl)disulfaneyl)ethyl 3,5-bis(dodecyloxy)benzoate (18'c).

In the third step, the compound (18'c) was condensed with phosphoryl amine (Ii) in presence of polar solvent to obtain 3,3-(diethoxyphosphoryl)-8-oxo-7,13,16,19,22,25,28,31-octaoxa-3,4-dithia-9-azatritriacontyl 3,5-bis (dodecyloxy) benzoate (18'd), which was further converted to mono phosphate compound, 3,3-(ethoxy(hydroxy)phosphoryl)-8-oxo-7,13,16,19,22,25,28,31-octaoxa-3,4-dithia-9-azatritriacontyl 3,5-bis(dodecyloxy)benzoate (18'e) in presence of LiBr and organic solvent at a temperature in the range of 80-100° C. The product was used as such in the next step without purification.

According to Step (iv), to stirred solution of compound (18'e) in solvent maintained at temperature in the range of −70° C. to −80° C., Diethyl amino sulphur trifluoride (DAST) was added drop wise at RT and allowed to react for about 10 to 15 minutes. Excess of DAST and the solvent were evaporated under vacuum. The obtained residue was extracted in solvent and the combined organic layers were dried, concentrated under vacuum to yield redox-sensitive probe3,3-(ethoxyfluorophosphoryl)-8-oxo-7,13,16,19,22, 25,28,31-octaoxa-3,4-dithia-9-azatritriacontyl 3,5-bis(dodecyloxy)benzoate (18'f).

The amine terminated octa ethylene glycol spacer was prepared by the process similar to the process depicted in Scheme 3.

In another embodiment, the present invention relates to the dis-assembly of protein conjugate which make supramolecular protein assembly of formula (IA''') having redox-sensitive probe (18'f). Accordingly, the protein conjugate which make supramolecular protein assembly of formula (IA''') was dissolved in 50 mM sodium phosphate at pH 7.4 at room temperature. Different equivalent of aq. solution of Dithiothreitol (DTT) was added and the sample was incubated for about 12 hours after gentle mixing. The sample was analysed using SEC and MALDI-ToF MS. The SEC studies revealed that, in 15 mins 80% of complex disassembles, whereas in 30 mins it disassembles to 90%; while the complex completely cleaved in 60 mins.

Design of Multi Stimuli-Sensitive Supramolecular Protein-Dendron Conjugates

Figure 21:
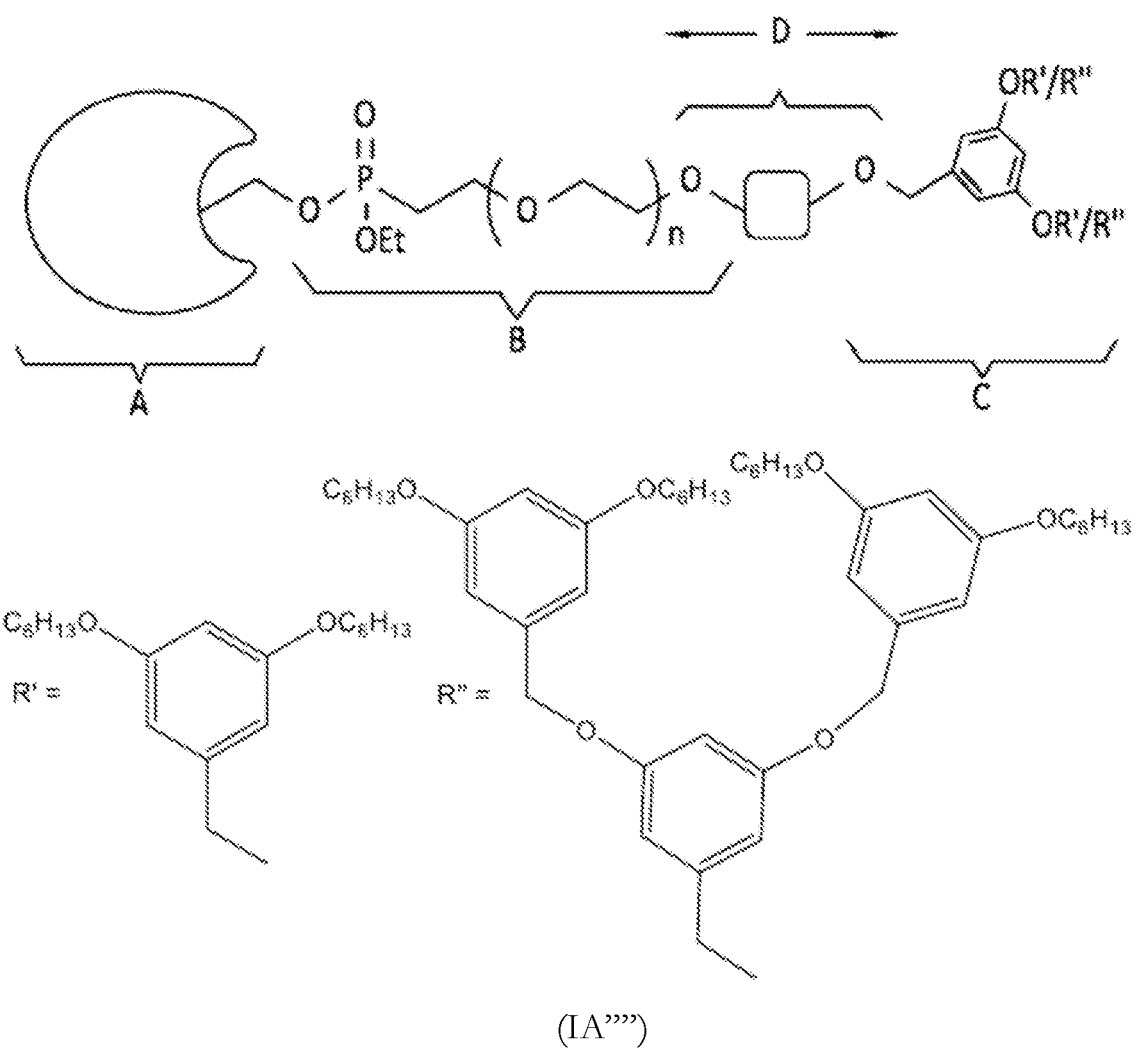
FIG. 21 shows multi stimuli-sensitive protein-dendron conjugates.

In yet another embodiment, the present invention discloses multi stimuli-sensitive protein-dendron conjugates of Formula (IA''''), as shown in FIG. 21.

The conjugate of Formula (IA'''') comprises;
a hydrophilic protein head group (A) with a length of up to 500 amino acids selected from the group consisting of serine proteases, cysteine proteases, aspartic proteases, metalloproteases such as trypsin, chymotrypsin, subtilisin, elastase, and mixtures thereof;
a hydrophilic spacer (B) comprising phosphonate ester of oligoethylene glycol;
hydrophobic Gn dendron (C) represented by groups R' and R'';
the multi stimuli-sensitive moiety (D) located between the hydrophilic portion (B) and the hydrophobic dendrimer tail (C);
'n' is the integer 1 to 20;
wherein said supramolecular protein assembly disassembles irreversibly in response to any exogenous or endogenous stimuli.

In an embodiment, the multi stimuli-sensitive protein conjugate of Formula (IA) comprises; the protein chymotrypsin; the cetyl ethylene glycol (CEG) as spacer, the photo-sensitive 2-nitrobenzyl group and the hydrophobic dendron (G1) as below, where CYM is chymotrypsin;

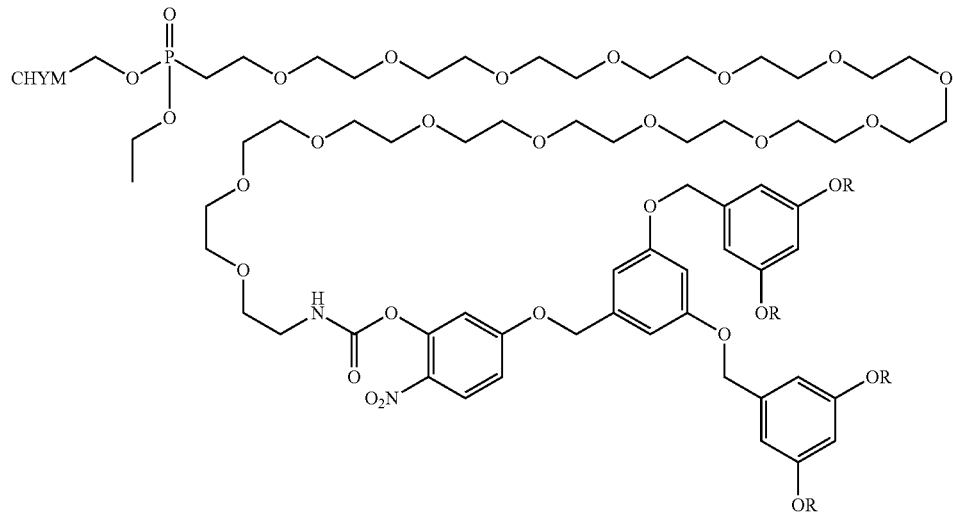

Chy-CEG-NB-G1

R = C$_6$H$_{13}$ (IA$^1$)

The multi stimuli-sensitive protein conjugate of Formula (IA$^2$) comprises; the protein chymotrypsin; the cetyl ethylene glycol (CEG) as spacer, the photo-sensitive 2-nitrobenzyl group and the hydrophobic dendron (G2) as below;

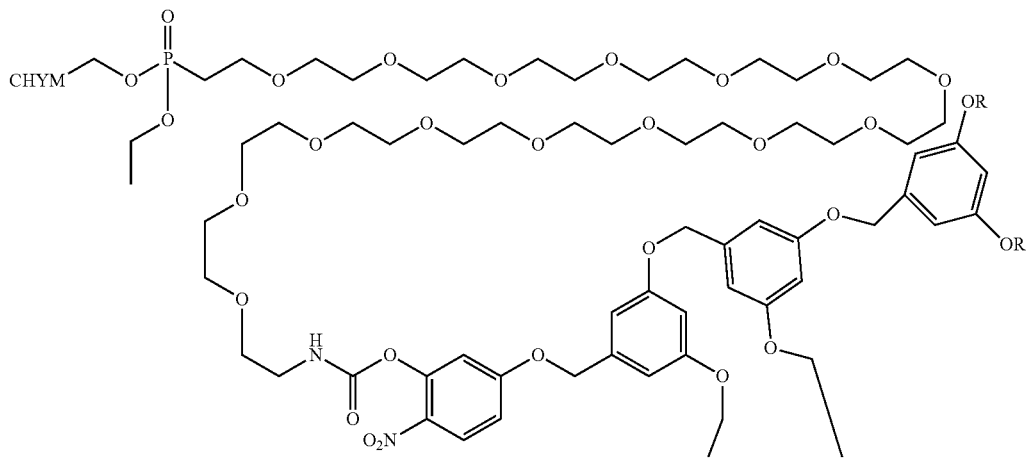

(IA$^2$)

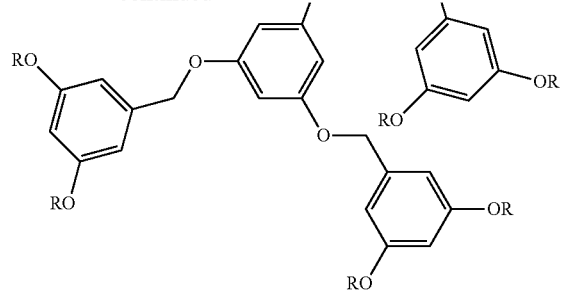

Chy-CEG-NB-G2

R = C$_6$H$_{13}$

The process for preparing the supramolecular multi stimuli-sensitive protein assembly of formula (IA"") comprises of following steps;

Synthesis of Multi Stimuli-Sensitive Supramolecular Protein-Dendron Conjugates
(i) Homogenizing the AABP probe (19'f or 20'f) in triton X-100 and sodium phosphate buffer at pH 7.4 followed by addition of the protein solution to the homogenized solution in sodium phosphate buffer at pH 7.4 and allowing it to react;
(ii) Removing triton X-100 from the protein mixture using Ion exchange chromatography and eluting the native and smart protein conjugate using eluting buffer solution;
(iii) Removing the native protein from the conjugate in high salt concentrations using size exclusion chromatography followed by desalting and lyophilizing to obtain pure protein conjugate (IA"").

The protein in step (i) is selected from hydrophilic protein with a length of up to 500 amino acids, preferably the protein is chymotrypsin.

The synthesis of Chy-CEG-NB-G1 is shown below in Scheme 9, where CHYM is chymotrypsin;

Scheme 9

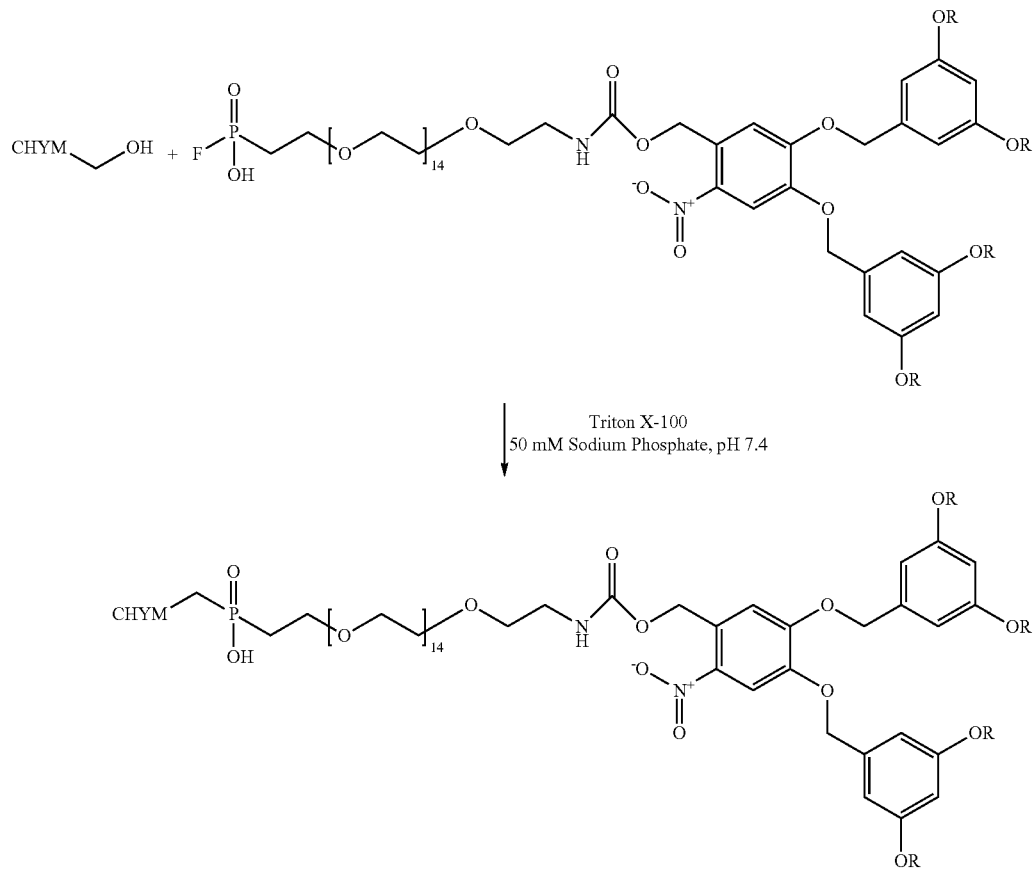

The synthesis of Chy-CEG-NB-G2 is shown below in Scheme 10, where CHYM is chymotrypsin;

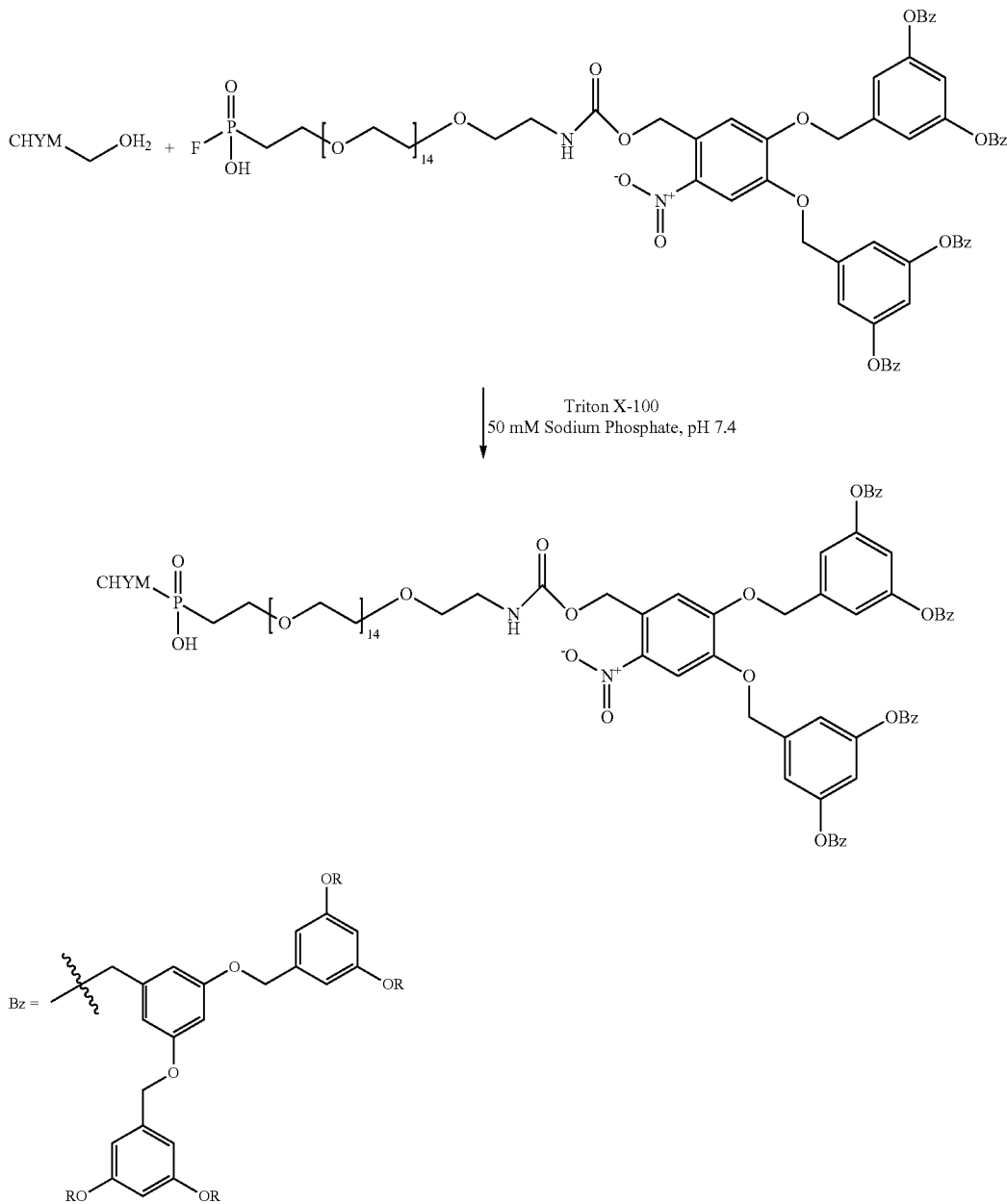

Dis-Assembly of Multi Stimuli-Sensitive Supramolecular Protein-Dendron Conjugates Programmed Self-Assembly of Multi Stimuli-Sensitive Protein Complex The photo-sensitive protein-dendron complex was synthesized by conjugating photo-sensitive macromolecular AABP (19'f or 20'f) to the chymotrypsin. The photo-sensitive 2-nitrobenzyl group is located in between hydrophilic portion (chymotrypsin and cetylethylene glycol) and a hydrophobic dendron. The self-assembling property of protein-dendron conjugates was validated using complementary techniques such as Dynamic light scattering (DLS) and Size-exclusion chromatography (SEC). DLS measurements revealed the trend in the hydrodynamic radii (Rh) of photo-sensitive protein dendron complexes. The radius of the Chy-CEG-NB-G1 complex was found to be 5.0 nm, whereas Chy-CEG-NB-G2 complexes showed radius 6.8 nm. The study showed that the size of protein-dendron complexes increases with an increase in the generation and emphasizes the effect of dendrimer volume on the size of protein-dendron complexes. The elution volume in SEC experiment also manifests the same trend as DLS. The Chy-CEG-NB-G2 forms the bigger complex with the elution volume of 10.1 compared to Chy-CEG-NB-G1 which elutes at 10.9 mL. To probe the surface charges of these photo-sensitive complexes, zeta potential measurement was performed. The surface charge of Chy-CEG-NBG1 is −6 mV) whereas Chy-CEG-NB-G2 is −8 mV.

Partial Dis-Assembly of Photo-Sensitive Protein Complex (Chy-CEG-NB-G1-G3 (IA""))

Figure 1A:
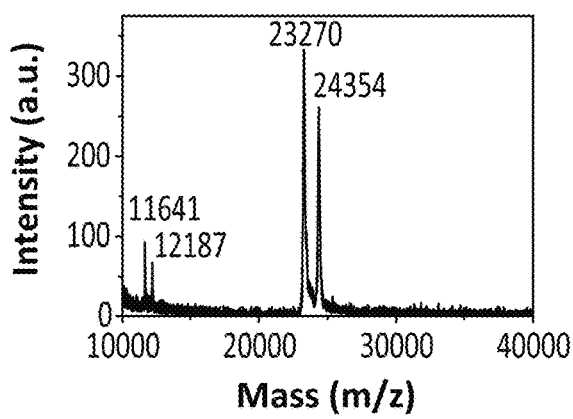
FIG. 1A depicts MALDI-TOF MS spectrum of reaction mixture of trypsin and photo-sensitive probe (9).
Figure 1B:
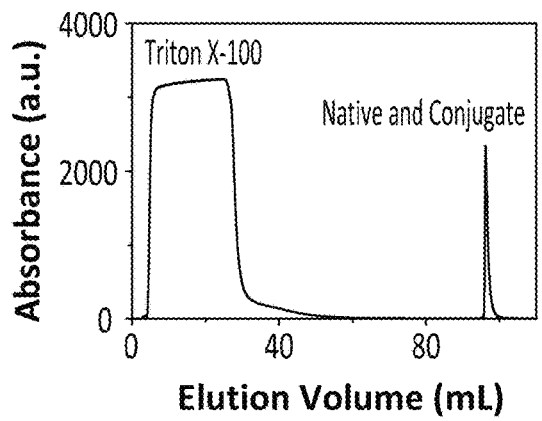
FIG. 1B depicts IEX chromatogram showing separation of triton X-100 and protein mixture.
Figure 1C:
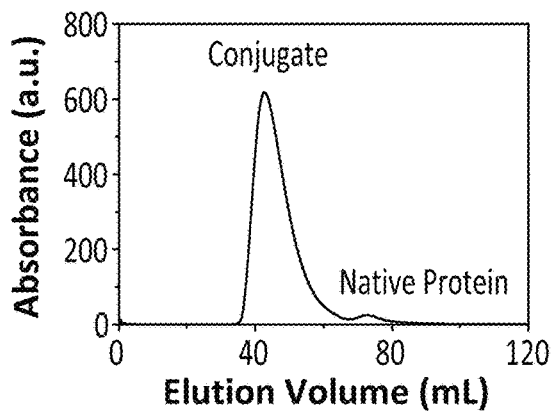
FIG. 1C depicts SEC chromatogram showing separation of protein conjugate (IA') and native protein.
Figure 1D:
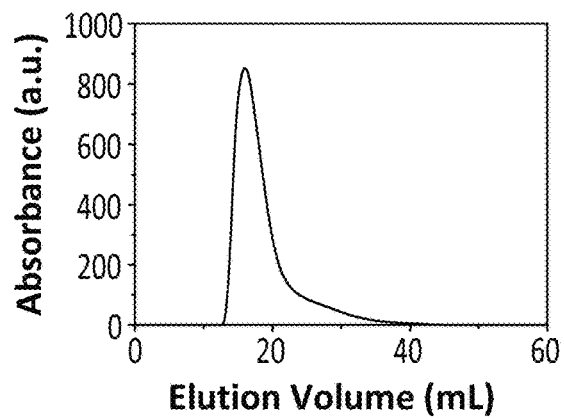
FIG. 1D depicts Desalting chromatogram of purified protein conjugate (IA')
Figure 1E:
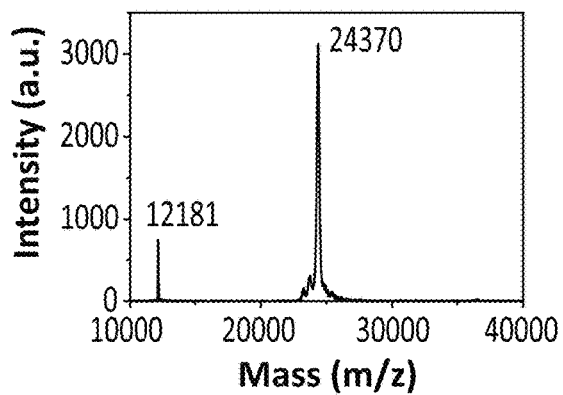
FIG. 1E depicts MALDI-TOF MS of purified protein conjugate (IA')
Figure 2A:
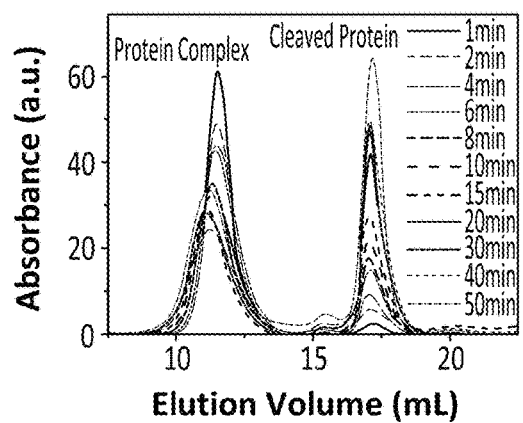
FIG. 2A depicts overlaid SEC chromatograms for photo cleavage of the supramolecular protein assembly (IA') after 50 minutes.
Figure 2B:
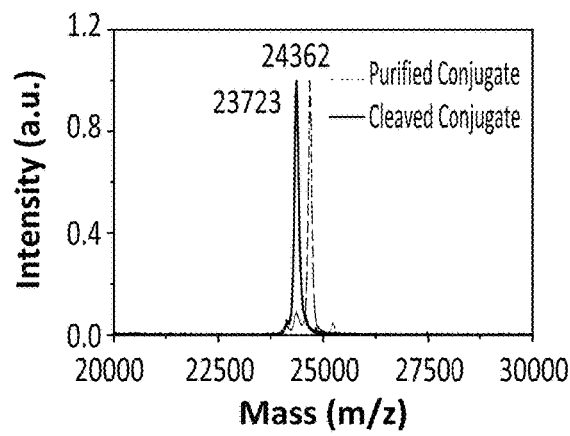
FIG. 2B depicts overlaid MALDI-TOF MS spectra of cleaved conjugate with respect to conjugate (IA')
Figure 2C:
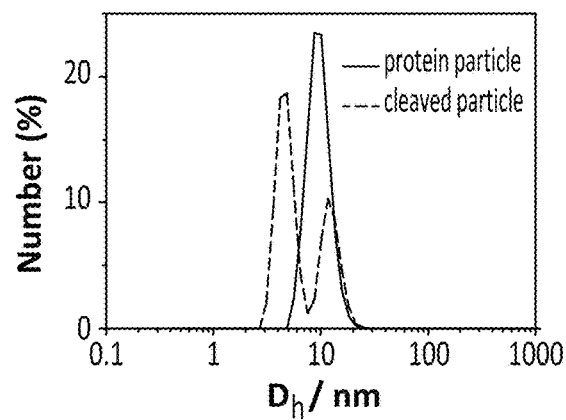
FIG. 2C depicts DLS data for photo dis-assembly of the supramolecular protein assembly (IA').
Figure 2D:
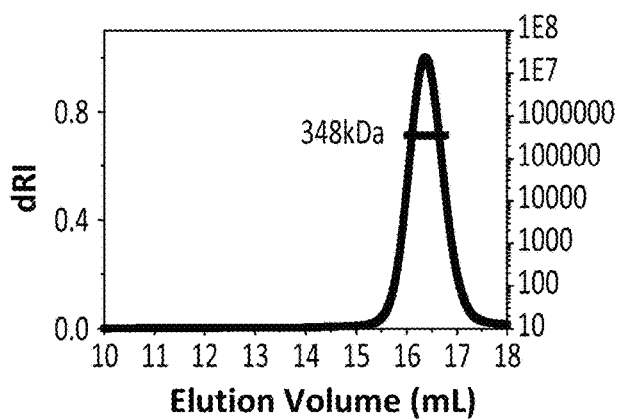
FIG. 2D depicts SEC-MALS data of protein conjugate (IA').
Figure 3A:
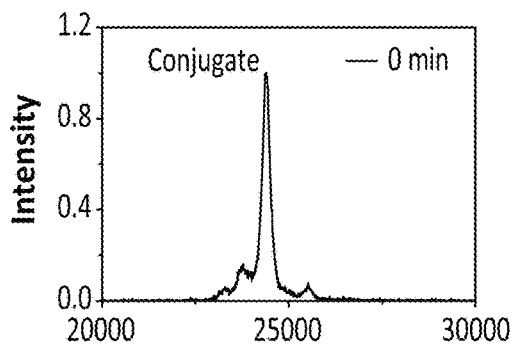
FIGS. 3A to 3G depict overlaid MALDI-TOF MS spectra of photo cleavage of the protein conjugate at different time points (IA')
Figure 3B:
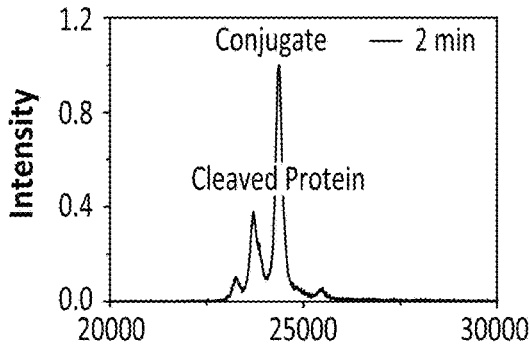
Figure 3C:
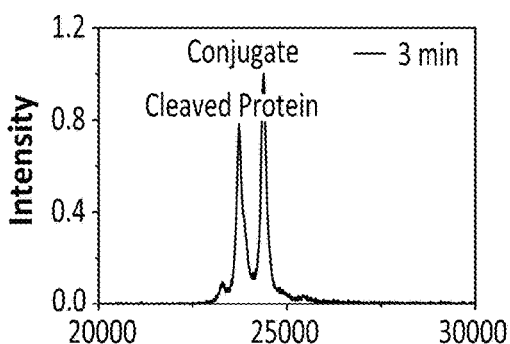
Figure 3D:
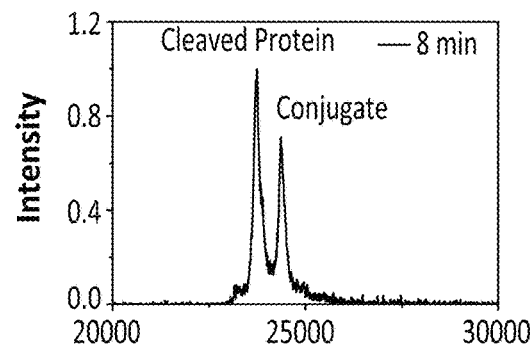
Figure 3E:
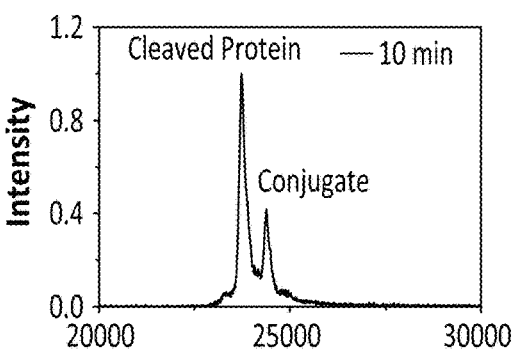
Figure 3F:
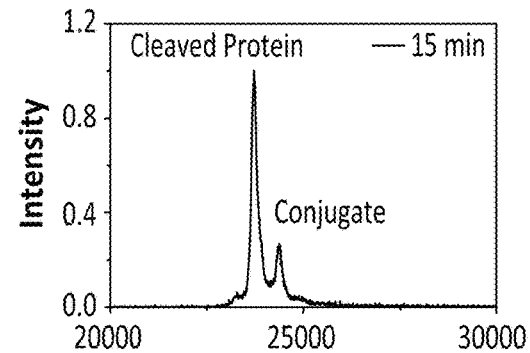
Figure 3G:
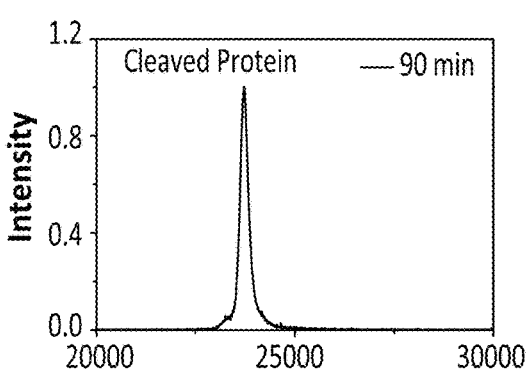
Figure 3H:
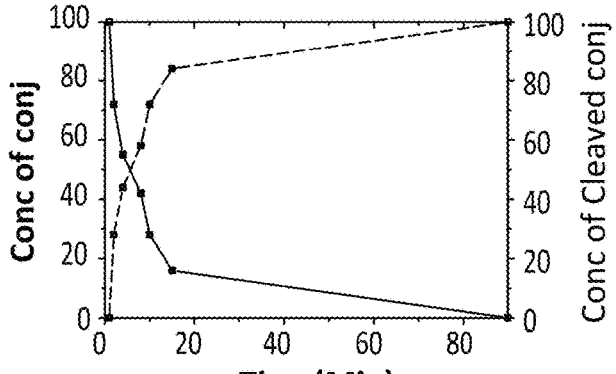
FIG. 3H depicts intensities/concentrations of the protein conjugate at different time points with respect to cleaved conjugate during photo cleavage (IA')
Figure 4A:
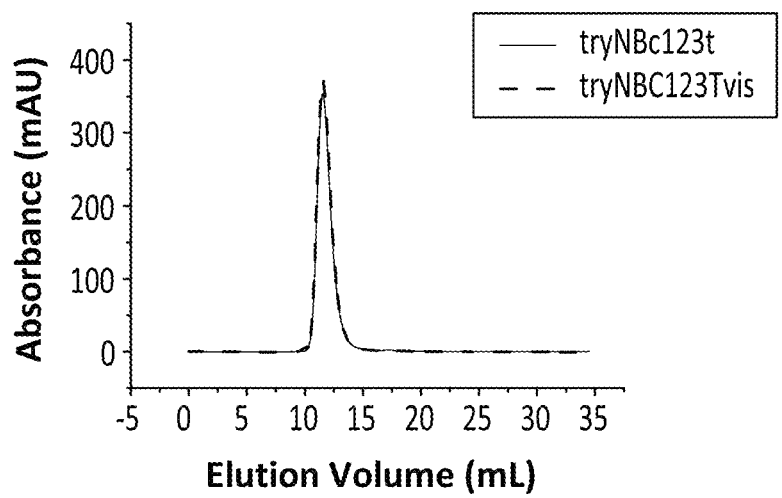
FIG. 4A shows SEC data obtained for Photo-sensitive Try-OEG-NB-C12-2T in response to the visible light.
Figure 4B:
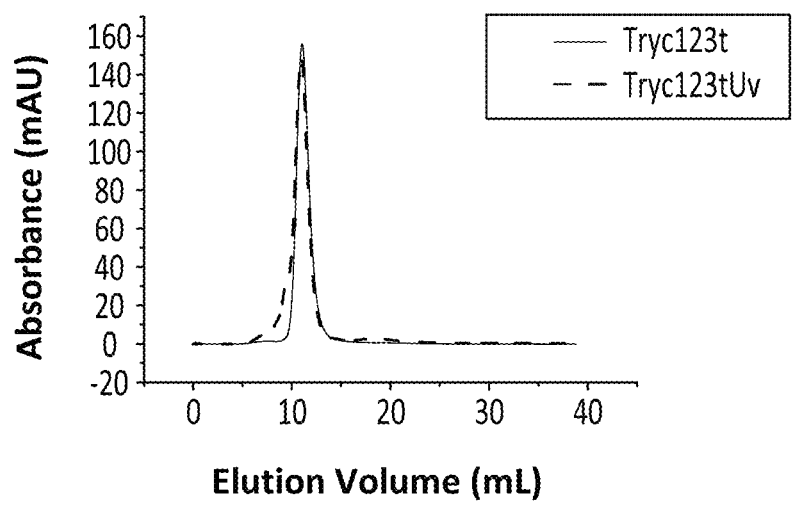
FIG. 4B shows SEC data obtained for protein conjugate Try-OEG-C12-3T in response to the UV light.
Figure 5A:
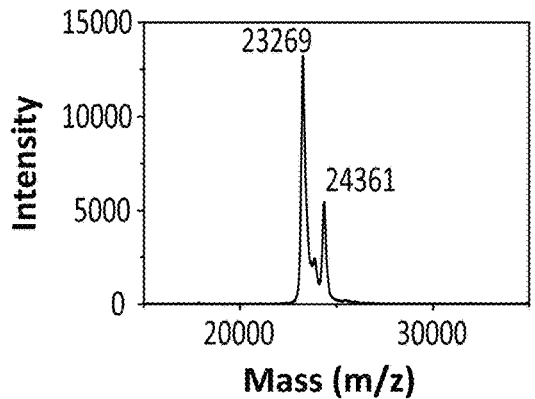
FIG. 5A depicts MALDI-TOF MS spectrum of reaction mixture of trypsin and pH-sensitive probe (17').
Figure 5B:
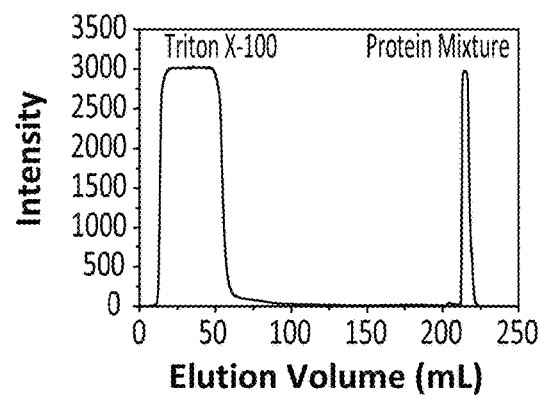
FIG. 5B depicts IEX chromatogram showing separation of triton X-100 and protein mixture.
Figure 5C:
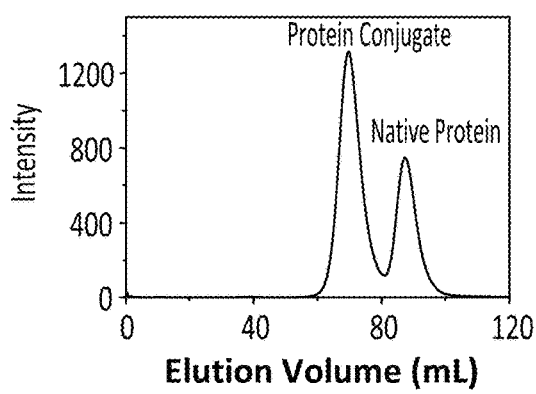
FIG. 5C depicts SEC chromatogram showing separation of protein conjugate (IA") and native protein.
Figure 5D:
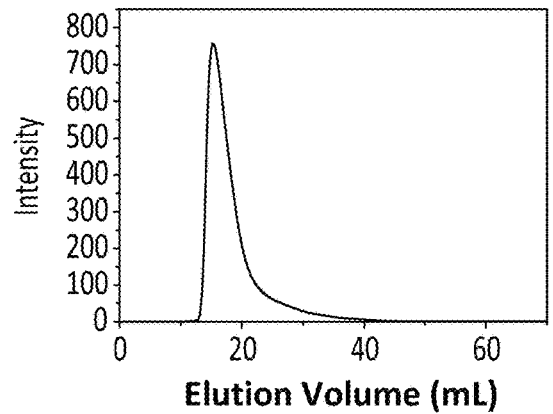
FIG. 5D depicts desalting chromatogram of protein conjugate (IA")
Figure 5E:
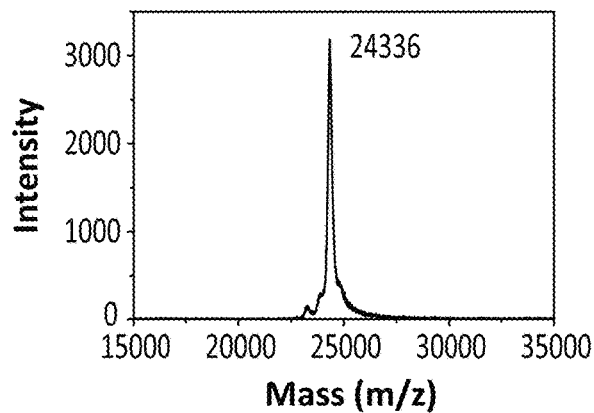
FIG. 5E depicts MALDI-TOF MS of purified protein conjugate (1A")
Figure 6A:
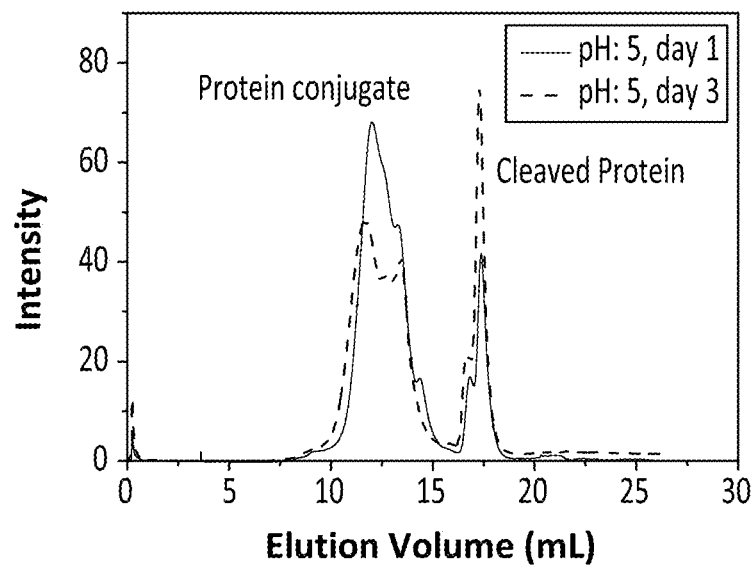
FIG. 6A depicts overlaid SEC chromatograms for pH cleavage of the supramolecular protein assembly (IA") after 3 days.
Figure 6B:
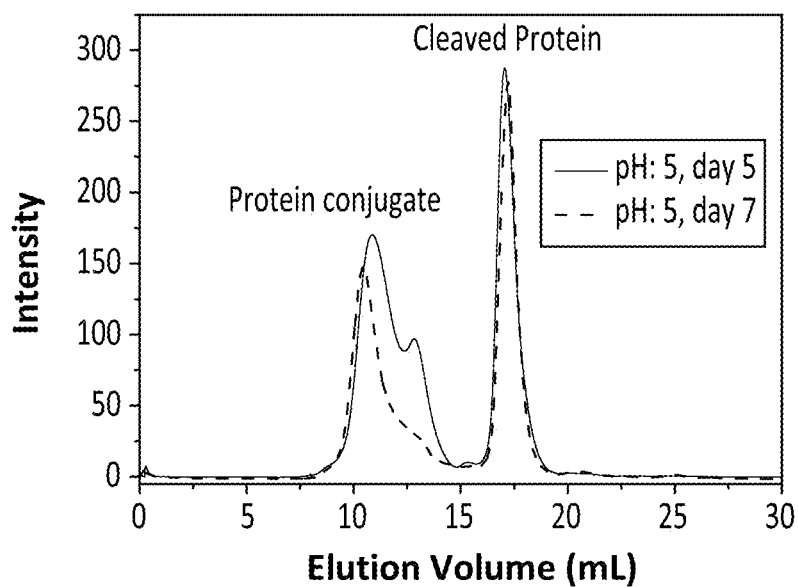
FIG. 6B depicts overlaid SEC chromatograms for pH cleavage of the supramolecular protein assembly (IA") after 7 days.
Figure 8A:
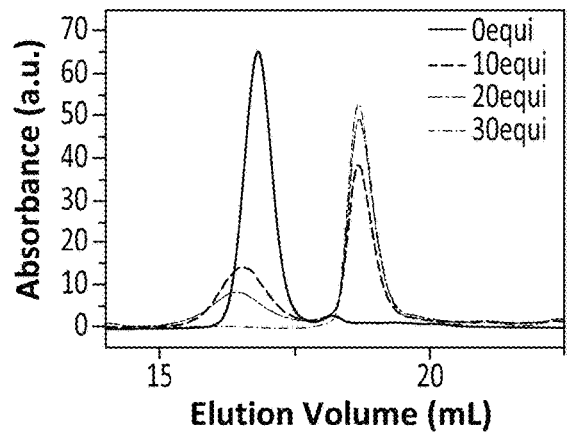
FIG. 8A Dis-assembly data for Try-OEG-SS-C12-2T complex with different equivalent of DTT.
Figure 8B:
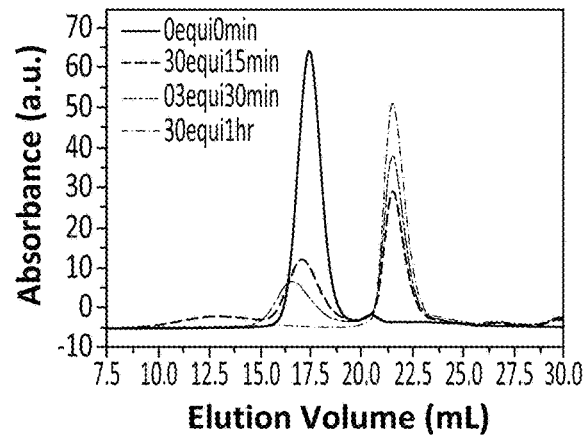
FIG. 8B Dis-assembly data for Try-OEG-SS-C12-2T complex at different time points with 30 eq of DTT.
Figure 8C:
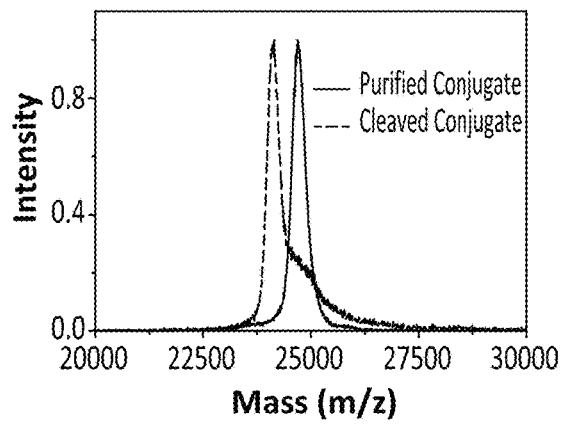
FIG. 8C MALDI-TOF spectra of purified and cleaved conjugate.
Figure 8D:
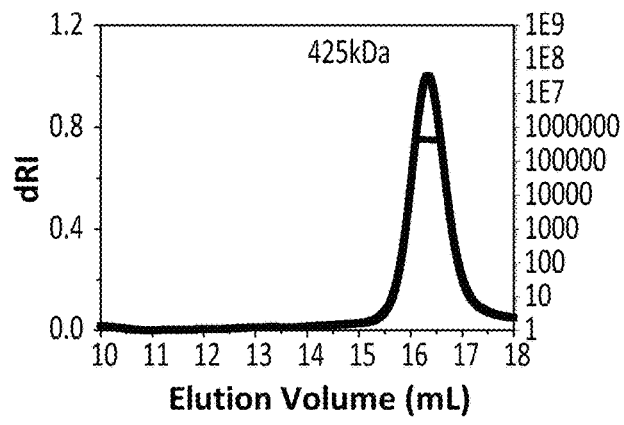
FIG. 8D depicts SEC-MALS data of protein conjugate (IA''').
Figure 9A:
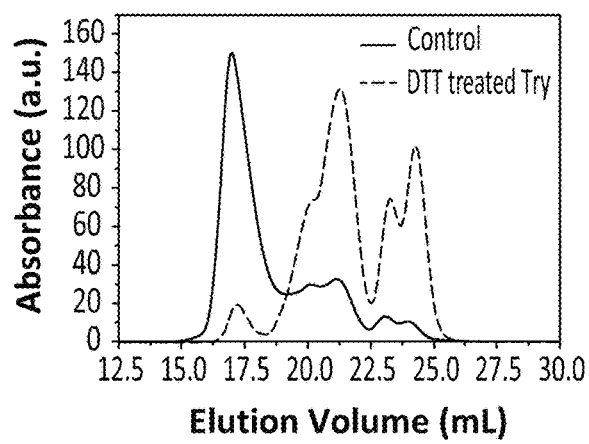
FIG. 9A SEC data for Try with and without DTT treatment.
Figure 9B:
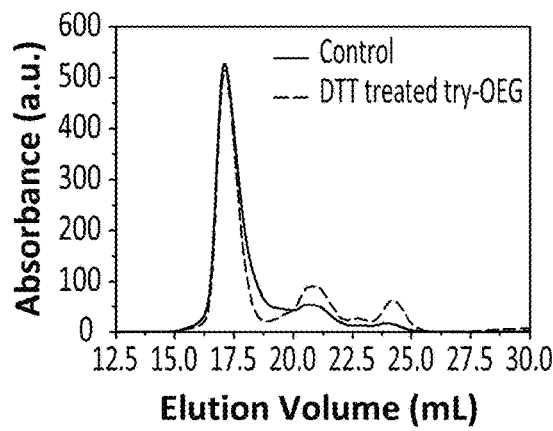
FIG. 9B SEC data for Try-OEG with and without DTT treatment.
Figure 9C:
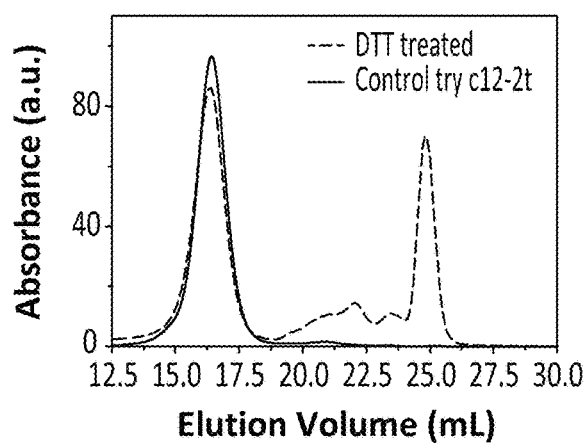
FIG. 9C SEC data for Try-OEG-C12-2T with and without DTT treatment.
Figure 10A:
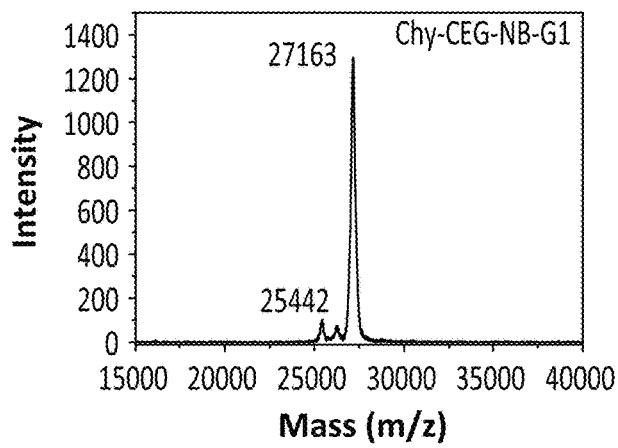
FIG. 10A depicts purification and characterization data for Chy-CEG-NB-G1, showing the MALDI-ToF MS spectrum of the reaction mixture.
Figure 10B:
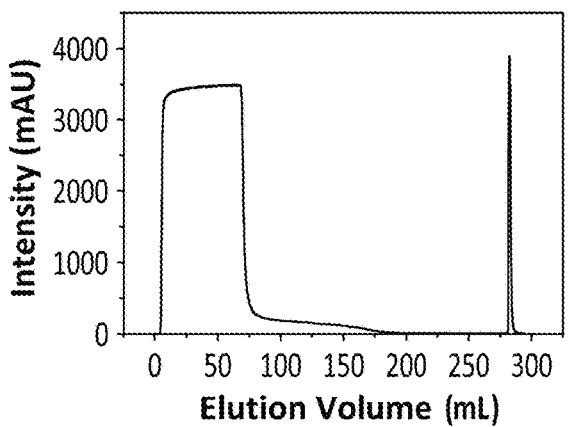
FIG. 10B depicts purification and characterization data for Chy-CEG-NB-G1, using Ion exchange chromatography.
Figure 10C:
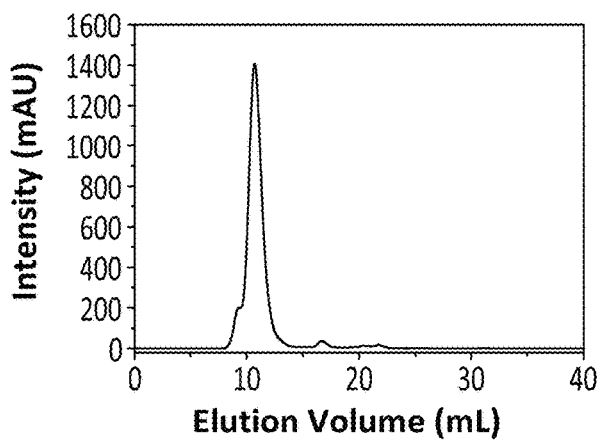
FIG. 10C depicts purification and characterization data for Chy-CEG-NB-G1, using size exclusion chromatography.
Figure 10D:
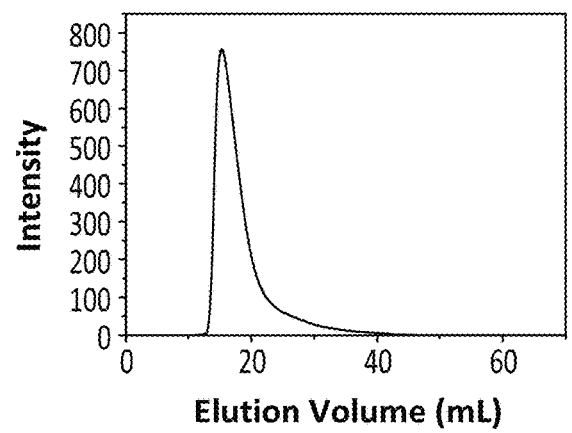
FIG. 10D depicts purification and characterization data for Chy-CEG-NB-G1, using desalting chromatography.
Figure 10E:
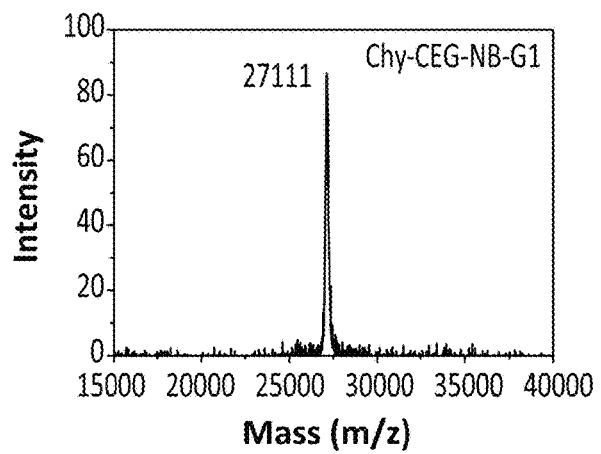
FIG. 10E depicts purification and characterization data for Chy-CEG-NB-G2, showing the MALDI-ToF MS spectrum of the purified conjugate.
Figure 11A:
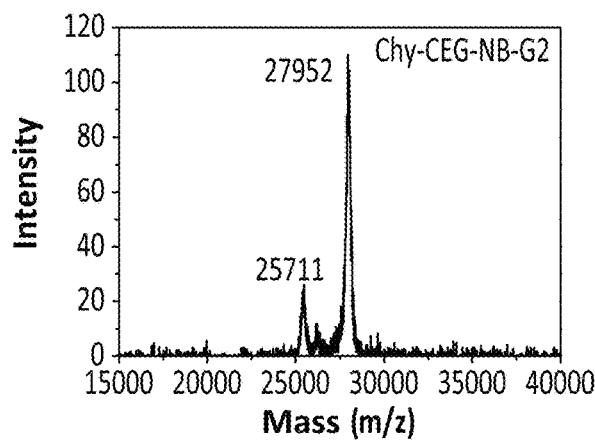
FIG. 11A depicts purification and characterization data for Chy-CEG-NB-G2, showing the MALDI-ToF MS spectrum of the reaction mixture.
Figure 11B:
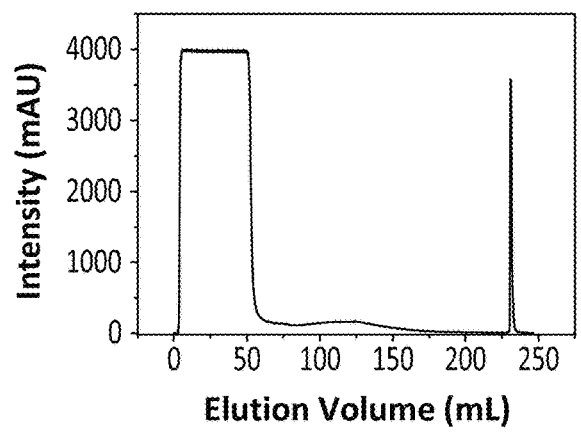
FIG. 11B depicts purification and characterization data for Chy-CEG-NB-G2, using Ion exchange chromatography.
Figure 11C:
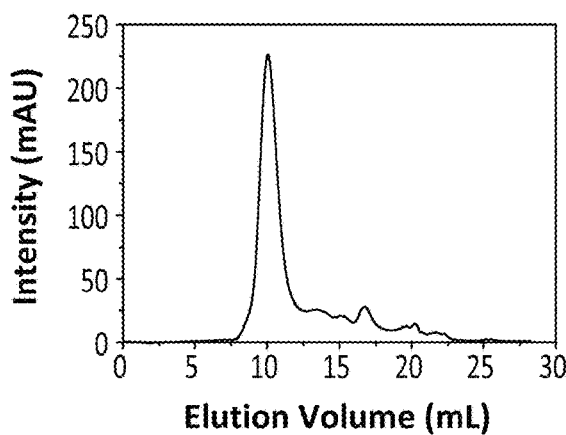
FIG. 11C depicts purification and characterization data for Chy-CEG-NB-G2, using size exclusion chromatography.
Figure 11D:
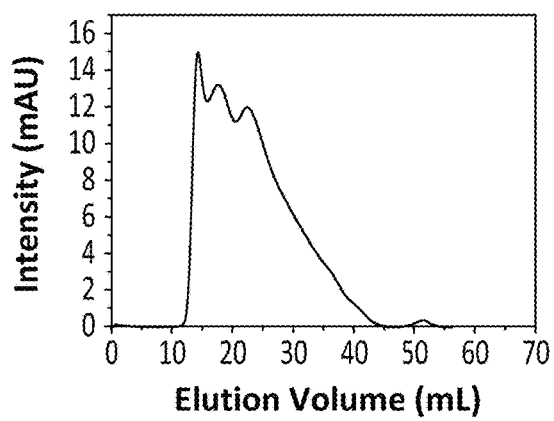
FIG. 11D depicts purification and characterization data for Chy-CEG-NB-G2, using desalting chromatography.
Figure 11E:
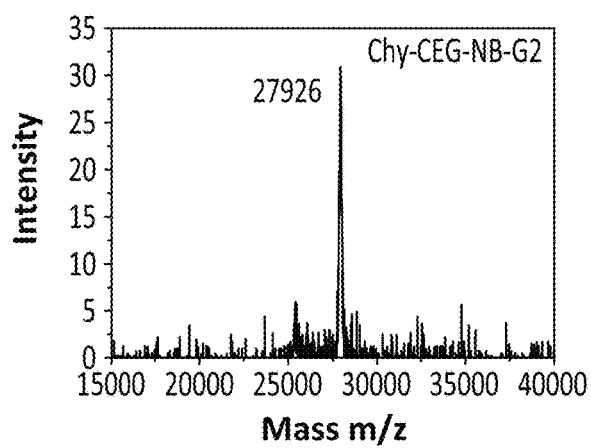
FIG. 11E depicts purification and characterization data for Chy-CEG-NB-G2, showing the MALDI-ToF MS spectrum of the purified conjugate.
Figure 12A:
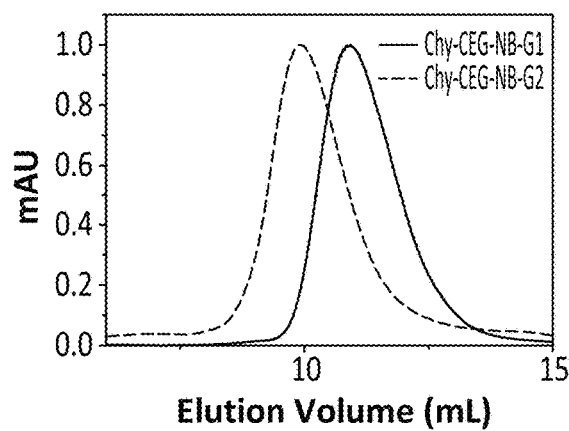
FIG. 12A depicts Self-assembly data of Chy-CEG-NB-G1& G2, using SEC data.
Figure 12B:
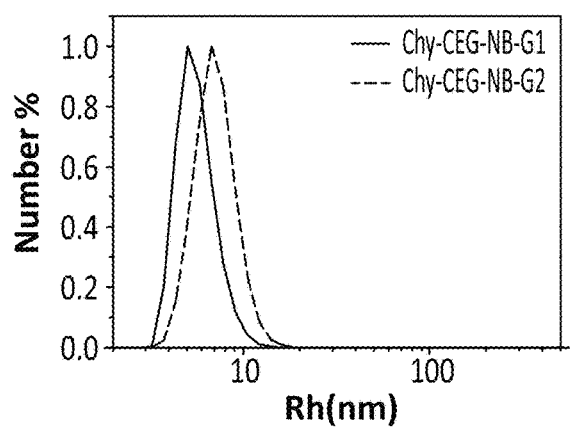
FIG. 12B depicts Self-assembly data of Chy-CEG-NB-G1& G2, using DLS data.
Figure 12C:
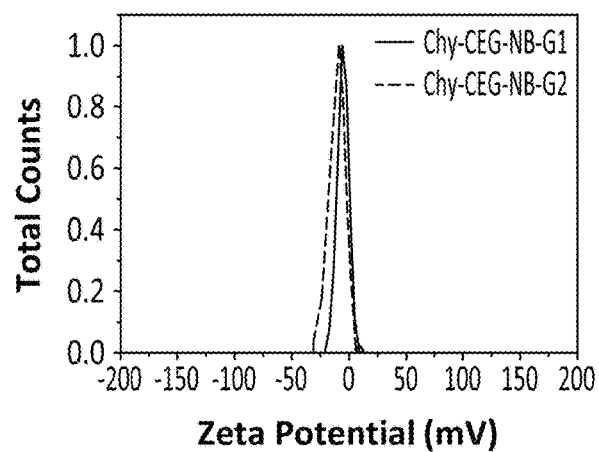
FIG. 12C depicts Self-assembly data of Chy-CEG-NB-G1& G2, using Zeta potential data.
Figure 13A:
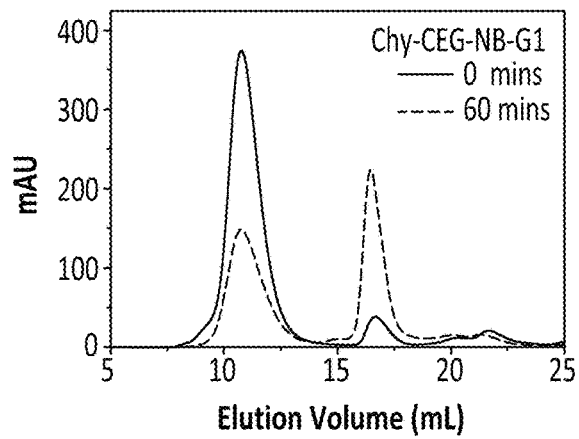
FIG. 13A depicts Partial Dis-assembly SEC data of Chy-CEG-NB-G1.
Figure 13B:
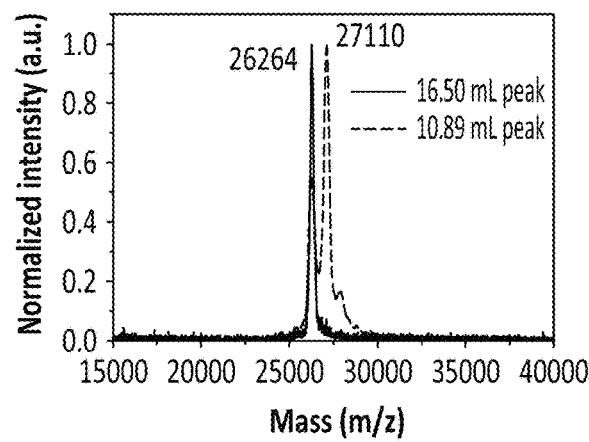
FIG. 13B depicts MALDI-ToF data for Chy-CEG-NB-G1 cleavage.

The sample was dissolved in 50 mM sodium phosphate pH: 7.4 in a beaker and temperature was maintained using ice bath during entire reaction. The sample was exposed to the Sankyo Denki G8T5E UVB linear lamp (1.6×5=8 W output) which emits ultraviolet rays between 280 nm and 360 nm (peak at 305 nm-315 nm). Samples were withdrawn from the beaker from time to time using a pipette and analysis of the same was carried out using SEC. The irradiation studies were carried out for 90 mins. The analytical SEC, shown in FIG. 13A, showed two peaks, the elution volume of the first peak corresponds to the complex and second peak corresponds to the cleaved protein. The MALDI-TOF analysis of two peaks, shown in FIG. 13B, showed that the first peaks matches to the molecular weight of conjugate while the second peak corresponds to the cleaved protein.

Multi-Sensitive Protein Complex (Chy-CEG-NB-G1)

Figure 13C:
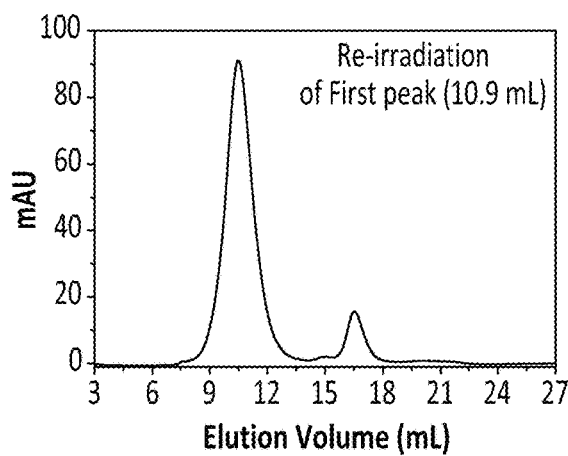
FIG. 13C depicts SEC chromatogram of photo-chemical re-irradiation of first peak after dis-assembly (10.9 mL).
Figure 13D:
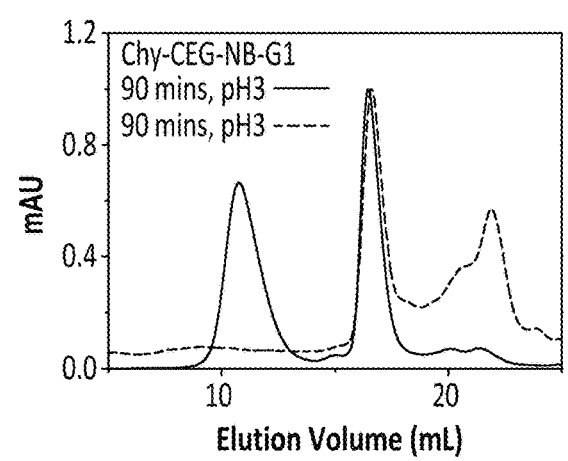
FIG. 13D depicts Overlay SEC chromatogram of photo-chemical irreversible dis-assembly of Chy-CEG-NB-G1 at pH 3 and pH 7.4 (blue).
Figure 14:
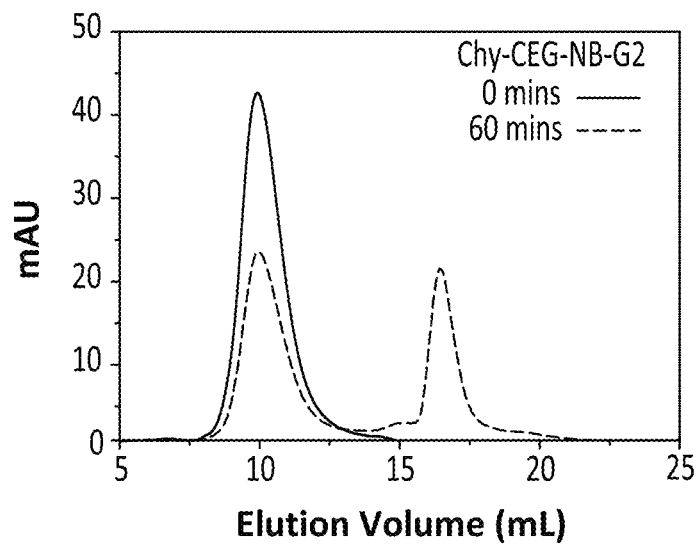
FIG. 14 depicts Partial Dis-assembly data of Chy-CEG-NB-G2.

When the first peak was re-irradiated under the same condition, no cleavage was observed, as seen in FIG. 13C. This showed that the complex eluting at 10.9 mL is not the photo-sensitive complex. Further, it was hypothesized that under photochemical reaction due to the close vicinity, cleaved protein with amine might react to the formed aldehyde and would form imines. To block the imine formation the irradiation studies were carried out at pH 3. The SEC data showed the single peak corresponding to the cleaved protein, shown in FIG. 13D. This suggested that the imine formation was suppressed at pH 3, hence the completed cleavage was observed. The complete cleavage of the complex needed two triggers, i.e. light and acidic medium. The said multi-stimuli protein conjugate does not need the two different stimuli-sensitive chemical moieties to respond to two different stimuli.

Synthesis of Multi Stimuli-Sensitive Probe

The process for synthesis of multi-stimuli macromolecular amphiphilic probe (AABP) (19'f or 20'f) comprises;
  (i) alkylation of G1 or G2 bromide with 5-hydroxy-2-nitrobenzaldehyde in presence of base and solvent to obtain aldehyde (19'a or 20'a) which is reduced to alcohol (19'b or 20'b);
  (ii) activating the alcohol step (i) with N,N'-Disuccinimidyl carbonate in base and solvent to give activated ester (19'c or 20'c);
  (iii) reacting the ester of step (ii) with amine terminated cetyl oligoethylene spacer (Iii) to give diphosphonate ester (19'd or 20'd);
  (iv) converting diphosphonate ester of step (iii) to monophosphonate (19'e or 20'e) and fluorinating with DAST to yield fluorinated compound (19'f or 20'f).

The process is shown in Scheme 11 below:

Scheme 11

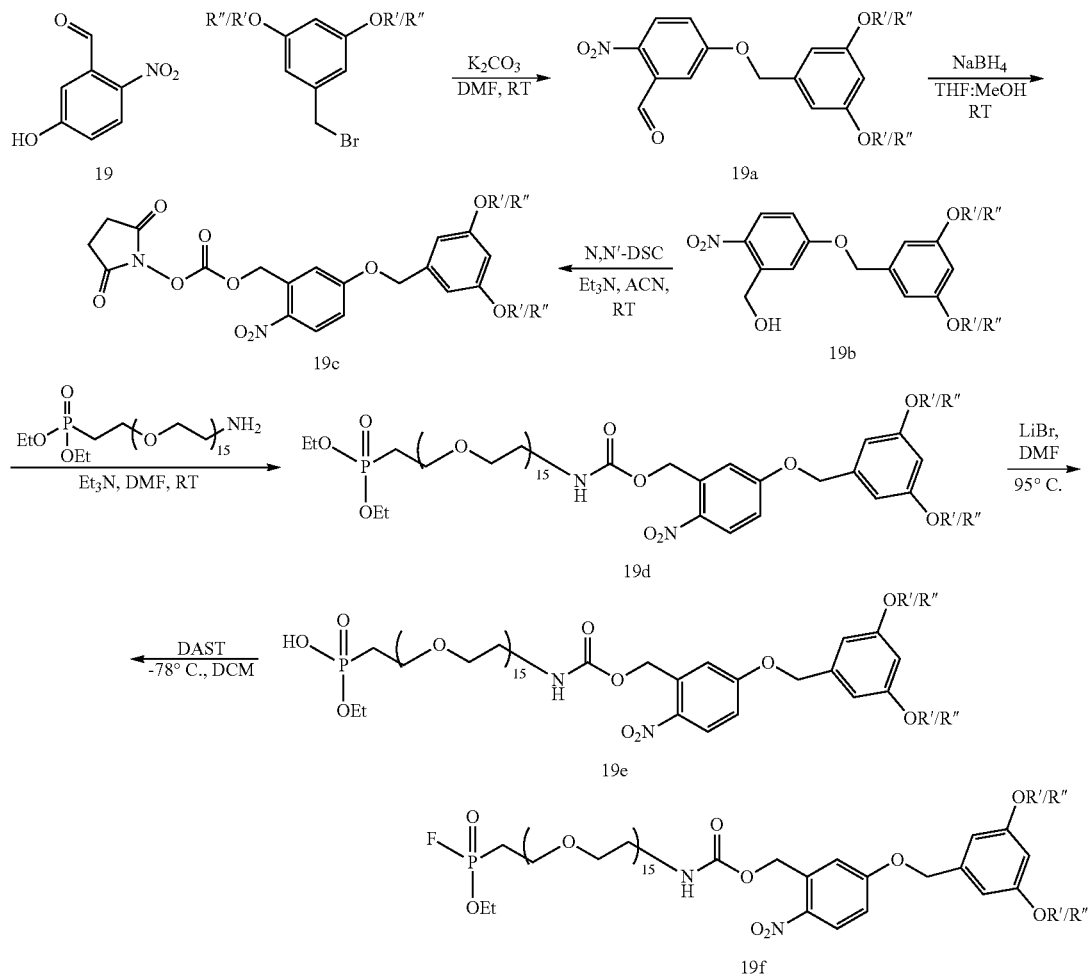

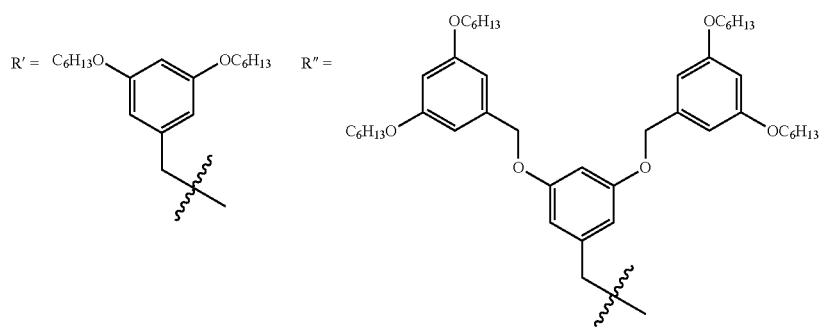

According to Scheme 11, the step (1) comprises alkylating 5-hydroxy-2-nitrobenzaldehyde with the dendrimer G1 bromide in organic solvent at r.t. until completion of the reaction. To the product was added water and extracted in solvent. The combined organic layers were dried and evaporated to get the crude aldehyde (19'a or 20'a) which was further purified. The aldehyde (19'a) was dissolved in THF: MeOH (2:1) under stirring. The mixture was cooled to 0° C. and alkali borohydride such as $NaBH_4$ was added in small portions and allowed to react for about an hour. Upon completion, reaction was quenched with inorganic base such as alkali or alkali metal bicarbonate and extracted with polar organic solvent. The combined organic layer was dried, concentrated under vacuum to get crude alcohol (19'b or 20'b) which was purified.

In step (2), the alcohol was activated by adding N,N'-DSC and dissolving in polar organic solvent under stirring. The organic base selected from triethylamine, ethylamine, pyridine and such like was added slowly at r.t. and allowed to react for about 12 hrs. Upon completion of reaction, the base and the solvent were evaporated under vacuum and the residue was purified to obtain activated ester (19'c or 20'c).

In step (3), the activated ester (19'c or 20'c) and amine terminated cetyl oligoethylene spacer (6m) were dissolved in the solvent under stirring followed by adding the base and stirring for about 12 hrs. Upon completion of reaction, the base and the solvent were evaporated under vacuum. To the obtained residue water was added and extracted with the solvent. Combined organic layer was dried, concentrated under vacuum to get crude diphosphonate ester (19'd or 20'd which was purified.

To the diphosphonate ester (19'd or 20'd), in step 4, was added LiBr followed by addition of the solvent and the mixture was heated at a temperature range of 80-100° C. for about 20 hrs. Upon completion, water was added and extracted with the solvent. The water layer was collected and 2N HCl was added and stirred for another 30-40 minutes and further extracted with solvent. Combined organic layer was dried, concentrated under vacuum to get crude monophosphate (19'e or 20'e) which was used without purification.

To the stirring solution of above obtained monophosphonate ester (19'e or 20'e), the solvent, DAST was added dropwise at about −78° C. and allowed to react for about 15 minutes. Upon completion of reaction, excess of DAST and the solvent were evaporated under vacuum. To the obtained residue, water was added and stirred for about 2 more minutes to quench any residual DAST. Reaction mixture was then extracted with the organic solvent and the combined organic layer was dried, concentrated under vacuum, to get crude AABP probe (19'f or 20'f) which was used without purification.

Synthesis of Amine Terminated Cetyl Ethylene Glycol

In another embodiment, the process for synthesis of amine terminated cetyl ethylene glycol (6m) comprises the following steps;
(i) reacting a mixture of mono benzyl teraethylene glycol (6b) and tosylated-trityl tetraethylene glycol (6a) in presence of base and solvent to obtain Trityl O-(OEG)$_7$ benzyl compound (6c);
(ii) reacting mixture of Trityl O-(OEG)$_7$ benzyl compound (6c) with p-toulenesulfonic acid in alcohol to obtain tosylated compound (6d);
(iii) reacting compound (6d) with tosylated-trityl tetraethylene glycol (6a) in presence of base and solvent to obtain Trityl O-(OEG)$_{11}$ benzyl compound (6e)
(iv) hydrolysing the trirtyl group of compound (6e) with p-toulenesulfonic acid in alcohol to obtain the benzyl 0-(OEG)$_{11}$ alcohol (6f) and reacting with compound (1a) in presence of base and solvent to give TsO-(OEG) is benzyl compound (6f);
(v) reacting compound (6f) with KI in solvent and refluxing to obtain the iodo compound (6h);
(vi) phosphorylating the iodo compound (6h) to obtain diphosphonate ester (6i) followed by reduction to obtain the hydroxyl compound (6j);
(vii) Tosylating hydroxyl compound (6j) in presence of base and solvent to yield tosylated diphosphonate ester (6k);
(viii) Reacting tosylated diphosphonate ester (6k) with sodium azide in solvent to obtain azido compound (6l);
(ix) Reacting azido compound (6l) with Triphenyl phosphine in solvent to 47-amino pentadecaoxaheptatetracontyl)phosphonate(6m).

The process is depicted in Scheme 12 below:

Scheme 12

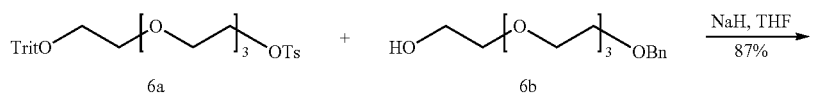

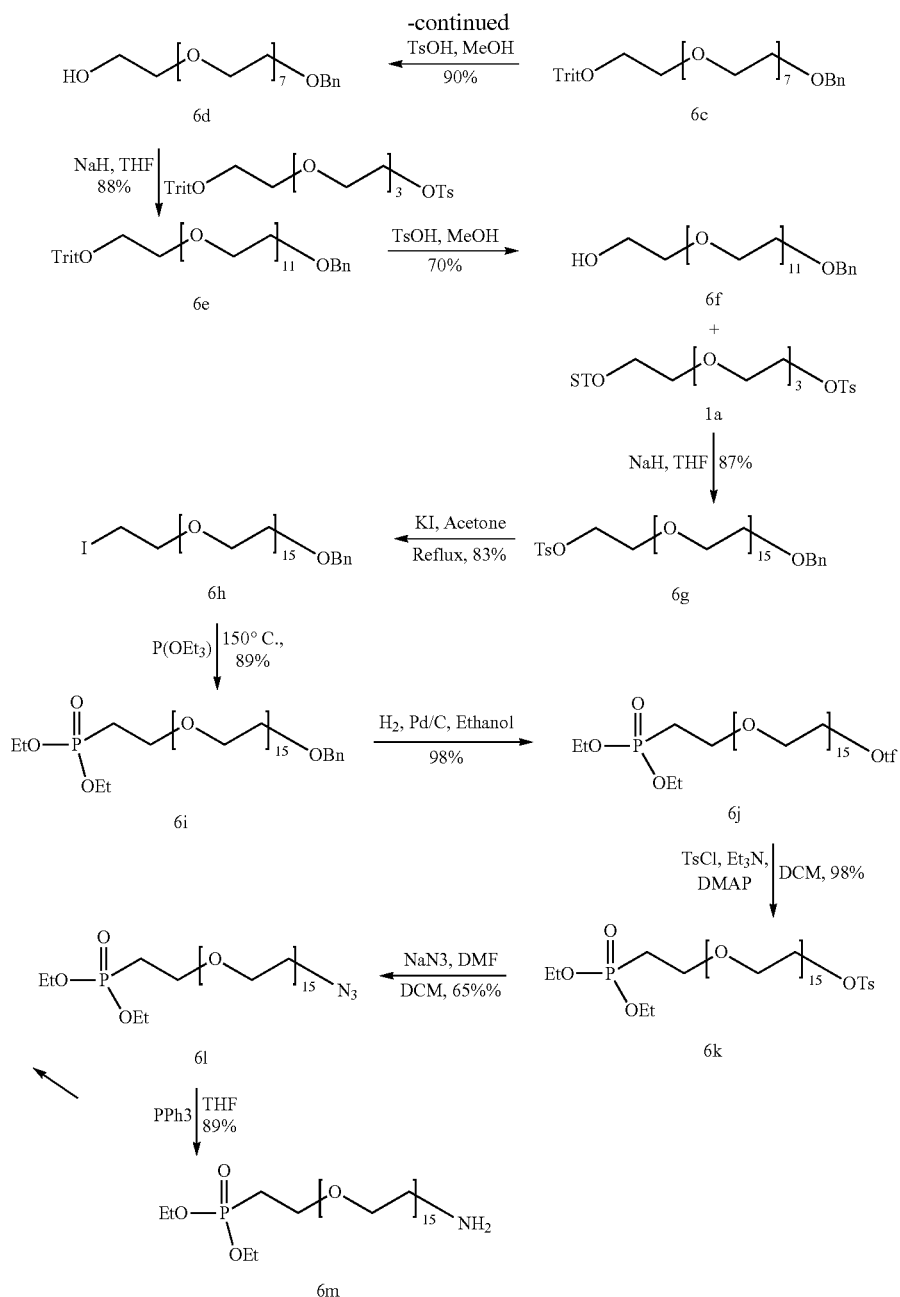

In an embodiment, the stimuli-sensitive protein conjugate of general formula (IA), which can make supramolecular assembly, comprises;
(a) photo-sensitive nitrobenzyl functionalized oligoethylene glycol (OEG) probe which disassembles irreversibly on exposure to light;
(b) pH-sensitive hydrazine functionalized oligoethylene glycol (OEG) probe which disassemble reversibly in response to pH change;
(c) redox-sensitive disulfane functionalized oligoethylene glycol (OEG) probe which disassemble with redox stimuli;
(d) multi stimuli-sensitive cetylethylene glycol probe (CEG) which disassemble in response to various stimuli.

In an embodiment for the process of synthesis of stimuli-sensitive protein conjugate of general formula (IA) the solvents are selected from polar or apolar, protic or aprotic solvents such as lower alcohols, ketones, ethers, acetates, esters, ethers, halogenated hydrocarbons, THF, DMSO and the like alone or combination thereof.

The base for the process is selected from organic base such as ethylamine, triethyl amine, pyridine and such like alone or in combination or inorganic base selected from alkali or alkaline earth metal carbonates or bicarbonates alone or combination thereof.

The reducing agent is selected from alkali metal borohydride such as LiAlH4, NaBH4; or the reduction may be carried out in presence of H2, Pd/C and such reducing agent suitable for the reaction.

In another embodiment, the protein conjugate, which make supramolecular protein assembly, of general Formula (IA) comprises;

(a) conjugate of trypsin and photo-sensitive probe selected from 5-((3,5-bis(dodecyloxy)benzyl)oxy)-2-nitrobenzyl(2-(2-(ethoxyfluoro phosphoryl) ethoxy) ethyl) carbamate (IA');
(b) conjugate of trypsin and pH-sensitive probe ethyl (E)-(2-(2-((1-(2-(3,5-bis(dodecyloxy)benzylidene)hydrazine-1-carbonyl)-1H-1,2,3-triazol-4-yl) methoxy) ethoxy) ethyl) phosphonofluoridate (IA");
(c) conjugate of trypsin and redox-sensitive probe 3,3-(ethoxyfluorophosphoryl)-8-oxo-7,13,16,19,22,25,28,31-octaoxa-3,4-dithia-9-azatritriacontyl 3,5-bis(dodecyloxy) benzoate (IA''');
(d) conjugate of chymotrypsin and 5-((3,5-bis((3,5-bis(hexyloxy)benzyl)oxy)benzyl)oxy)-2-nitrobenzyl (47-(ethoxyfluorophosphoryl)-3,6,9,12,15,18,21,24,27,30,33, 36,39,42,45-penta decaoxaheptatetracontyl)carbamate (IA'''')
(e) conjugate of chymotrypsin and 5-((3,5-bis((3,5-bis((3,5-bis(hexyloxy)benzyl)oxy)benzyl)oxy)benzyl)oxy)-2-nitrobenzyl (47-(ethoxyfluorophosphoryl)-3,6,9,12,15,18,21, 24,27,30,33,36,39,42,45-pentadecaoxaheptatetracontyl) carbamate (IA''''').

Significance

In another embodiment, the present invention provides a composition comprising an active pharmaceutical ingredient in association with stimuli-sensitive protein conjugate, which can make supramolecular protein assembly, of Formula (IA) with the particle size in the range of 10-1000 nm and one or more acceptable excipients.

The excipients are selected from binders, diluents, coatings, disintegrants, glidants, sorbents and the like.

In an embodiment, the composition of the present invention comprises;
(i) an active pharmaceutical ingredient in association with stimuli-sensitive protein conjugates that make supramolecular assemblies of general formula (IA); and
(ii) at least one component selected from the group consisting of an excipient, a surfactant, an acid, a base, a buffer system, an inorganic particle, a UV absorber, and a mixture thereof In an embodiment, the protein conjugate which make supramolecular protein assemblies of the present invention are useful in extended release or controlled release or retarded release or sustained release or site specific release of drug in anti-cancer, anti-viral, anti-microbial, anti-diabetic, anti-TB therapies, in drug abuse therapies, for treating dental and periodontal diseases and such like which require long acting drug treatment.

The protein conjugate which make supramolecular protein assemblies of the present invention are effective as nanocarriers in drug delivery with no toxic or adverse effect.

In an embodiment, the design of the protein conjugates, which make supramolecular protein assemblies, of formula (IA) of the present invention disassemble irreversibly in response to exogenous and endogenous stimuli and finds varied industrial application such as in targeted drug delivery which includes small molecules, proteins, peptides, siRNA, mRNA, microRNA and DNA. The constructs could be used for in vivo diagnostics, in biomaterials and synthetic biology.

Further details of the present invention will be apparent from the examples presented below. Examples presented are purely illustrative and are not limited to the particular embodiments illustrated herein but include the permutations, which are obvious as set forth in the description.

Synthesis:

All reagents were obtained commercially unless and otherwise stated. Reactions were performed in an oven dried round bottom flask (RBF) and under nitrogen atmosphere. Air and moisture-sensitive solvents were transferred via syringe. Reactions were monitored by thin layer chromatography (TLC) and developed chromatogram was visualized by Ultraviolet (UV) lamp or by phosphomolybdic acid (PMA) staining. Product purification was accomplished by 100-200 mesh size silica gel column chromatography.

All the compounds were characterized by $^1$H, $^{13}$C and $^{19}$F (in case of fluorinated compounds) nuclear magnetic resonance (NMR) using bruker or Jeol 400 MHz. $^1$H and $^{19}$F were recorded at an operating frequency of 400 MHz and 100 MHz for $^{13}$C using, using TMS as an internal standered. All the $^{13}$C Chemical shifts were mentioned in parts per million (PPM) and measured relative to residual $CHCl_3$ in deuterated solvent. Coupling constants were reported in Hertz (Hz). Multiplicities were explained as s=singlet, d=doublet, t=triplet, q=quartet, dd=doublet of doublet, ddd=doublet of doublet of a doublet, dt=doublet of triplet, m=multiplet, br=broad, quint=quintet. Mass spectra were obtained with either the MALDI-TOF MS or HRMS. Room temperature varied between 21-35° C.

Some General Procedures

General Procedure for Synthesis of Iodide—Procedure A

A mixture of above obtained tosylate (1.0 eq) and KI (4.0 eq) was refluxed in acetone for 18 h. Upon completion, excess KI was filtered and washed thrice with acetone. Collected acetone fraction was evaporated under vacuum to get residue, which was then washed with water and extracted with DCM. The combined organic layer was washed with aqueous $Na_2CO_3$ and then concentrated under vacuum to get crude product which was purified by silica gel column chromatography using MeOH/DCM as eluent.

General Procedure for Synthesis of Diphosphonate Ester—Procedure B

In an oven dried RBF, iodide (1.0 eq) and $P(OEt)_3$ (4.0 eq) were taken and refluxed for 1 h. Upon completion of reaction, the excess $P(OEt)_3$ was removed under vacuum and the reaction mixture was directly loaded onto a silica gel column and crude mixture was purified using MeOH/DCM as eluent.

General Procedure for Synthesis of Alcohol—Procedure C

In an oven dried RBF, a mixture of diphospohonate ester (1 eq) and TsOH (5 eq) was dissolved in MeOH and stirred for 12 h at RT. Upon completion of reaction, solvent was evaporated under reduced pressure. Then, the obtained residue purified using silica gel column chromatography using MeOH/DCM as eluent.

General Procedure for Synthesis of Tosylate—Procedure D

In an oven dried RBF, above obtained alcohol (1 eq), TsCl (3 eq), DMAP (1 eq) were taken and was dissolved in DCM under at 0° C. Then, $Et_3N$ (4 eq) was added to the above mixture and allowed to stir for 12 h at RT. Upon completion, the reaction was quenched with water and extracted in DCM for thrice. The combined organic layer was dried over $Na_2SO_4$ and concentrated under reduced pressure to get crude product which was purified using silica gel column chromatography using MeOH/DCM as eluent.

General Procedure for Synthesis of Azide—Procedure E

In an oven dried RBF, above obtained tosylate (1 eq) and $NaN_3$ (10 eq) was taken and dissolved in DMF under stirring. The resultant mixture was allowed to react for 12 h. Upon completion of reaction, DMF was evaporated under reduced pressure. Then, the obtained residue was purified using silica gel column chromatography using MeOH/DCM as eluent.

General Procedure for Synthesis of Amine—Procedure F In an oven dried RBF, azide (1 eq) was taken and dissolved in THF under stirring. Then, PPh$_3$ (1.5 eq) was added to the above mixture at 0° C. and allowed to react for 18 h at RT. Upon completion of reaction, few drops of water was added and again stirred for 1 hour. Then, THF was evaporated under reduced pressure and the obtained water layer was washed with toluene for at least four times. The water layer was then, concentrated under reduced pressure to get product which was used without further purification.

Procedure for Synthesis of Aldehyde—Procedure G

In an oven dried RBF, 5-hydroxy-2-nitrobenzaldehyde (1.1 eq), K$_2$CO$_3$ (1.1 eq) and bromide (1 eq) were dissolved in DMF under stirring at RT and allowed to react for 12 h. Upon completion of reaction, water was added and extracted thrice with DCM. The combined organic layer was dried over Na$_2$SO$_4$ and evaporated under vacuum to get crude product which was purified using silica gel column chromatography using EtOAc/hexane as eluent.

Procedure for Synthesis of Alcohol—Procedure H

In an oven dried RBF, above obtained aldehyde (1 eq) was dissolved in THF:MeOH (2:1) under stirring. Then, the mixture was cooled to 0° C. and NaBH$_4$ (1.5 eq) was added in small portions and allowed to react for 1 hour. Upon completion, reaction was quenched with Na$_2$CO$_3$ and extracted thrice with EtOAc. The combined organic layer was dried over Na$_2$SO$_4$ and concentrated under vacuum to get crude product which was purified using silica gel column chromatography using EtOAC/hexane as eluent.

Procedure for Synthesis of Activated Ester—Procedure I

In an oven dried RBF, above obtained alcohol (1 eq) and N,N'-DSC (5 eq) were dissolved in ACN under stirring. Then, Et$_3$N (5 eq) was then added slowly at RT and allowed to react for 12 h. Upon completion of reaction, ACN and Et$_3$N were evaporated under vacuum. The obtained residue was directly purified using silica gel column chromatography using EtOAc/hexane as eluent.

Procedure for Synthesis of Diphosphonate Ester—Procedure J

In an oven dried RBF, above obtained activates ester (1.1 eq) and compound 26g (1 eq) were dissolved in DMF under stirring. Then, Et$_3$N (1.1 eq) was added slowly to the reaction mixture and stirred at RT for 12 h. Upon completion of reaction, DMF and Et$_3$N were evaporated under vacuum. To the obtained residue water was added and extracted thrice with DCM. Combined organic layer was dried over Na$_2$SO$_4$ and concentrated under vacuum to get crude product which was purified using silica gel column chromatography using silica gel column chromatography using MeOH/DCM as eluent Procedure for Synthesis of Monophosphonate Ester—Procedure K In an oven dried RBF, above obtained diphosphonate ester (1 eq) was taken and LiBr (20 eq) was added. To the mixture, DMF was added and heated at 95° C. for 20 h. Upon completion, water was added and extracted thrice with EtOAc. The water layer was collected and 2N HCl was added and stirred for another 30 minutes. The mixture was then extracted thrice with EtOAc. Combined organic layer was dried over Na$_2$SO$_4$ and concentrated under vacuum to get crude product which was used without purification.

Procedure for Synthesis of Flurophosphonate Ester—Procedure L

To the stirring solution of above obtained monophosphonate ester (1 eq) in DCM, DAST (4 eq) was added dropwise at −78° C. and allowed to react for 15 minutes. Upon completion of reaction, excess of DAST and DCM were evaporated under vacuum. To the obtained residue, water was added and stirred for 2 more minutes to quench any residual DAST. Reaction mixture was then extracted thrice with DCM. Combined organic layer was dried over Na$_2$SO$_4$ and concentrated under vacuum to get crude product which was used without purification.

General Procedure for Synthesis of Monotrityloligoethylene Glycol—Procedure M

In an oven dried RBF, monobenzyl oligoethylene glycol (1 eq) and tosyl tetraethylene glycol (2 eq) was dissolved in THF under stirring. Then, sodium hydride (NaH) (4 eq) was added in a small portion at 0° C. The reaction was allowed to react for 12 hours at RT. Upon completion, excess of NaH was quenched by dropwise addition of water, and reaction mixture was extracted with DCM for thrice. Combined organic layer was dried over sodium sulphate (NaSO$_4$) and on concentrated under reduced pressure to get the crude residue, which was purified using silica gel column chromatography.

General Procedure for Synthesis of Trityl Deprotection—Procedure N

In an oven dried RBF, mixture of monotrityl oligoethylene glycol (1 eq) and p-toulenesulfonic acid (TsOH) (1.5 eq) was taken and dissolved in methanol under stirring. The mixture was allowed to react for 12 hours at RT. Upon completion, methanol was evaporated under reduced pressure. To the obtained residue water was added and extracted thrice in DCM. Combined organic layer was dried over sodium sulphate (NaSO$_4$) and on concentrated under reduced pressure to get the crude residue, which was purified using silica gel column chromatography.

General Procedure for the Synthesis of G0-G2 Bromide—Procedure O

In an oven dried RBF, alcohol and tetrabromomethane (CBr$_4$) were taken and dissolved in DCM. Then solution of triphenylphosphine (PPh$_3$) in DCM was added drop wise at 0° C. and allowed to stir for 3 hours at RT. Upon completion of reaction, DCM was evaporated under reduced pressure. Obtained residue was directly purified using silica gel column chromatography.

General Procedure for the Synthesis of G1-G2 Alcohol—Procedure P

In an oven dried RBF bromide, 3, 5dihydroxybenzyl alcohol, potassium carbonate (K$_2$CO$_3$) and crown ether (18-crown-6) were taken. The resulting mixture was refluxed for 36 hours. Upon completion, reaction mixture was cooled to RT. Then acetone was evaporated under reduced pressure. To the obtained residue water was added and extracted with DCM thrice. Combined organic layer was dried over Na$_2$SO$_4$ and concentrated under reduced pressure to get crude product which was purified using silica gel column chromatography.

Example 1. Synthesis of Photo-Sensitive Supramolecular Protein Conjugate (IA')

Example 1.1 Synthesis of Amine Terminated Octa Ethylene Glycol Spacer

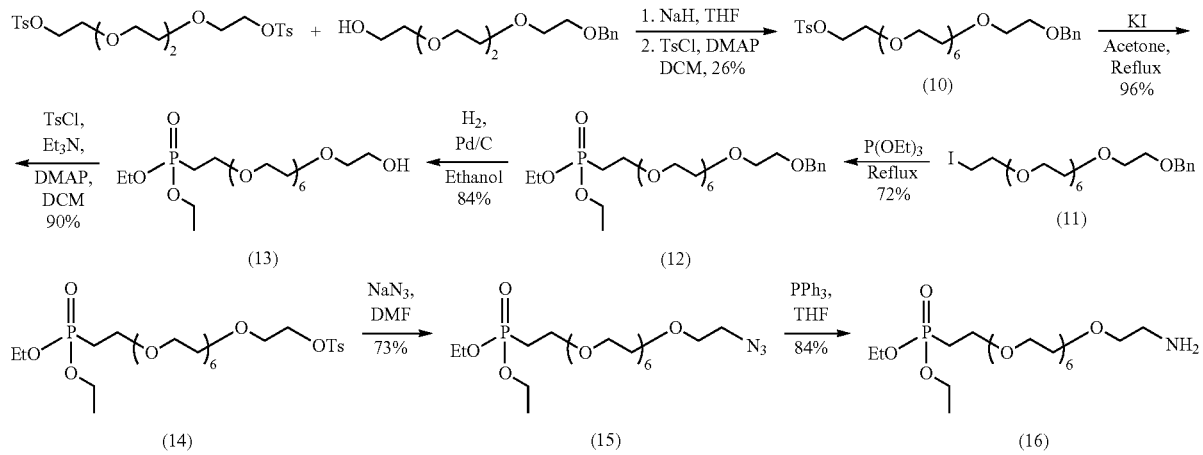

Procedures for Synthesis of Individual Molecules

1.1.1: Synthesis of 2-(2-(2-(benzyloxy)ethoxy)ethoxy)ethyl 4-methylbenzenesulfonate (10)

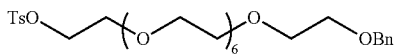

A mixture of ditosyltetraethylene glycol(42 g, 1.2 eq) and monobenzyltetraethylene glycol(14 g, 0.7 eq) was dissolved under stirring at 0° C. in THF. Then NaH (4.0 g, 1.2 eq) was added in portions. The reaction was stirred for 12 hours at RT. Upon completion of reaction excess of NaH was quenched by drop wise addition of water and extracted with DCM thrice. The combined organic layer was dried over $Na_2SO_4$ and concentrated under vacuum.

To the obtained residue, tosyl chloride and DMAP was added in an oven dried RBF. Then Triethyl amine was added and allowed to react for 12 hours at RT under stirring. Upon completion, water was added to the reaction and extracted with DCM thrice. The combined organic layer was dried over $Na_2SO_4$ and concentrated under vacuum to get crude product which was purified using silica gel column chromatography using MeOH/DCM as eluent to get pale yellow liquid. Yield (3.6 g, 26%) $^1$H NMR (400 MHz, $CDCl_3$): $\delta_H$ 7.78 (d, J=8 Hz, 2H), 7.33-7.26 (m, 7H), 4.56 (s, 2H), 4.15 (t, J=4.8 Hz, 2H), 3.69-3.55 (m, 32H), 2.44 (s, 3H). $^{13}$C NMR (100 MHz, $CDCl_3$): $\delta_c$ 144.95, 133.06, 129.95, 127.97, 77.16, 70.83, 70.64, 69.38, 68.78, 21.75. MALDI-TOF MS: (M+K) 653.48.

1.1.2: Synthesis of ((2-(2-(2-iodoethoxy)ethoxy)ethoxy)methyl)benzene (11)

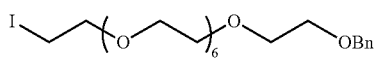

A mixture of above obtained tosylate (2.4 g, 1.0 eq) and KI (3.8 g, 4.0 eg) was refluxed in acetone for 18 hours. Upon completion, excess KI was filtered and washed thrice with acetone. Collected acetone fraction was then evaporated under vacuum to get residue, which was then washed with water and extracted with DCM. The combined organic layer was washed with aqueous $Na_2CO_3$ and then concentrated under vacuum to get crude product which was purified using silica gel column chromatography using MeOH/DCM as eluent to get pale yellow liquid Yield (2.1 g, 96%). $^1$H NMR (400 MHz, $CDCl_3$): $\delta_H$ 4.56 (s, 2H), 4.15 (t, J=4.8 Hz, 2H), 3.69-3.55 (m, 32H), 2.44 (s, 3H). $^{13}$C NMR (100 MHz, $CDCl_3$): $\delta_c$ 144.95, 133.06, 129.95, 127.97, 77.16, 70.83, 70.64, 69.38, 68.78, 21.75. MALDI-TOF MS: (M+K) 609.42.

1.1.3: Synthesis of Diethyl (2-(2-(2-(benzyloxy)ethoxy)ethoxy)ethyl)phosphonate (12)

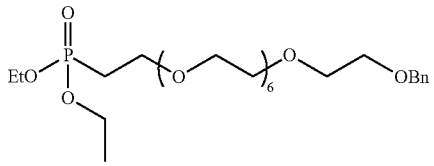

In an oven dried RBF, above obtained iodide (2.5 g, 1.0 eq) and triethylphosphite, $P(OEt)_3$ (2.7 g, 4.0 eg) were taken and refluxed for 1 hour at 150° C. Upon completion of reaction, the excess $P(OEt)_3$ was removed under vacuum and the reaction mixture was directly loaded onto a silica gel column and crude mixture was purified using MeOH/DCM as eluent to get pale yellow liquid. Yield (1.9 g, 72%). $^1$H NMR (400 MHz, $CDCl_3$): $\delta_H$ 7.29-7.22 (m, 5H), 4.55 (s, 2H), 4.14-4.01 (m, 4H), 3.75-3.57 (m, 34), 2.16-2.05 (m, 2H), 130 (t, J=7.2 Hz, 6H). $^{13}$C NMR (100 MHz, $CDCl_3$): $\delta_C$1440.95, 133.06, 129.95, 127.97, 77.16, 70.83, 70.64, 69.38, 68.78, 21.75. MALDI-TOF MS: (M+K) 619.18.

1.1.4: Synthesis of Diethyl (2-(2-(2-hydroxyethoxy)ethoxy)ethyl)phoshonate (13)

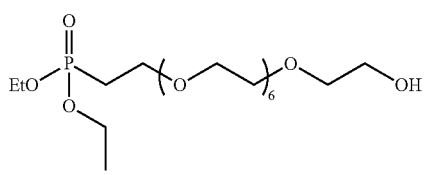

In an oven dried RBF, diphosphonate ester (1.4 g, 1 eq) was taken dissolved in ethanol. Pd/C was added under stirring. The resultant mixture was stirred under hydrogen for 18 hours. Upon completion, the mixture was filtered through cilite and washed with ethanol thrice. The filtrate was concentrated under vacuum to get crude mixture and used for next step without purification. Yield (1.0 g, 84%) $^1$H NMR (400 MHz, CDCl$_3$): $\delta_H$ 4.55 (s, 2H), 4.14-4.01 (m, 4H), 3.75-3.57 (m, 34), 2.16-2.05 (m, 2H), 130 (t, J=7.2 Hz, 6H). MALDI-TOF MS: (M+K) 529.33.

1.1.5 Synthesis of 2-(2-(2-(diethoxyphosphoryl)ethoxy)ethoxy)ethyl 4-methylbenzenesulfonate (14)

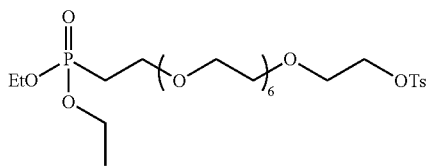

In an oven dried RBF, alcohol (0.49 g, 1.0 eq), DMAP (0.021 g, 0.5 eq) and tosyl chloride (0.34 g, 2.5 eq) was taken and dissolved in DCM with stirring. Mixture was cooled to 0° C. and triethyl amine (0.56 mL, 4 eq) was added drop wise. The resultant mixture was then stirred for 12 hours at RT. Upon completion, reaction was quenched by dropwise addition of water and extracted thrice with DCM. Combined organic layer was dried over Na$_2$SO$_4$ and concentrated under vacuum to get a crude product, which was purified using silica gel column chromatography using MeOH/DCM as eluent to get pale yellow liquid. Yield (0.58 g, 90%). $^1$H NMR (400 MHz, CDCl$_3$): $\delta_H$ 7.78 (d, J=8 Hz, 2H), 7.33-7.26 (m, 7H), 4.56 (s, 2H), 4.15 (t, J=4.8 Hz, 2H), 3.69-3.55 (m, 32H), 2.44 (s, 3H). MALDI-TOF MS: (M+K) 683.33.

1.1.6: Synthesis of Diethyl (2-(2-(2-azidoethoxy)ethoxy)ethyl)phosphonate (15)

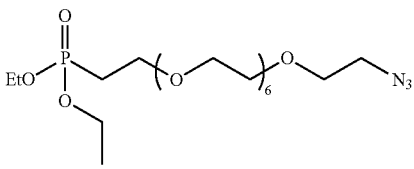

To the mixture of above obtained tosyl (0.58 g, 1.0 eq) and sodium azide (NaN$_3$) (0.29 g, 1.5 eq) in an oven dried RBF, DMF was added and stirred for 12 hours at RT. Upon completion, water was added to the reaction mixture and extracted thrice with ethyl acetate. Combined organic layer was dried over Na$_2$SO$_4$ and concentrated under vacuum to get crude product which was purified using MeOH/DCM as eluent to get pale yellow liquid. Yield (0.41 gm, 73%). $^1$H NMR (400 MHz, CDCl$_3$): $\delta_H$ 4.55 (s, 2H), 4.14-4.01 (m, 4H), 3.75-3.57 (m, 34H), 2.16-2.05 (m, 2H), 130 (t, J=7.2 Hz, 6H).

1.1.7: Synthesis of Diethyl (2-(2-(2-aminoethoxy)ethoxy)ethyl)phosphonate (16)

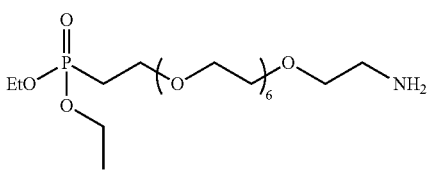

Triphenyl phosphine (0.076 g, 1.5 eq) was added to a solution of azide (0.10 g, 1 eq) in THF at 0° C. The reaction mixture was allowed to warm to room temperature and stirred for 18 hours. Water (10-12) drops was added to the reaction mixture and the solution was allowed to stir for 1 hour. The solvent was concentrated in vacuum. To the obtained residue water was added and washed 6 times with toluene. Then, the water layer was concentrated under reduced pressure to get crude product which was purified using flash column chromatography using MeOH/DCM/Et$_3$N as eluent to get pale yellow liquid. Yield (0.080 gm, 84%). $^1$H NMR (400 MHz, CDCl$_3$): $\delta_H$ 4.55 (s, 2H), 4.14-4.01 (m, 4H), 3.75-3.57 (m, 34), 2.16-2.05 (m, 2H), 130 (t, J=7.2 Hz, 6H). MALDI-TOF MS: (M+K) 528.33.

Example 1.2 Synthesis of Photo-Sensitive Probe (9)

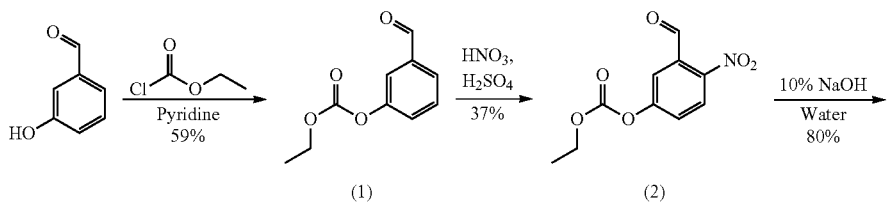

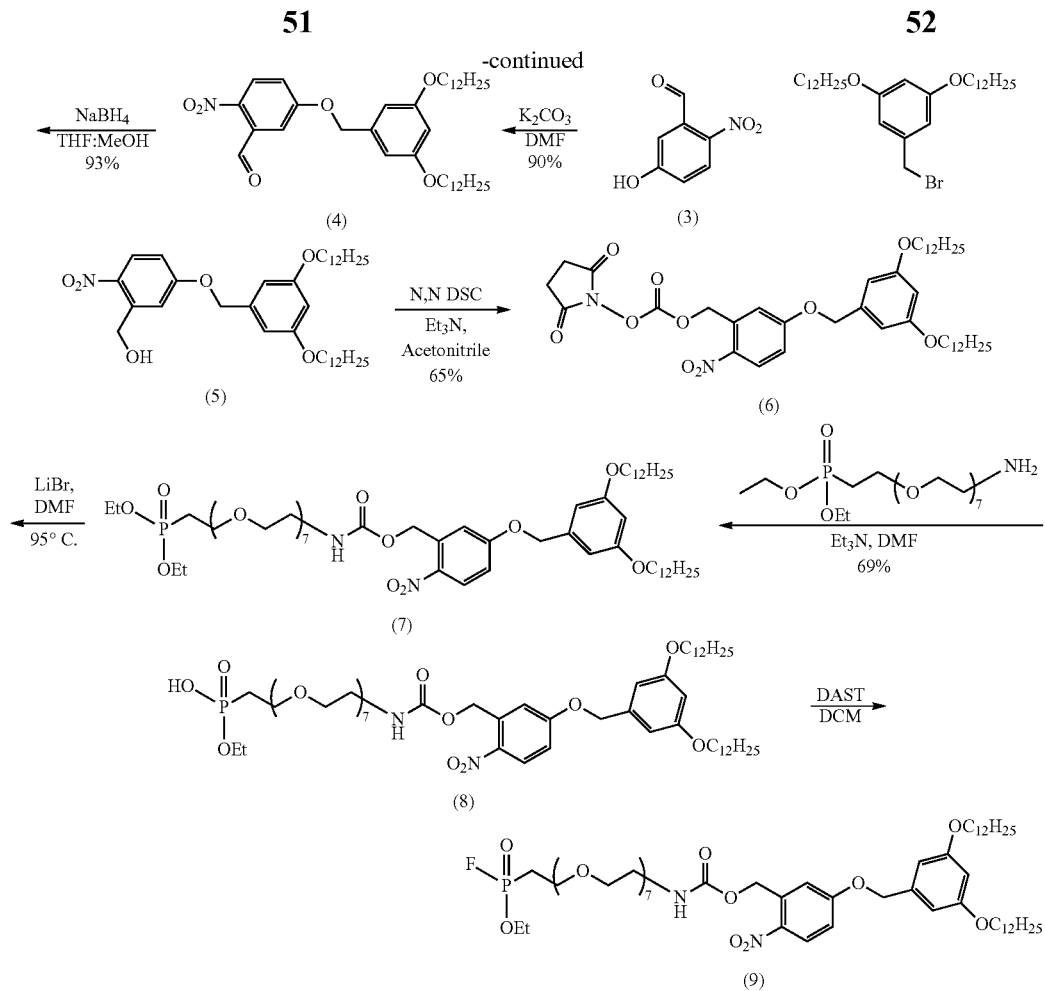

Procedures for Synthesis of Individual Molecules

1.2.1 Synthesis of Ethyl (3-formylphenyl) Carbonate (1)

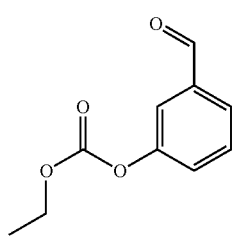

3-hydroxybenzaldehyde (5.9 g, 1 eq) was dissolved in anhydrous pyridine under stirring at 0° C. Then ethyl chloroformate (9.3 mL, 2 eq) was added dropwise over a period of 30 minutes under nitrogen, which results in precipitation of white solid. Then, the reaction was allowed to react for 4 hours at room temperature under stirring, which results in a clear reaction mixture. Then, pyridine was concentrated in vacuum and water was added to the residue. This aqueous layer was extracted thrice with $Et_2O$. The combined $Et_2O$ layers was washed first with 5% aqueous HCl and then with 5% cold and aqueous NaOH. The resulting ether layer was dried ($Na_2SO_4$), filtered and concentrated in vacuum to give analytically pure compound. Yield (5.6 g, 59%). $^1$H NMR (400 MHz, CDCl$_3$): $\delta_H$ 10.03 (s, 1H), 7.79 (dt, J=7.5, 1.3 Hz, 1H), 7.74 (dd, J=2.5, 1.4 Hz, 1H), 7.59 (t, J=7.8 Hz, 1H), 7.47 (ddd, J=8.1, 2.4, 1.1 Hz, 1H), 4.36 (q, J=7.1 Hz, 2H), 1.43 (t, J=7.1 Hz, 3H); $^{13}$C NMR (100 MHz, CDCl$_3$) $\delta_C$ 191.1, 153.35, 151.76, 137.88, 130.31, 127.47, 127.26, 121.88, 65.32, 14.27

1.2.2: Synthesis of Ethyl (3-formyl-4-nitrophenyl) Carbonate (2)

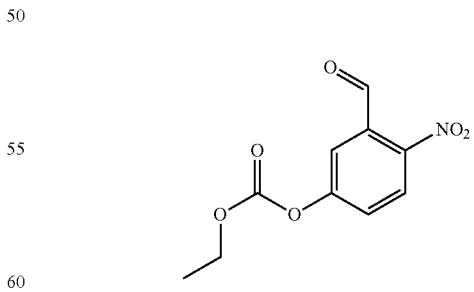

To the above aldehyde (5.6 g, 1 eq), conc. $H_2SO_4$ (55 mL) was added at 0° C. under stirring. Then nitrating mixture (3.57 mL HNO$_3$ (67%) in 18.0 mL conc. $H_2SO_4$) was added dropwise over a period of 30 minutes. Under 0° C., the reaction mixture was allowed to react for 4 hours. Upon completion, the reaction mixture was slowly added to crushed ice. The precipitated, light brown solid was filtered and washed thoroughly with ice cold water during filtration and dried under vacuum to get crude product which was purified using silica gel column chromatography using MeOH/DCM as eluent. Yield (2.5 g, 37%). 1H NMR (400 MHz, CDCl$_3$): $\delta_H$10.25 (s, 1H), 8.40-8.06 (m, 1H), 7.81-7.75 (m, 2H), 4.31 (q, J=7.1 Hz, 2H), 1.32 (t, J=7.1 Hz, 3H). $^{13}$C NMR (100 MHz, CDCl$_3$) $\delta_C$ 189.46, 154.66, 152.4, 146.94, 133.27, 127.2, 126.99, 122.68, 65.94, 14.42

1.2.3: Synthesis of 5-hydroxy-2-nitrobenzaldehyde (3)

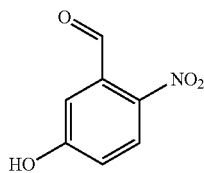 [SMILES: O=Cc1cc(O)ccc1[N+](=O)[O-]]

A solution of ethyl (3-formyl-4-nitrophenyl) carbonate (2.5 g, 1 eq) in 10% aqueous NaOH (23 mL) was stirred at room temperature for 2 hours. This results in a clear brown solution. The reaction mixture was cooled to 0° C. and neutralized with AcOH (approx. 4 mL). The resulting aqueous layer was extracted thrice with Et$_2$O, the combined organic layers was washed with brine (20 mL), filtered and concentrated in vacuum to give brown colored crude product. Purification of crude product by column chromatography (EtOAc/hexane) on silica gel resulted in pure compound. Yield (1.5 g, 80%). $^1$H NMR (400 MHz, CDCl$_3$): $\delta_H$11.39 (s, 1H), 10.27 (s, 1H), 8.12 (d, J=8.9 Hz, 1H), 7.13 (dd, J=8.9, 2.8 Hz, 1H), 7.08 (d, J=2.8 Hz, 1H). $^3$C NMR (100 MHz, CDCl$_3$): $\delta_C$ 190.62, 163.51, 140.93, 135.28, 128.11, 119.65, 115.23.

1.2.4: Synthesis of 5-((3,5-bis(dodecyloxy)benzyl)oxy)-2-nitrobenzaldehyde (4)

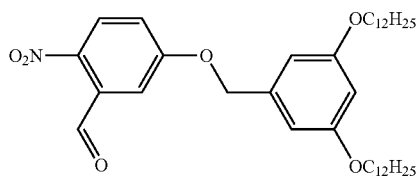

In an oven dried RBF, 5-hydroxy-2-nitrobenzaldehyde (0.11 g, 1 eq), potassium carbonate (0.11 g, 1.2 eq) and bromide (0.40 g, 1.1 eq) were taken and dissolved in DMF under stirring at RT and allowed to react for 24 hours. Upon completion of reaction, water was added and extracted thrice with DCM. The combined organic layer was dried over Na$_2$SO$_4$ and evaporated under vacuum to get crude product which was purified using silica gel column chromatography using EtOAC/hexane as eluent. Yield (0.36 g, 90%). $^1$H NMR (400 MHz, CDCl3): 10.47 (s, 1H), 8.15 (d, J=8.9 Hz, 1H), 7.40 (d, J=8.9, 2.8 Hz, 1H), 7.18 (d, J=2.8 Hz, 1H), 6.52 (d, J=2.4 Hz, 2H), 6.42 (t, J=2.4 Hz, 1H), 5.12 (s, 2H), 3.93 (t, J=6.4 Hz, 4H), 1.85-1.68 (m, 4H), 1.48-1.26 (m, 44H), 0.88 (t, J=7.2 Hz, 6H). $^{13}$C NMR (100 MHz, CDCl$_3$): 188.57, 163.17, 160.82, 142.45, 137.13, 134.40, 127.40, 119.29, 114.50, 105.78, 101.22, 77.16, 71.14, 68.25, 32.04, 29.79, 29.77, 29.73, 29.71, 29.52, 29.48, 29.34, 26.16, 22.82, 14.26.

1.2.5: Synthesis of (5-((3,5-bis(dodecyloxy)benzyl)oxy)-2-nitrophenyl)methanol (5)

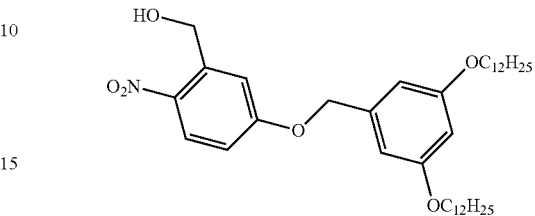

In an oven dried RBF, above aldehyde (0.40 g, 1 eq) was taken and dissolved in THF (2 mL) under stirring. MeOH (0.8 mL) was added slowly to the above solution. Then the mixture was cooled to 0° C. and NaBH$_4$ (0.036 g, 1.5 eg) was added in small portions and allowed to react for 1 hour. Upon completion, reaction was quenched with Na$_2$CO$_3$ and extracted thrice with ethyl acetate. The combined organic layer was dried over Na$_2$SO$_4$ and concentrated under vacuum to get crude product which was purified using silica gel column chromatography using EtOAC/hexane as eluent. Yield (0.37 g, 93%). $^1$H NMR (400 MHz, CDCl3): 8.15 (d, J=8.9 Hz, 1H), 7.40 (dd, J=8.9, 2.8 Hz, 1H), 7.18 (d, J=2.8 Hz, 1H), 6.52 (d, J=2.4 Hz, 2H), 6.42 (t, J=2.4 Hz, 1H), 5.12 (s, 2H), 4.80 (s, 2H), 3.93 (t, J=6.4 Hz, 4H), 1.85-1.68 (m, 4H), 1.48-1.26 (m, 44H), 0.88 (t, J=7.2 Hz, 6H). $^{13}$C NMR (100 MHz, CDCl$_3$): 163.17, 160.82, 142.45, 137.13, 134.40, 127.40, 119.29, 114.50, 105.78, 101.22, 77.16, 71.14, 68.25, 32.04, 29.79, 29.77, 29.73, 29.71, 29.52, 29.48, 29.34, 26.16, 22.82, 14.26.

1.2.6: Synthesis of 5-((3,5-bis(dodecyloxy)benzyl)oxy)-2-nitrobenzyl (2,5-dioxopyrrolidin-1-yl) carbonate(6)

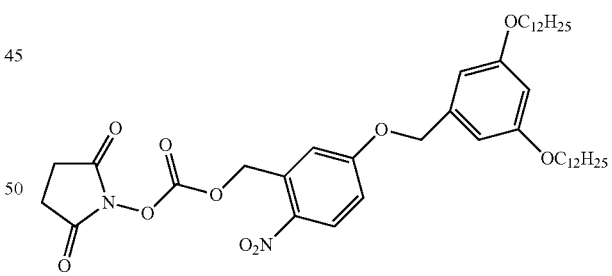

In an oven dried RBF, above alcohol (0.31 g, 1 eq) and N,N'-Disuccinimidyl carbonate (0.63 g, 5 eq) were dissolved in ACN under stirring. Triethyl amine (0.34 mL, 5 eq) was then added slowly at RT and allowed to react for 12 hours. Upon completion of reaction, ACN and triethyl amine was evaporated under vacuum. The obtained residue was purified directly using silica gel column chromatography using EtOAC/hexane as eluent. Yield (0.25 g, 65%). $^1$H NMR (400 MHz, CDCl3): 8.15 (d, J=8.9 Hz, 1H), 7.40 (dd, J=8.9, 2.8 Hz, 1H), 7.18 (d, J=2.8 Hz, 1H), 6.52 (d, J=2.4 Hz, 2H), 6.42 (t, J=-2.4 Hz, 1H), 5.20 (s, 2H), 5.12 (s, 2H), 3.93 (t, J=6.4 Hz, 4H), 2.40 (s, 4H), 1.85-1.68 (m, 4H), 1.48-1.26 (m, 44H), 0.88 (t, J=7.2 Hz, 6H).

1.2.7: Synthesis of 5-((3,5-bis(dodecyloxy)benzyl)oxy)-2-nitrobenzyl(2-(2-(diethoxyphosphoryl)ethoxy)ethyl) Carbamate (7)

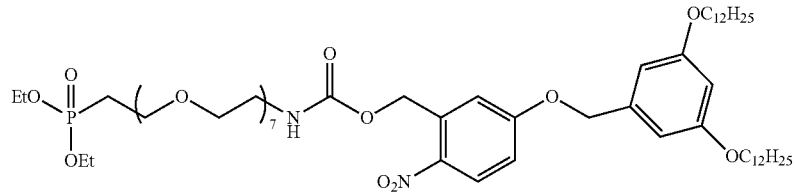

In an oven dried RBF, above activated ester (0.10 g, 1.2 eq) and amine (0.057 g, 1 eq) were dissolved in DCM under stirring. Triethyl amine (0.020 mL, 1.2 eq) was added slowly to the reaction mixture and stirred at RT for 12 hours. Upon completion of reaction, DCM and triethyl amine was evaporated under vacuum. To the obtained residue water was added and extracted thrice with DCM. Combined organic layer was dried over $Na_2SO_4$ and concentrated under vacuum to get crude product which was purified using silica gel column chromatography using silica gel column chromatography using MeOH/DCM as eluent. Yield (0.088 g, 69%). $^1$H NMR (400 MHz, $CDCl_3$) 8.15 (d, J=8.9 Hz, 1H), 7.40 (dd, J=8.9, 2.8 Hz, 1H), 7.18 (d, J=2.8 Hz, 1H), 6.52 (d, J=2.4 Hz, 2H), 6.42 (t, J=2.4 Hz, 1H), 5.12 (s, 2H), 4.14-4.01 (m, 4H), 3.93 (t, J=6.4 Hz, 4H), 3.75-3.57 (m, 34), 2.16-2.05 (m, 2H), 1.85-1.68 (m, 4H), 1.48-1.26 (m, 50H), 0.88 (t, J=7.2 Hz, 6H).

1.2.8: Synthesis of 5-((3,5-bis(dodecyloxy)benzyl)oxy)-2-nitrobenzyl(2-(2-(ethoxy(hydroxy) phosphoryl)ethoxy) ethyl)carbamate (8)

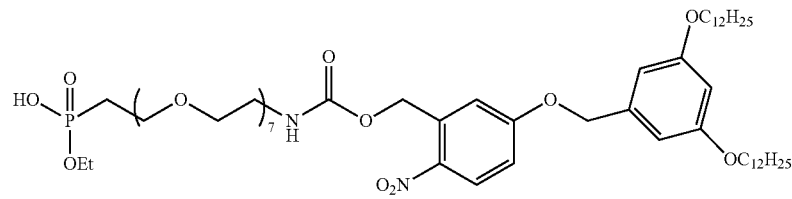

In an oven dried RBF, diphosphonate ester (0.070 g, 1 eq) was taken and LiBr (0.05 g, 10 eq) was added. To the mixture, DMF was added and heated at 95° C. for 20 hours. Upon completion, water was added and extracted thrice with ethyl acetate. The water layer was collected and 2N HCl was added and stirred for 30 minutes. The mixture was then extracted thrice with ethyl acetate. Combined organic layer was dried over $Na_2SO_4$ and concentrated under vacuum to get crude product which was used without purification.

1.2.9: Synthesis of 5-((3,5-bis(dodecyloxy)benzyl)oxy)-2-nitrobenzyl(2-(2-(ethoxyfluoro phosphoryl)ethoxy)ethyl)carbamate (9)

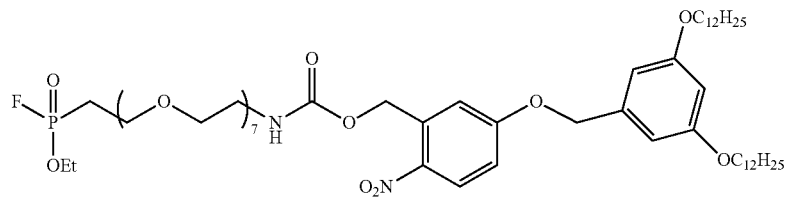

To the stirring solution of monophosphonate ester (0.04 g, 1 eq) in DCM, DAST (0.024 g, 4 eq) was added dropwise at RT and allowed to react for 4 hours. Excess of DAST and DCM were evaporated under vacuum. To the obtained residue, water was added and stirred for 2 more minutes to quench any residual DAST. Reaction mixture was then extracted thrice with DCM. Combined organic layer was dried over $Na_2SO_4$ and concentrated under vacuum. $^{19}F$ NMR (400 MHz, $CDCl_3$): $\delta_F$ –59.91, –62.74.

Example 1.3. Protein Conjugation reaction) of photo-sensitive probe (9) was weighed in a falcon tube (15 mL). Then, 1000 μL of triton X-100 and 10 mL of 50 mM sodium phosphate pH: 7.4 were added and vertexed for 5 minutes or till the solution becomes homogenous. The photo-sensitive probe (9) mixtures (5 mL each) was then added to each of the protein solution and allowed to react on rotospin.

Ion Exchange: The column (SP FF, GE Healthcare) was pre-equilibrated using 50 mM sodium phosphate pH: 7.4 which was also used for conjugation and then sample was injected followed by post injection equilibration until the

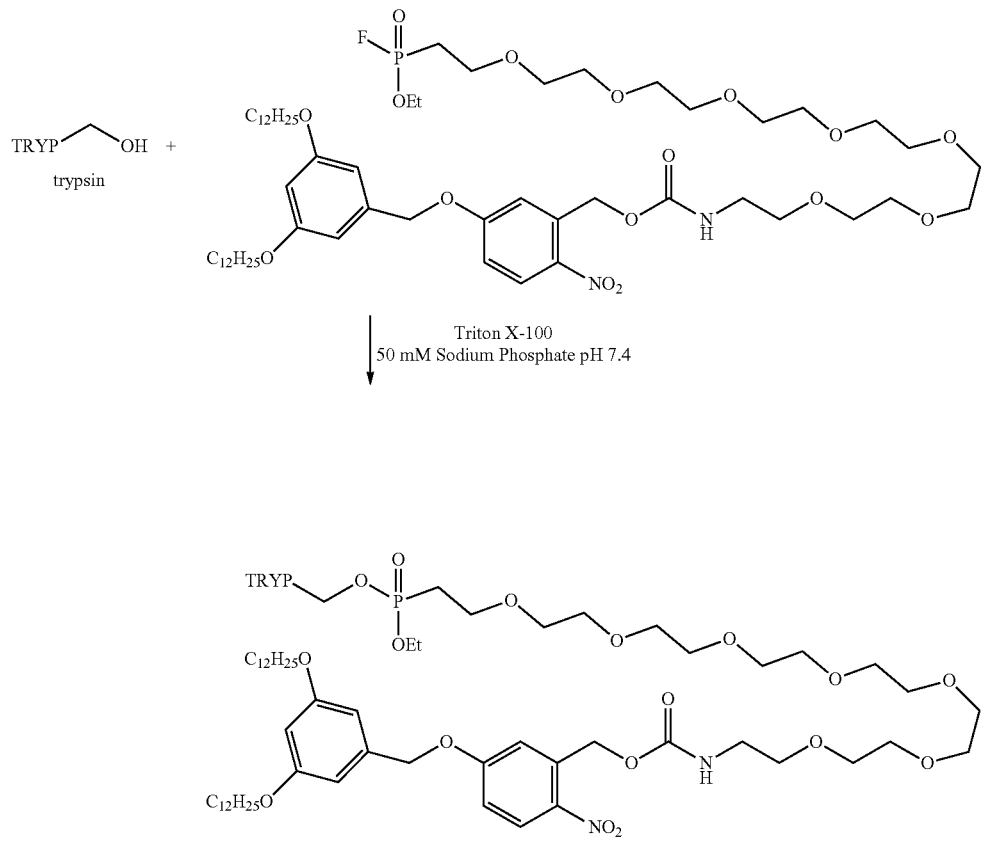

Reaction Conditions:

2.7 mg of trypsin was weighed in 4 centrifuge tubes and 200 μL of sodium phosphate buffer pH: 7.4 was added to each tube. 1 mg of photo-sensitive probe (9) was weighed in another centrifuge tube and 20 μL of triton X-100 and 1 mL of 50 mM sodium phosphate pH: 7.4 were added and vertexed for 5 minutes or till the solution becomes homogenous. The photo-sensitive probe (9) mixtures (100, 200, 300, 400 μL each) was then added to each of protein solutions and volume made up to 1 mL and allowed to react on rotospin. MALDI-TOF MS was monitored.

Scale-Up Reaction Conditions and Purification:

200 mg of trypsin was weighed in 2 falcon tubes (50 mL each) and mixed each with 30 mL of 50 mM sodium phosphate pH: 7.4 for 5-10 minutes. 20 mg (as per test scale complete removal of triton X-100. Elution of the protein was then performed using 1M NaCl as elution buffer.

Size Exclusion: The column (Sephacryl-100, GE Healthcare) was pre-equilibrated with 50 mM sodium phosphate with 1M NaCl for at least 2 CVs and then sample was injected followed by post injection equilibration with the same for at least 2 CVs again or until the complete elution of the proteins.

Desalting and lyophilisation: The column was pre-equilibrated with Milli Q water for at least 2 CVs and then sample was injected followed by post injection equilibration with Milli Q water for at least 2 CVs again until the complete elution of the proteins. The supramolecular protein assembly separated from salt was lyophilised quickly.

Example 2. Synthesis of pH-Sensitive Protein Conjugate of Formula (IA")

Example 2.1. Synthesis of Octa Ethylene Glycol Spacer

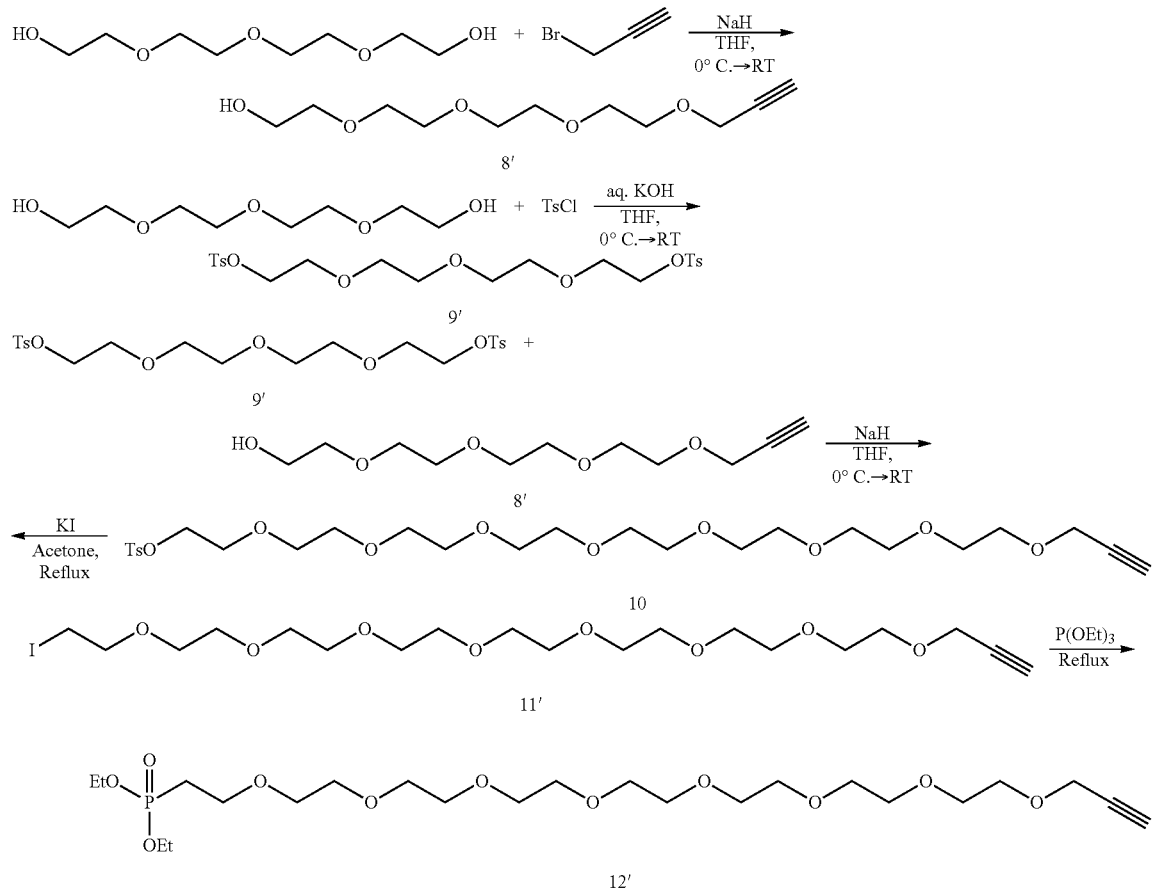

Procedures for Synthesis of Individual Molecules

2.1.1: Synthesis of 3,6,9,12-tetraoxapentadec-14-yn-1-ol (8')

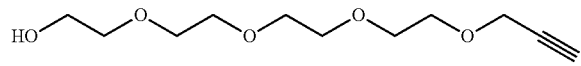 [SMILES: C#CCOCCOCCOCCOCCO]

In an oven dried RBF, tetraethylene glycol (15 g, 1 eq) was dissolved with stirring in THF at 0° C. Sodium hydride (NaH) (1.23 g, 0.7 eq) was added to a flask in small portions immediately. After 15 minutes, propargyl bromide (6.13 g, 0.7 eq) was added drop wise, maintaining the reaction at the same temperature. Then reaction was stirred for 24 hours at RT. upon completion, excess NaH was quenched with drop wise addition of water. Resulting reaction mixture was extracted in DCM thrice. Combined organic layer was dried over $Na_2SO_4$ and concentrated under vacuum to get crude product which was purified using silica gel column chromatography using DCM/MeOH as eluent to get pale liquid. Yield (7 g, 88%); $^1$H NMR (400 MHz, $CDCl_3$) $\delta_H$ 3.92 (d, J=2.4 Hz, 2H), 3.44-3.36 (m, 15H), 3.31 (t, J=4.4 Hz, 3H), 2.34. (t, d=2.4 Hz, 1H); $^{13}$C NMR (100 MHz, $CDCl_3$) $\delta_C$ 79.15, 74.46, 72.03, 69.95, 69.89, 69.86, 69.70, 69.68, 68.43, 60.82, 57.68, 53.30; HRMS ($M^+Na$) 255.12.

2.1.2: Synthesis of ((oxybis(ethane-2,1-diyl))bis (oxy))bis(ethane-2,1-diyl) bis(4-methylbenzenesulfonate) (9')

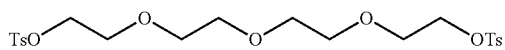 [SMILES: Cc1ccc(S(=O)(=O)OCCOCCOCCOCCOS(=O)(=O)c2ccc(C)cc2)cc1]

In an oven dried RBF, tetraethylene glycol (20 g, 1 eq) was dissolved with stirring in THF. Aqueous KOH (40 g, 2.5 eq) was added to the flask in small portions immediately. After 10 minutes, tosyl chloride (58.70 g, 2.2 eq) solution in THF was added drop wise and stirred for 12 hours. Upon completion, reaction was quenched with aqueous ammonium chloride, and extracted with DCM thrice to get crude product which was purified using silica gel column chromatography using MeOH/DCM as eluent to get pale yellow liquid (45 g, 89 mmol, 87%); $^1$H NMR (400 MHz, $CDCl_3$) $\delta_H$ 17.78 (d, J=8 Hz, 4H), 7.32 (d, J=8 Hz, 4H), 4.15 (t, 0.1=4.8 Hz, 4H), 3.67 (t, J=4.8 Hz, 4H), 3.58-3.53 (m, 8H), 2.44 (s, 6H); $^{13}$C NMR (100 MHz, $CDCl_3$) $\delta_C$ 144.86, 132.97, 129.88, 128.02, 79.68, 77.16, 74.66, 70.74, 70.52, 70.41, 69.31, 69.12, 68.69, 58.42, 21.70; MALDI-ToF (M+K) 541.03.

2.1.3: Synthesis of 3,6,9,12,15,18,21,24-octaoxaheptacos-26-yn-1-yl 4-methylbenzenesulfonate (10')

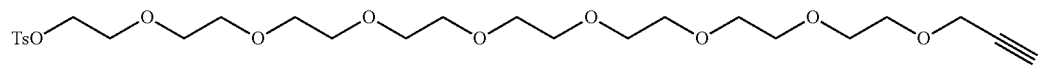 [SMILES: C#CCOCCOCCOCCOCCOCCOCCOCCOCCOS(=O)(=O)c1ccc(C)cc1]

In an oven dried RBF, monobenzyltetraethylene glycol (4.8 g, 1 eq), ditosyltetraethylene glycol (14 g, 2 eq) was dissolved with stirring in THF at 0° C. Immediately, NaH (2 g, 2 eq) was added to flask in portions and then stirred for 36 hours at RT. Upon completion, NaH was quenched by addition of water at 0° C. and extracted with DCM. The combined organic layer was dried over $Na_2SO_4$ and concentrated under vacuum to get crude product which was purified using silica gel column chromatography using MeOH/DCM as eluent to get pale yellow liquid. (5 g, 42%); $^1$H NMR (400 MHz, $CDCl_3$) $\delta_H$ 7.77 (d, J=8 Hz, 2H), 7.32 d, J=8 Hz, 2H), 4.18 (d, J=2.4 Hz, 2H), 4.14 (t, J=3.2 Hz, 2H), 3.69-3.66 (m, 6H), 3.65-3.61 (m, 20H), 3.57 (s, 4H), 2.42 (m, 4H); $^{13}$C NMR (100 MHz, $CDCl_3$) $\delta_C$ 144.78, 132.79, 129.76, 127.87, 70.60, 70.42, 69.20, 68.56, 21.56; MALDI-ToF(M+K): 601.11.

2.1.4: Synthesis of 1-iodo-3,6,9,12,15,18,21,24-octaoxaheptacos-26-yne (11')

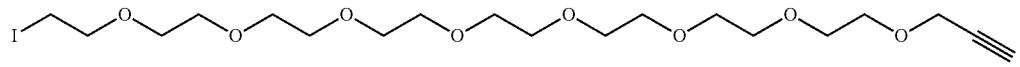 [SMILES: C#CCOCCOCCOCCOCCOCCOCCOCCOCCI]

A mixture of above obtained tosyl(4.6 g, 1 eq) and KI (5.4 g, 4 eq) was refluxed in acetone for 18 hours. Upon completion, excess KI was filtered and washed thrice with acetone. Collected acetone fraction was evaporated under vacuum to get residue, which was then washed with water and extracted with DCM. The combined organic layer was washed with aqueous $Na_2CO_3$ and then concentrated under vacuum to get crude product which was purified using silica gel column chromatography using MeOH/DCM as eluent to get pale yellow liquid product (4 g, 95%); $^1$H NMR (400 MHz, $CDCl_3$) $\delta_H$ 4.19 (d, J=2.4, 2H), 3.75 (t, J=7.2 Hz, 3H), 3.69-3.61 (m, 33H), 3.25 (t, J=7.2 Hz, 2H), 2.43 (t, J=2.4 Hz, 1H); $^{13}$C NMR (100 MHz, $CDCl_3$) $\delta_C$ 79.77, 74.68, 72.09, 70.78, 70.70, 70.52, 70.33, 69.22, 58.53; MALDI-ToF(M+K) 557.03.

2.1.5: Synthesis of Diethyl (3,6,9,12,15,18,21,24-octaoxaheptacos-26-yn-1-yl)phosphonate (12')

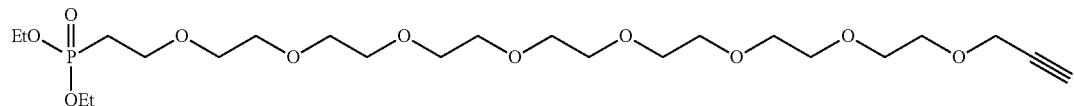 [SMILES: C#CCOCCOCCOCCOCCOCCOCCOCCOCCP(=O)(OCC)OCC]

Above obtained iodide(4 g, 1 eq) and triethylphosphite, P(OEt)$_3$ (5.9 g, 4 eq) were refluxed for 1 hour at 150° C. in an oven-dried RBF. The excess P(OEt)$_3$ was removed under vacuum and the reaction mixture was directly loaded onto a silica-gel column to get pale yellow liquid product (5.61 g, 89%) using MeOH/DCM as eluent; $^1$H NMR (400 MHz, CDCl$_3$) $\delta_H$4.18 (m, 2H), 4.12-4.03 (m, 4H), 3.72-3.58 (m, 30H), 2.42 (t, 2.4 Hz, 1H) 2.16-2.07 (m, 2H), 1.30 (t, J=7.2 Hz, 6H); $^{13}$C NMR (100 MHz, CDCl$_3$) $\delta_C$79.64, 74.65, 70.54, 70.43, 70.39, 70.17, 69.09, 65.12, 61.69, 61.63, 58.41; MALDI-ToF (M+K) 567.15.

Example 2.2. Synthesis of pH-Sensitive Probe (17')

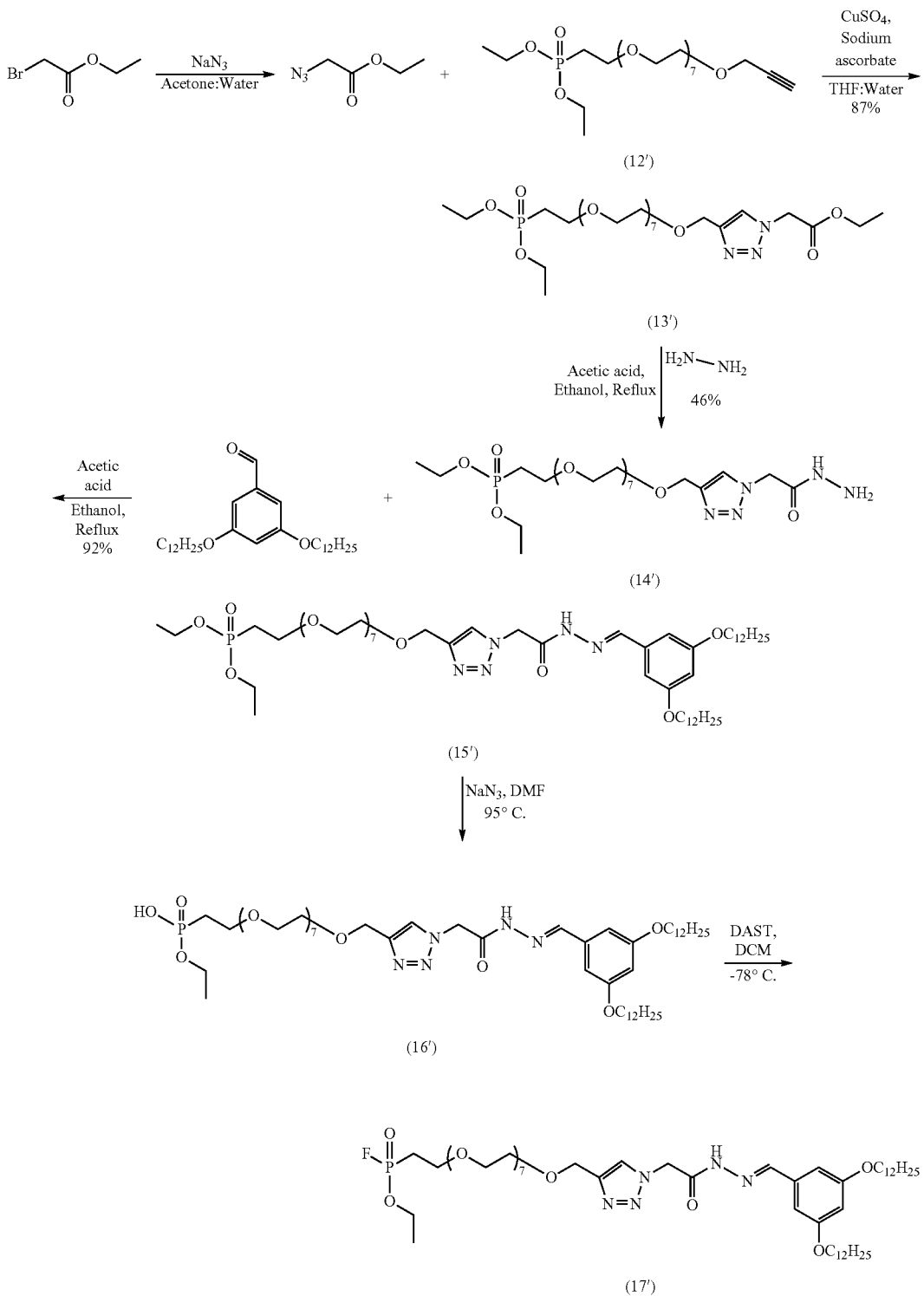

Procedures for Synthesis of Individual Molecules 2.2.1: Synthesis of Ethyl 2-azidoacetate

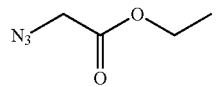

NaN$_3$ (1.1 g, 1.5 eq) was added to a solution of ethyl bromoacetate (2.0 g, 1 eq) in water/acetone (1:3) and the mixture was heated at 60° C. for 4 hours. Then the reaction mixture was quenched with water and extracted thrice with DCM. The organic layer was dried over anhydrous Na$_2$SO$_4$ and evaporated in vacuum. The crude product was obtained as oily liquid in quantitative yield (97%) and was used for the next step without further purification and characterization.

2.2.2: Synthesis of Ethyl4-((2-(2-(diethoxyphosphoryl)ethoxy)methyl)-1H-1,2,3-triazol-1-carboxylate (13')

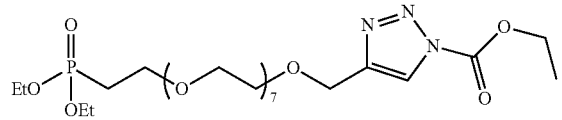

Above azide (0.18 g, 1 eq) and alkyne (12') (0.5 g, leg) were dissolved in degassed THF and stirred until clear solution was obtained, then degassed water was added and stirred vigorously for 10 more minutes. Freshly prepared 1M sodium ascorbate (0.028 g, 0.05 eq) and 1M CuSO$_4$ (0.011 g, 0.1 eq) were added to the reaction mixture at least thrice in an intervals of 45 minutes and allowed to react for 16 hours at RT. Upon completion, reaction mixture was extracted in DCM and combined organic layer was dried over Na$_2$SO$_4$ and concentrated under vacuum to get crude product which was purified using normal phase chromatography using MeOH/DCM solvent system. Yield (0.6 g, 87%) $^1$H NMR (400 MHz, CDCl$_3$): $\delta_H$4.16 (d, J=2.4 Hz, 2H), 3.73-3.62 (m, 15H), 3.22 (t, J=7.8 Hz, 2H), 2.41 (t, J=2.4 Hz, 1H). $^{13}$C NMR (100 MHz, CDCl$_3$): $\delta_C$79.46, 77.16, 74.61, 71.82, 70.51, 70.29, 70.08, 68.98, 58.30, 3.17.

2.2.3: Synthesis of Ethyl ((2-(2-((1-(hydroxycarbonyl)-1H-1,2,3-triazol-4-yl) methyl)ethoxy) phosphate (14')

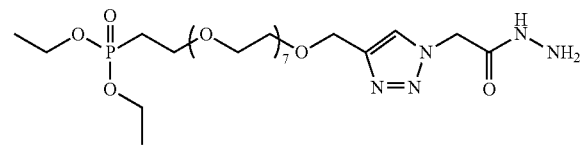

In an oven dried RDF, above ester (1 eq) and hydrazine (excess) were dissolved in absolute ethanol with stirring and refluxed for 12 hours. Upon completion of reaction, excess of ethanol and hydrazine was removed under vacuum. To the obtained residue water was added and washed with DCM. Water layer was evaporated under vacuum to get crude product which was purified by column chromatography using silica gel column chromatography using MeOH/DCM (with 2% TEA) as eluent. Yield (0.37 g, 46%). $^1$H NMR (400 MHz, CDCl$_3$): $\delta_H$7.80 (d, J=8 Hz, 2H), 7.34 (d, J=8 Hz, 2H), 4.20-4.14 (m, 5H), 3.70-3.58 (m, 17H), 2.44-2.41 (m, 4H), 1.68 (s, 3H). $^{13}$C NMR (100 MHz, CDCl$_3$): $\delta_C$144.89, 129.90, 128.07, 79.71, 74.62, 70.81, 70.65, 70.60, 70.46, 69.33, 69.18, 68.75, 58.47, 21.73.

2.2.4: Synthesis of Diethyl (E)-(2-(2-((1-(2-(3,5-bis (dodecyloxy)benzylidene)hydrazine-1-carbonyl)-1H-1,2,3-triazol-4-yl)methoxy)ethoxy)ethyl)phosphonate (15')

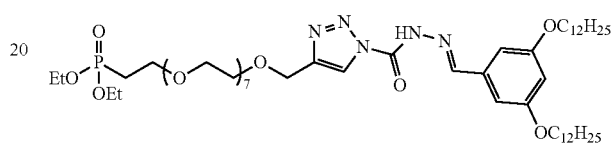

Ethanol was added to the mixture of hydrazine (0.16 g, 1 eq) and aldehyde (0.36 g, 2 eq) in an oven dried RBF. Then two drops of acetic acid was added and resultant mixture was refluxed for 12 hours. Upon completion of reaction, ethanol was removed under vacuum and the obtained residue was loaded and purified using column chromatography using silica gel column chromatography using MeOH/DCM as eluent. Yield (0.30 g, 92%). 1H NMR (400 MHz, CDCl$_3$): $\delta_H$7.89 (s, 1H0, 7.83 (s, 1H), 6.77 (d, J=2.8 Hz, 2H), 6.51 (t, J=2.4 Hz, 1H), 5.65 (s, 2H), 4.75 (s, 2H), 4.15-4.05 (m, 4H), 3.96 (t, J=6.4, 4H), 3.90-3.70 (m, 14H), 2.22-2.26 (m, 2H), 1.82-1.73 (m, 4H), 1.73-1.51 (m, 44H), 0.88 (t, H=7.4 Hz, 6H).

2.2.5: Synthesis of Ethyl Hydrogen (E)-(2-(2-((1-(2-(3,5-bis (dodecyloxy)benzylidene) hydrazine-1-carbonyl)-1H-1,2,3-triazol-4-yl)methoxy)ethoxy)ethyl)phosphonate (16')

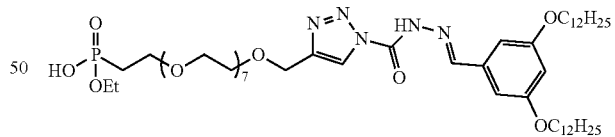

In an oven dried RBF, a mixture of above imine (0.30 g, 1 eq) and sodium azide (0.44 g, 10 eq) were taken and dissolved in DMF with stirring. The mixture was then heated to 95° C. and allowed to react for 18 hours. Upon completion of reaction, DMF was evaporated under vacuum. Water was added to the residue and extracted thrice with DCM. Upon concentration under vacuum, crude product was obtained which was used without further purification. $^1$H NMR (400 MHz, CDCl$_3$): $\delta_H$7.87 (s, 1H0, 7.81 (s, 1H), 6.78 (d, J=2.8 Hz, 2H), 6.51 (t, J=2.4 Hz, 1H), 5.61 (s, 2H), 4.75 (s, 2H), 4.15-4.05 (m, 2H), 3.96 (t, J=6.4, 4H), 3.90-3.70 (m, 14H), 2.22-2.26 (m, 2H), 1.82-1.73 (m, 4H), 1.73-1.51 (m, 44H), 0.88 (t, H=7.4 Hz, 6H).

2.2.6: Synthesis of Ethyl (E)-(2-(2-((1-(2-(3,5-bis(dodecyloxy)benzylidene)hydrazine-1-carbonyl)-1H-1,2,3-triazol-4-yl)methoxy)ethoxy)ethyl)phosphonofluoridate (17')

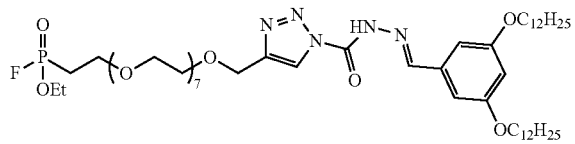

To the stirring solution of monophosphonate ester (1 eq) in DCM at −78° C., DAST (4 eq) was added dropwise at RT and allowed to react for 15 minutes. Excess of DAST and DCM were evaporated under vacuum. To the obtained residue, was then extracted thrice with DCM. Combined organic layer was dried over $Na_2SO_4$ and concentrated under vacuum to get crude product. $^{19}F$ NMR (400 MHz, $CDCl_3$): $\delta_F$ −59.91, −62.74.

Example 2.3. Protein Conjugation

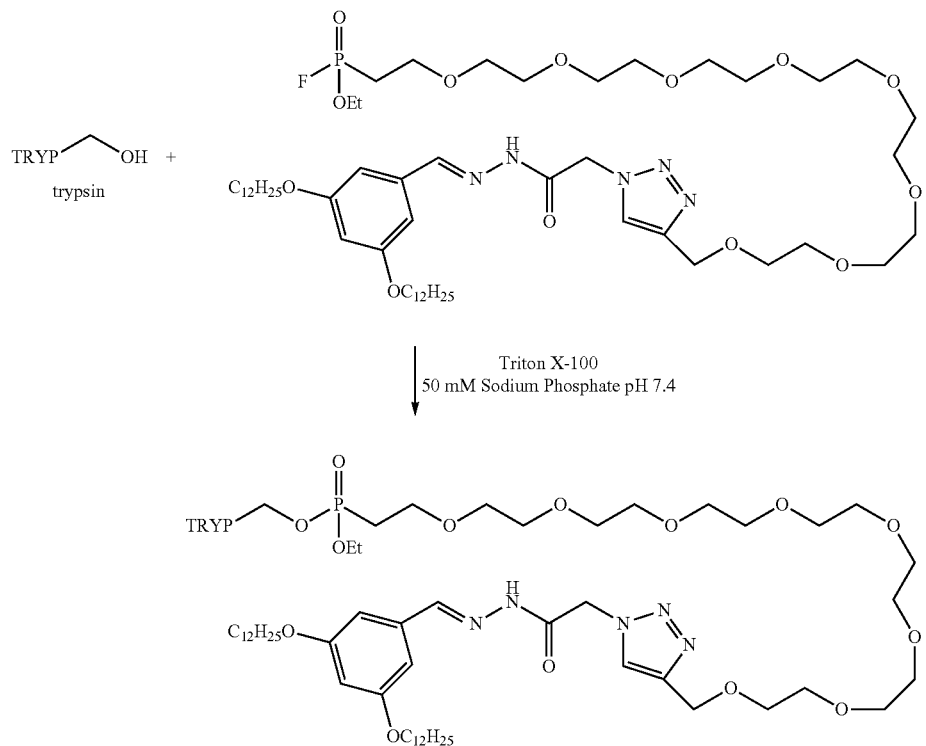

Reaction Conditions:

2.7 mg of trypsin was weighed in 4 centrifuge tubes and 200 μL of sodium phosphate buffer pH: 7.4 was added to each tube. 1 mg of pH-sensitive probe (17') was weighed in another centrifuge tube and 20 μL of triton X-100 and 1 mL of 50 mM sodium phosphate pH: 7.4 were added and vertexed for 5 minutes or till the solution becomes homogenous. The pH-sensitive probe (17') mixture (100, 200, 300, 400 μL each) was then added to each of protein solutions and volume made up to 1 mL and allowed to react on rotospin.

Scale-Up Reaction Conditions and Purification:

200 mg of trypsin was weighed in 2 falcon tubes (50 mL each) and mixed each with 30 mL of 50 mM sodium phosphate buffer pH: 7.4 for 5-10 minutes. 20 mg (as per test scale reaction) of pH-sensitive probe (17') was weighed in a falcon tube (15 mL). Then, 1000 μL of triton X-100 and 10 mL of 50 mM sodium phosphate pH: 7.4 were added and vertexed for 5 minutes or till the solution becomes homogenous. The pH-sensitive probe (17') mixtures (5 mL each) was then added to each of the protein solution and allowed to react on rotospin.

Ion Exchange: The column (SP FF, GE Healthcare) was pre-equilibrated using 50 mM sodium phosphate pH: 7.4 which was also used for conjugation and then sample was injected followed by post injection equilibration until the complete removal of triton X-100. Then elution of the protein was then performed using 1M NaCl as elution buffer.

Size Exclusion: The column (Sephacryl-300, GE Healthcare) was pre-equilibrated with 50 mM sodium phosphate with 1M NaCl for at least 2 CVs and then sample was injected followed by post injection equilibration with the same for at least 2 CVs again or until the complete elution of the proteins.

Desalting and lyophilization: The column was pre-equilibrated with Milli Q water for at least 2 CVs and then sample was injected followed by post injection equilibration with Milli Q water for at least 2 CVs again until the complete elution of the proteins. The supramolecular protein assembly separated from salt was lyophilized quickly.

Example 3. Synthesis of Redox-Sensitive Supramolecular Protein Conjugate (IA''')
Example 3.1. Synthesis of Redox-Responsive AABP
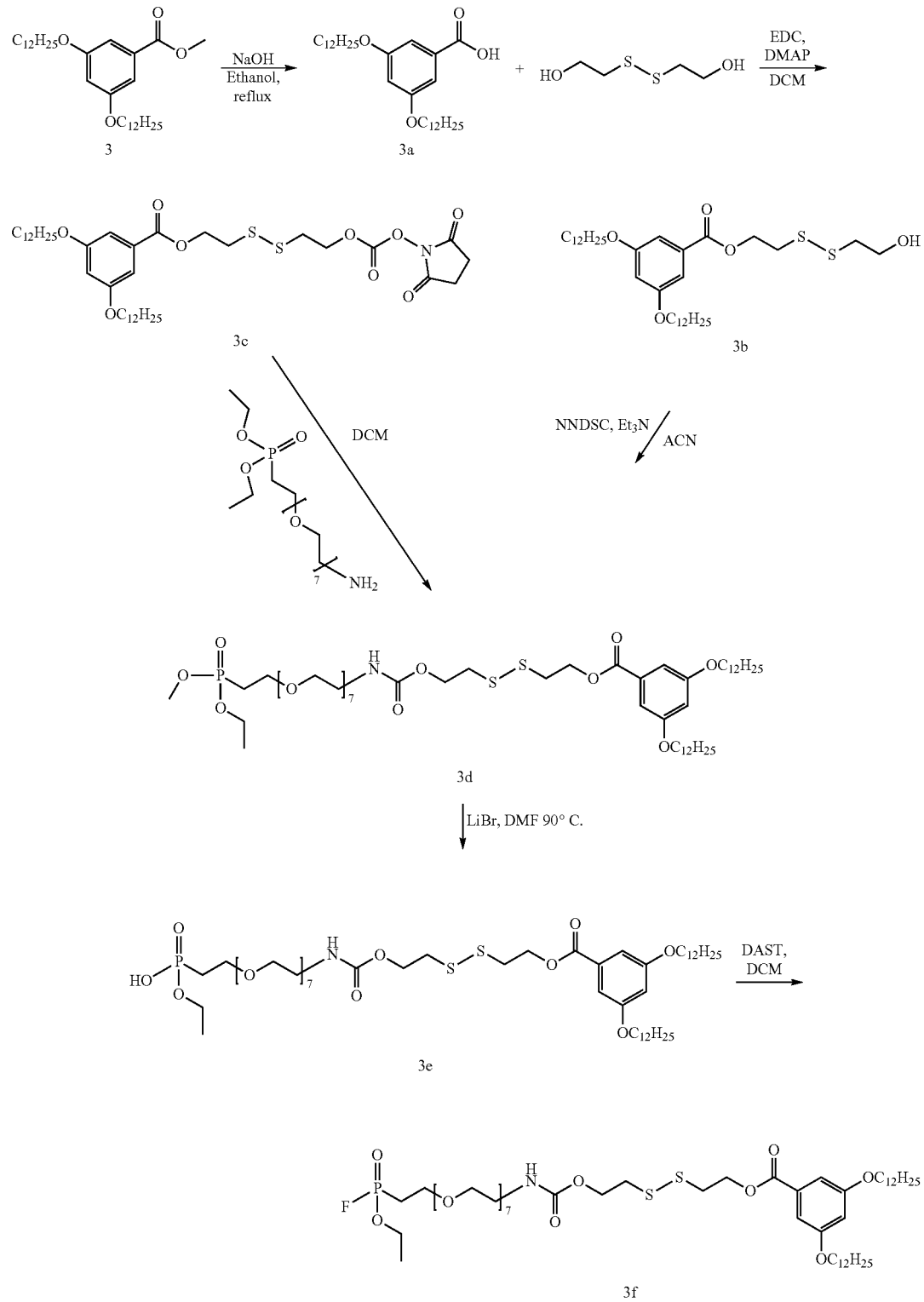

Compound 3b was obtained from reaction between 2,2'-disulfanediylbis(ethan-1-ol) and 3,5-bis(dodecyloxy)benzoic acid (3a) in presence of EDC and DMAP in DCM. Then this compound 3b was activated using NN-DSC, in the presence of TEA to yield compound 3c. The activated ester 3c was then reacted with amine in the presence of Et₃N and DMF to obtain compound 3d. Then, the resultant diphosphonate ester 3d was heated with lithium bromide (LiBr) in DMF to get monophosphonate ester 3e which finally on fluorination using DAST in DCM afforded flurophosphonate 3f.

Procedures for Synthesis of Individual Molecules

Synthesis of 3,5-bis(dodecyloxy)benzoic Acid (19')

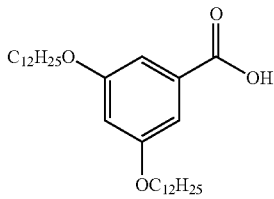

The compound (19) (3 g, 5 mmol), sodium hydroxide (NaOH) (0.5 g, 10 mmol) were dissolved in ethanol. The mixture was then refluxed for 4 hours. Upon completion, reaction was quenched with dropwise addition of water and acidified with conc. HCL. The obtained precipitate was filtered and washed with ethanol for two times. The combined organic layer dried over Na₂SO₄ and concentrated under reduced pressure to get crude product which was utilized for next reaction without further purification. The product obtained was white solid (1.7 g, 3 mmol, 60%), Rf=0.10 in 10% EtOAc/hexane. ¹H NMR (400 MHz, CDCl³): δH 7.21 (d, J=2.4 Hz, 2H), 6.68 (t, J=2.4 Hz, 1H), 3.98 (t, J=6.4 Hz, 2H), 1.85-1.73 (m, 4H), 1.52-1.17 (m, 38H), 0.88 (t, J=6.8 Hz, 6H).

Synthesis of 2-((2-hydroxyethyl)disulfaneyl)ethyl 3,5-bis(dodecyloxy)benzoate(19'a)

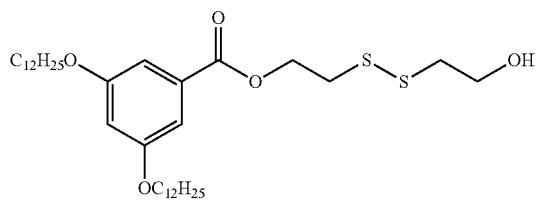

In an oven dried RBF compound 19'a (2.5 g, 5 mmol), 2,2'-disulfanediylbis(ethan-1-ol) (1.9 g, 10 mmol) and DMAP (0.3 g, 2 mmol) were taken and dissolved in DCM under stirring. Then, solution of EDC in DCM (2 g, 10 mmol) was added slowly to above mixture and allowed to stir for 12 hours. Upon completion, reaction was quenched with water and resulting content was extracted in DCM thrice. Combined organic layers was dried over Na₂SO₄ and concentrated under reduced pressure to get crude product which was purified using silica gel column chromatography. The product obtained was white solid (2.2 g, 3 mmol, 70%), Rf=0.20 in 10% EtOAc/hexane. ¹H NMR (400 MHz, CDCl₃): δH 7.16 (d, J=2.4 Hz, 2H), 6.64 (t, J=2.4 Hz, 1H), 4.57 (t, J=6.4 Hz, 2H), 3.96 (t, J=6.4 Hz, 2H), 3.91-9.87 (m, 2H), 3.05 (t, J=6.8 Hz, 2H), 2.90 (t, J=6.8 Hz, 2H), 1.84-1.73 (m, 4H), 1.52-1.26 (m, 38H), 0.88 (t, J=6.8 Hz, 6H). ¹³C NMR (100 MHz, CDCl₃): δC 166.48, 160.30, 131.58, 107.88, 106.76, 77.16, 68.47, 63.12, 60.33, 41.81, 37.12, 32.05, 29.79, 29.77, 29.73, 29.71, 29.49, 29.48, 29.30, 26.14, 22.82, 14.25. MALDI-TOF MS (M+Na): 665.47.

Synthesis of 2-((2-((((2,5-dioxopyrrolidin-1-yl) oxy) carbonyl) oxy)ethyl)disulfaneyl)ethyl 3,5-bis(dodecyloxy)benzoate (19'c)

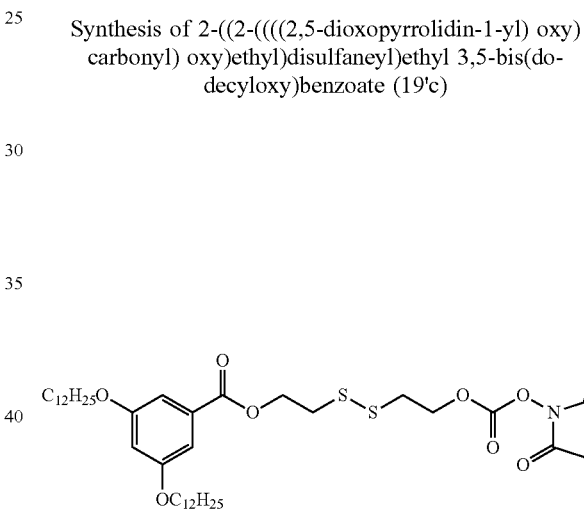

The compound 19'c was prepared by general procedure I, starting from compound 19'b (0.5 g, 0.8 mmol) and N,N'-DSC (1.6 g, 6 mmol) and Et₃N (0.6 g, 5 mmol). The product obtained was pale yellow solid (0.4 g, 0.5 mmol, 65%), Rf=0.18 in 25% EtOAc/hexane. ¹H NMR (400 MHz, CDCl3): δH 7.14 (d, J=2.4 Hz, 2H), 6.63 (t, J=2.4 Hz, 1H), 4.59-4.54 (m, 4H), 3.96 (t, J=6.4 Hz, 2H), 3.08-3.01 (m, 4H), 2.82 (s, 4H), 1.80-1.73 (m, 4H), 1.47-1.26 (m, 38H), 0.87 (t, J=6.8 Hz, 6H). 13C NMR (100 MHz, CDCl₃): δC 168.60, 166.33, 160.28, 151.54, 131.60, 107.85, 106.75, 68.84, 68.45, 62.96, 37.32, 36.39, 32.03, 29.78, 29.75, 29.72, 29.69, 29.49, 29.47, 29.29, 26.13, 25.56, 22.80, 14.24.

Synthesis of 33-(diethoxyphosphoryl)-8-oxo-7,13,16,19,22,25,28,31-octaoxa-3,4-dithia-9-azatriacontyl 3,5-bis(dodecyloxy)benzoate(19'd)

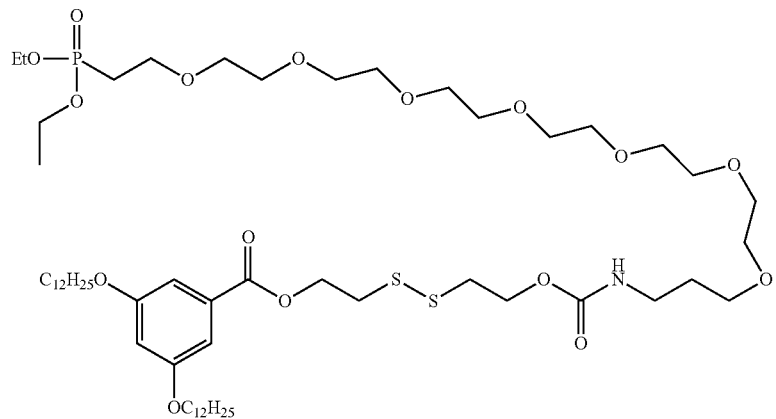

The compound 19'd was prepared by general procedure J, starting from compound 19'c (0.10 g, 0.13 mmol) and compound 1i (0.06 g, 0.11 mmol). The product obtained was pale yellow liquid (0.09 g, 0.07 mmol, 65%), Rf=0.40 in 5% MeOH/DCM. $^1$H NMR (400 MHz, CDCl$_3$): $^\delta$H 7.14 (d, J=2.4 Hz, 2H), 6.62 (t, J=2.4 Hz, 1H), 4.54 (t, J=6.8 Hz, 2H), 4.30 (m, 2H), 4.15-4.03 (m, 4H), 3.95 (t, J=6.4 Hz, 2H), 3.77-3.47 (m, 30H), 3.03 (t, J=6.4 Hz, 2H), 2.93 (t, J=6.8 Hz, 2H), 2.20-2.02 (m, 2H), 1.79-1.72 (m, 4H), 1.51-1.18 (m, 46H), 0.86 (t, J=6.8 Hz, 6H).

Synthesis of 33-(ethoxy(hydroxy)phosphoryl)-8-oxo-7,13,16,19,22,25,28,31-octaoxa-3,4-dithia-9-azatriacontyl 3,5-bis(dodecyloxy)benzoate (19'e)

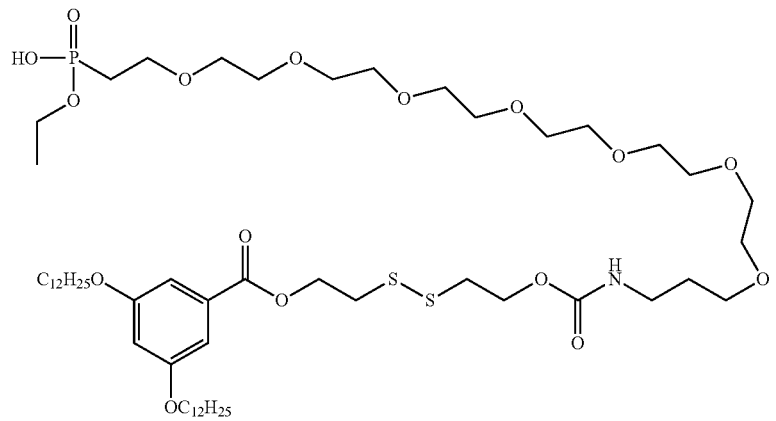

The compound 19'e was prepared by general procedure K, starting from compound 19'd (0.070 g, 0.06 mmol) and LiBr (0.050 g, 0.6 mmol). The obtained get crude product which was used without purification.

Synthesis of 33-(ethoxyfluorophosphoryl)-8-oxo-7,13,16,19,22,25,28,31-octaoxa-3,4-dithia-9-azatriacontyl 3,5-bis(dodecyloxy)benzoate (19' f)

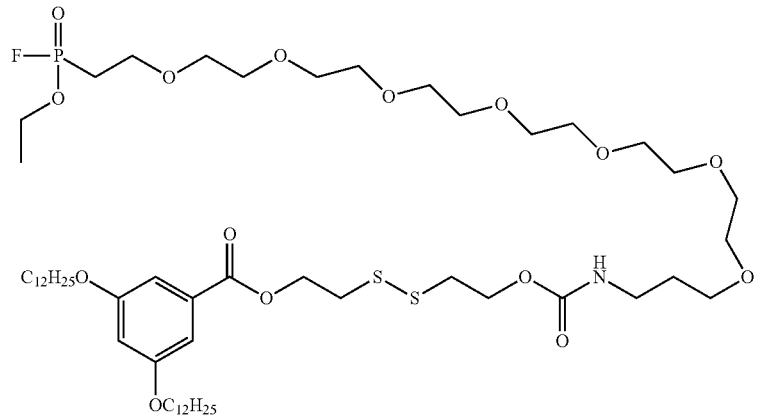

The compound 19'f was prepared by general procedure L, starting from compound 19'e (0.04 g, 0.03 mmol), DAST (0.024 g, 0.14 mmol. The obtained get crude product which was used without purification. $^{19}$F NMR (400 MHz, CDCl$_3$): $\delta_F$ −59.91, −62.74.

Example 3.2. Protein Conjugation

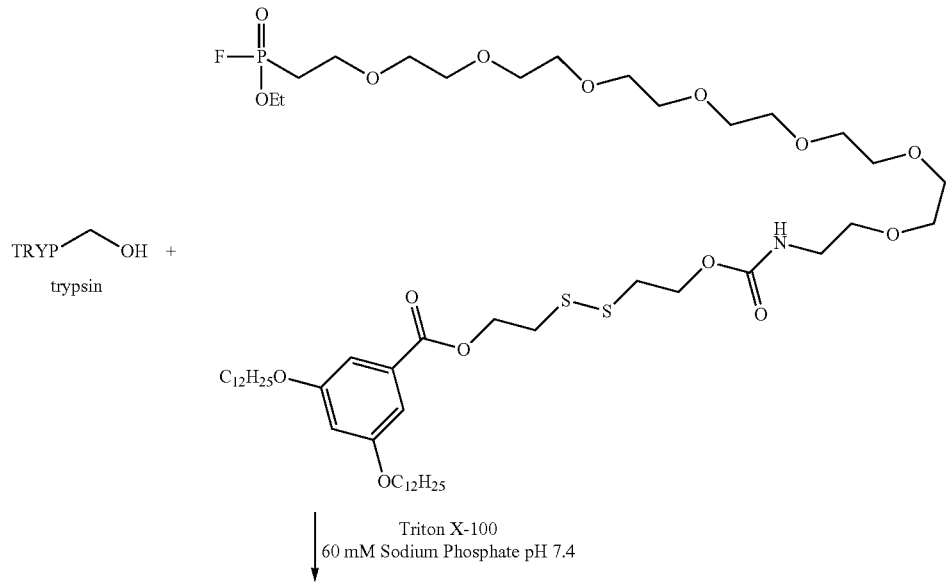

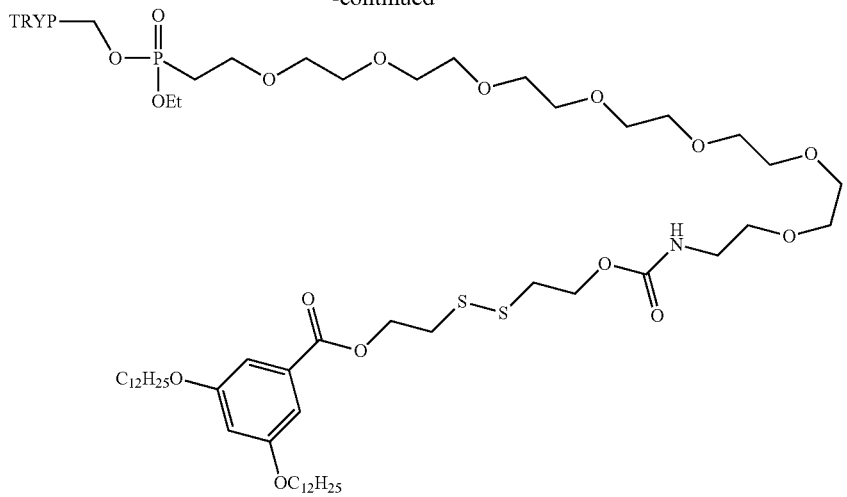

Reaction Conditions:

2.7 mg of trypsin was weighed in 4 centrifuge tubes and 200 μL of sodium phosphate buffer pH: 7.4 was added to each tube. 1 mg of redox-sensitive probe (17') was weighed in another centrifuge tube and 20 μL of triton X-100 and 1 mL of 50 mM sodium phosphate pH: 7.4 were added and vertexed for 5 minutes or till the solution becomes homogenous. The redox-sensitive probe (17') mixture (100, 200, 300, 400 μL each) was then added to each of protein solutions and volume made up to 1 mL and allowed to react on rotospin.

Scale-Up Reaction Conditions and Purification:

200 mg of trypsin was weighed in 2 falcon tubes (50 mL each) and mixed each with 30 mL of 50 mM sodium phosphate buffer pH: 7.4 for 5-10 minutes. 20 mg (as per test scale reaction) of pH-sensitive probe (17') was weighed in a falcon tube (15 mL). Then, 1000 μL of triton X-100 and 10 mL of 50 mM sodium phosphate pH: 7.4 were added and vertexed for 5 minutes or till the solution becomes homogenous. The pH-sensitive probe (17') mixtures (5 mL each) was then added to each of the protein solution and allowed to react on rotospin.

Ion Exchange: The column (SP FF, GE Healthcare) was pre-equilibrated using 50 mM sodium phosphate pH: 7.4 which was also used for conjugation and then sample was injected followed by post injection equilibration until the complete removal of triton X-100. Then elution of the protein was then performed using 1M NaCl as elution buffer.

Size Exclusion: The column (Sephacryl-300, GE Healthcare) was pre-equilibrated with 50 mM sodium phosphate with 1M NaCl for at least 2 CVs and then sample was injected followed by post injection equilibration with the same for at least 2 CVs again or until the complete elution of the proteins.

Desalting and lyophilization: The column was pre-equilibrated with Milli Q water for at least 2 CVs and then sample was injected followed by post injection equilibration with Milli Q water for at least 2 CVs again until the complete elution of the proteins. The supramolecular protein assembly separated from salt was lyophilized quickly.

Example 4. Synthesis of Multi Stimuli-Sensitive Protein Conjugate (IA'''')

Example 4.1. Synthesis of Amine Terminated Cetylethylene Glycol Spacers and their Intermediates

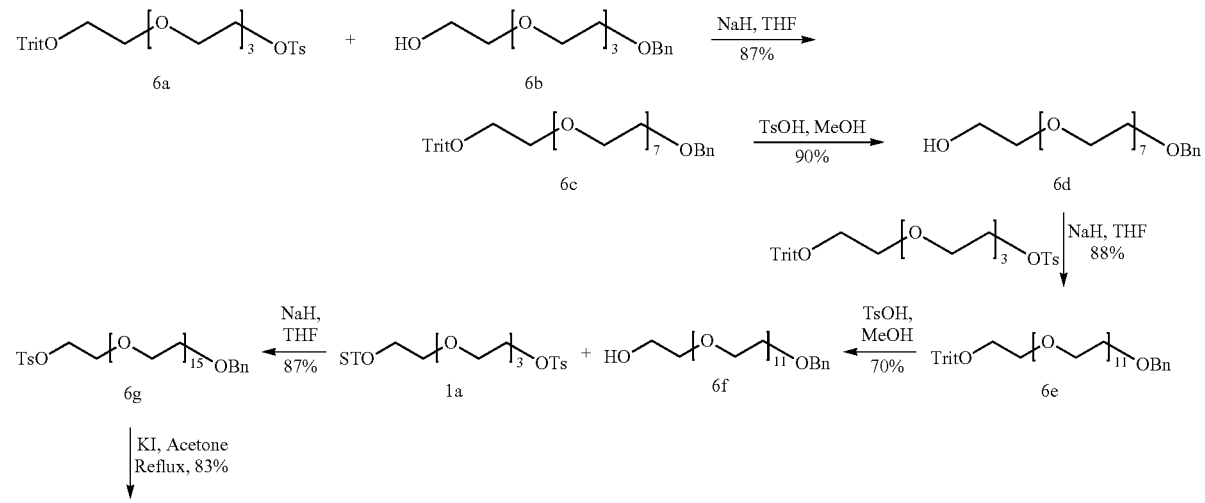

-continued

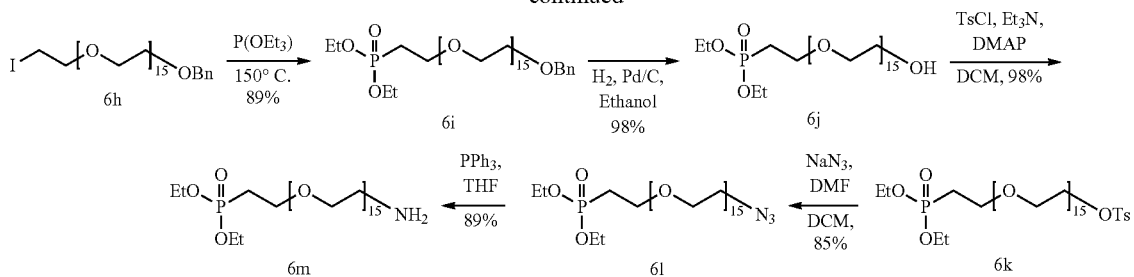

Synthesis of 1,1,1-triphenyl-2,5,8,11-tetraoxatridecan-13-yl 4-methylbenzenesulfonate (6a)

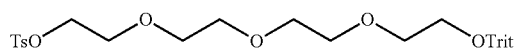

Monotrityl tetraethylene glycol (20a) (58 g, 132 mmol) was dissolved in THF under stirring. To the above solution, aq. solution of potassium hydroxide (KOH) (26 g, 464 mmol) was added and allowed to stir for 10 minutes. Then, a solution of TsCl (75 g, 398 mmol) in THF was slowly added and allowed to react for 12 hours at RT. Upon completion, reaction was quenched by dropwise addition of water and extracted with DCM for thrice. Combined organic layer was dried over $Na_2SO_4$ and concentrated under reduced pressure to get a crude product which was purified using silica gel column chromatography using EtOAc/Hexane as eluent. The product was obtained as pale yellow liquid (66 g, 112 mmol, 85%), Rf=0.40 in 50% EtOAc/Hexane. 1H NMR (400 MHz, $CDCl_3$): $\delta$H 7.77 (d, J=8 Hz, 2H), 7.47 (d, J=8 Hz, 6H), 7.32-7.20 (m, 11H), 4.14-4.11 (t, J=8 Hz, 2H), 3.70-3.56 (m, 12H), 3.24-3.21 (t, J=8 Hz, 2H), 2.42 (s, 3H), MALDI-TOF MS (M+K): 629.59.

6.1.2 Synthesis of 1-phenyl-2,5,8,11-tetraoxatridecan-13-ol (6b)

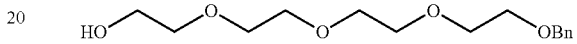

In an oven dried RBF, tetraethylene glycol (15.0 g, 77 mmol) was dissolved with stirring in THF. Then, NaH (1.23 g, 51 mmol) was added to the flask in small portions at 0° C. After 1 hour, benzyl bromide(6.13 g, 51 mmol) was added dropwise, maintaining the reaction at the same temperature. Then, reaction was stirred for 12 h at RT. Upon completion, reaction was quenched by dropwise addition of water and extracted with DCM for thrice. Combined organic layer was dried over $Na_2SO_4$ and concentrated under reduced pressure to get a crude product which was purified using silica gel column chromatography using MeOH/DCM as eluent. The product was obtained as pale yellow liquid (4.6 g, 30 mmol, 58%), Rf=0.34 in 5% MeOH/DCM. 1H NMR (400 MHz, $CDCl_3$): $\delta$H 7.32-7.26 (m, 5H), 4.55 (s, 2H), 3.71-3.57 (m, 16H).

6.1.3 Synthesis of 1,1,1,27-tetraphenyl-2,5,8,11,14,17,20,23,26-nonaoxaheptacosane (6c)

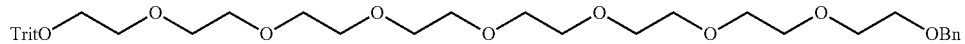

The compound 6c was prepared by general procedure M, starting from compound 6a (3.8 g, 6 mmol), compound 6b (1.1 g, 4 mmol) and NaH (0.3 g, 12 mmol) in THF. The product was obtained as a pale yellow liquid (2.5 g, 3 mmol, 87%) after purification by silica gel column chromatography using MeOH/DCM as eluent, Rf=0.47 in 5% MeOH/DCM. 1H NMR (400 MHz, $CDCl_3$): $\delta$H 7.48 (d, J=8 Hz, 6H), 7.36-7.23 (m, 14H), 4.58 (s, 2H), 3.70-3.56 (m, 31H), 3.27-3.24 (t, J=8 Hz, 2H), 13C NMR (100 MHz, CDCl3): 144.18, 138.31, 128.77, 128.41, 128.00, 127.81, 126.97, 73.28, 70.72, 70.69, 70.64, 70.61, 69.48, 63.37. MALDI-TOF MS (M+Na): 725.42.

6.1.4 Synthesis of 1-phenyl-2,5,8,11,14,17,20,23-octaoxapentacosan-25-ol

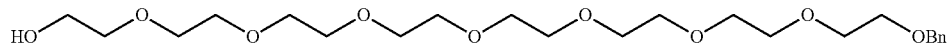 [SMILES: OCCOCCOCCOCCOCCOCCOCCOCCOCc1ccccc1]

The compound 6d was prepared by general procedure N, starting from compound 6c (2.4 g, 3 mmol) and TsOH (0.5 g, 2 mmol) in MeOH. The product was obtained as a pale yellow liquid (1.4 g, 3 mmol, 90%) after purification by silica gel column chromatography using MeOH/DCM as eluent, Rf=0.43 in 5% MeOH/DCM. $^1$H NMR (400 MHz, CDCl$_3$): $\delta^H$ 7.33-7.26 (m, 5H), 4.56 (s, 2H), 3.71-3.58 (m, 32H). 13C NMR (100 MHz, CDCl$_3$) $\delta^C$ 138.21, 128.30, 127.68, 127.53, 73.16, 72.55, 70.57, 70.52, 70.49, 70.23, 69.37, 63.69, 61.58. MALDI-ToF MS (M+K): 499.23.

6.1.5 Synthesis of 1,1,1,39-tetraphenyl-2,5,8,11,14,17,20,23,26,29,32,35,38-tridecaoxanonatriacontane (6e)

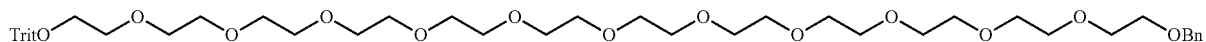

The compound 6e was prepared by general procedure M, starting from compound 6d (0.9 g, 2 mmol), compound 6a (1.8 g, 3 mmol) and NaH (0.25 g, 10 mmol) in THF. The product was obtained as a pale yellow liquid (1.5 g, 1.7 mmol, 88%) after purification by silica gel column chromatography using MeOH/DCM as eluent, Rf=0.47 in 5% MeOH/DCM. 7.49 (d, J=8 Hz, 6H), 7.35-7.22 (m, 14H), 4.58 (s, 2H), 3.70-3.56 (m, 47H), 3.27-3.24 (t, J=8 Hz, 2H). 13C NMR (100 MHz, CDCl3) δC 144.15, 138.26, 128.75, 128.41, 127.81, 127.65, 126.97, 86.58, 73.27, 70.80, 70.71, 70.56, 69.45, 63.36, 53.53. MALDI-TOF MS (M+Na): 901.34.

6.1.6 Synthesis of 1-phenyl-2,5,8,11,14,17,20,23,26,29,32,35-dodecaoxaheptatriacontan-37-ol

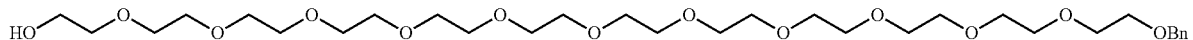 [SMILES: OCCOCCOCCOCCOCCOCCOCCOCCOCCOCCOCCOCCOCc1ccccc1]

The compound 6f was prepared by general procedure N, starting from compound 6e (1.5 g, 1.7 mmol) and TsOH (0.16 g, 0.8 mmol) in MeOH. The product was obtained as a pale yellow liquid (0.98 g, 1.5 mmol, 88%) after purification by silica gel column chromatography using MeOH/DCM as eluent, Rf=0.43 in 5% MeOH/DCM. $^1$H NMR (400 MHz, CDCl$_3$): $\delta^H$ 7.33-7.25 (m, 5H), 4.54 (s, 2H), 3.70-3.58 (m, 52H). MALDI-ToF MS (M+K): 675.28.5.4.2.7.

6.1.7: Synthesis of 1-phenyl-2,5,8,11,14,17,20,23,26,29,32,35,38,41,44,47-hexadecaoxanonatetracontan-49-yl 4-methylbenzenesulfonate

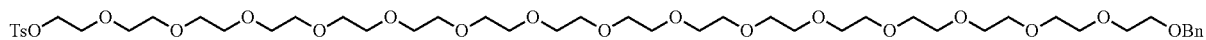 [SMILES: Cc1ccc(S(=O)(=O)OCCOCCOCCOCCOCCOCCOCCOCCOCCOCCOCCOCCOCCOCCOCCOCCOCc2ccccc2)cc1]

The compound 6g was prepared by general procedure M, starting from compound 6f (1 g, 1.5 mmol), compound 1a (2.3 g, 5 mmol), and NaH (0.150 g, 6 mmol), The product was obtained as a pale yellow liquid (0.7 g, 0.7 mmol, 70%) after purification by silica gel column chromatography using MeOH/DCM as eluent, Rf=0.43 in 5% MeOH/DCM. MALDI-ToF MS (M+K): 1005.23.

6.1.8: Synthesis of 49-iodo-1-phenyl-2,5,8,11,14,17, 20,23,26,29,32,35,38,41,44,47-hexadecaoxanonatetracontane

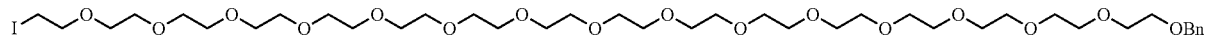 [SMILES: ICCOCCOCCOCCOCCOCCOCCOCCOCCOCCOCCOCCOCCOCCOCCOCCOCc1ccccc1]

The compound 6h was prepared by general procedure A, starting from compound 6g (0.6 g, 0.6 mmol), KI (0.3 g, 1.8 mmol). The product was obtained as a pale yellow liquid (0.5 g, 0.5 mmol, 87%), Rf=0.45 in 5% MeOH/DCM. 1H NMR (400 MHz, CDCl$_3$): $\delta$H 7.34-7.24 (m, 5H), 4.57 (s, 2H), 3.75 (t, J=6.8 Hz, 2H), 3.69-3.58 (m, 64H), 3.26 (t, J=6.8 Hz, 2H). 13C NMR (100 MHz, CDCl$_3$): $\delta$C 138.13, 128.22, 127.59, 127.45, 73.06, 71.81, 70.47, 70.37, 70.06, 69.28, 2.95. MALDI-ToF MS (M+K):961.29.

6.1.9: Synthesis of Diethyl (1-phenyl-2,5,8,11,14, 17,20,23,26,29,32,35,38,41,44,47-hexadecaoxanonatetracontan-49-yl)phosphonate

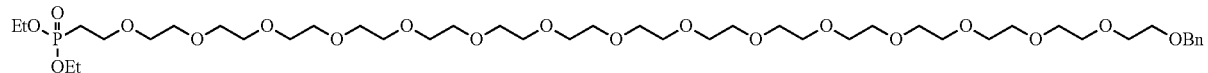 [SMILES: CCOP(=O)(CCOCCOCCOCCOCCOCCOCCOCCOCCOCCOCCOCCOCCOCCOCCOCCOCc1ccccc1)OCC]

The compound 6i was prepared by general procedure A, starting from compound iodide 6 h (0.54 g, 0.5 mmol) and triethyl phosphite, P(OEt)3 (0.27 g, 1.4 mmol). The product was obtained as a pale yellow liquid (0.45 g, 0.4 mmol, 83%), Rf=0.45 in 5% MeOH/DCM. 1H NMR (400 MHz, CDCl$_3$): $\delta$H 7.39-7.27 (m, 5H), 4.56 (s, 2H), 4.16-4.05 (m, 4H), 3.81-3.62 (m, 64H), 2.17-1.98 (m, 2H), 1.32 (t, J=6.8 Hz, 6H). $^{13}$C NMR (100 MHz, CDCl$_3$): $\delta^C$ 138.03, 128.10, 127.46, 127.32, 72.94, 70.37, 70.29, 69.93, 69.19, 64.86, 61.39, 61.33, 27.41, 26.02, 16.24, 16.18. MALDI-ToF MS (M+K): 971.18.

6.1.10: Synthesis of Diethyl (47-hydroxy-3,6,9,12, 15,18,21,24,27,30,33,36,39,42,45-pentadecaoxaheptatetracontyl)phosphonate

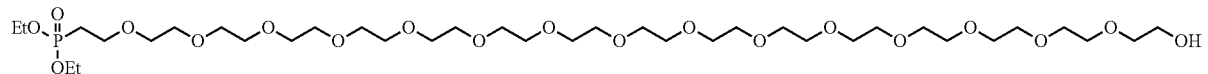 [SMILES: CCOP(=O)(CCOCCOCCOCCOCCOCCOCCOCCOCCOCCOCCOCCOCCOCCOCCOCCO)OCC]

The disphosphonate ester 6i (0.4 g, 0.4 mmol) was dissolved in alcohol, Pd/C was added and stirred under hydrogen for about 18 hours. Upon completion, the mixture was filtered through celite and washed with alcohol; the filtrate was concentrated under vacuum to get crude mixture 6j and used for next step without purification. The product was obtained as a pale yellow liquid (0.35 g, 0.4 mmol, 89%), Rf=0.45 in 5% MeOH/DCM. 1H NMR (400 MHz, CDCl$_3$): $\delta^H$ 4.07-3.93 (m, 4H), 3.66-3.49 (m, 63H), 2.11-1.99 (m, 2H), 1.22 (t, J=6.8 Hz, 6H). 13C NMR (100 MHz, CDCl$_3$): $\delta^C$ 70.43, 70.33, 70.14, 70.07, 64.99, 61.56, 61.49, 27.53, 26.14, 16.36, 16.30. MALDI-ToF MS (M+K): 981.72.

6.1.11: Synthesis of 47-(diethoxyphosphoryl)-3,6,9,12,15,18,21,24,27,30,33,36,39,42,45-penta decaoxa-heptatetracontyl 4-methylbenzenesulfonate

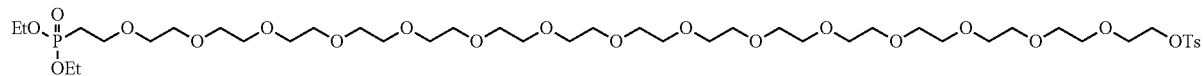 [SMILES: CCOP(=O)(CCOCCOCCOCCOCCOCCOCCOCCOCCOCCOCCOCCOCCOCCOCCOCCOS(=O)(=O)c1ccc(C)cc1)OCC]

The compound 6k was prepared by general procedure D, starting from compound 6j (0.33 g, 0.4 mmol), TsCl (0.30 g, 1 mmol), DMAP (0.0079 g, 0.06 mmol) and Et3N (0.16 g, 1.5 mmol). The product obtained was pale yellow liquid (0.39 g, 4 mmol, 98%), Rf=0.40 in 5% MeOH/DCM. $^{1H}$ NMR (400 MHz, CDCl$_3$): $\delta^H$ 7.79 (d, J=8 Hz, 2H), 7.34 (d, J=8 Hz, 2H), 4.17-4.07 (m, 6H), 3.77-3.62 (m, 60H), 2.45 (s, 3H), 2.17-2.09 (m, 2H), 1.32 (t, J=6.8 Hz, 6H). 13C NMR (100 MHz, CDCl3): $\delta^C$ 144.89, 133.06, 129.92, 128.07, 77.16, 70.81, 70.62, 70.26, 69.34, 68.76, 65.20, 61.77, 61.71, 27.73, 26.34, 21.74, 16.55, 16.49. MALDI-ToF MS (M+K): 1035.13.

6.1.12 Synthesis of diethyl (47-azido-3,6,9,12,15,18,21,24,27,30,33,36,39,42,45-penta decaoxaheptatetracontyl)phosphonate

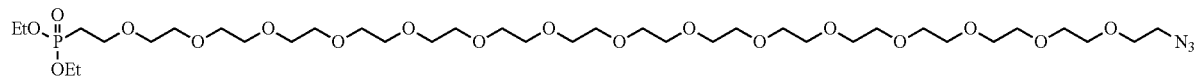 [SMILES: CCOP(=O)(CCOCCOCCOCCOCCOCCOCCOCCOCCOCCOCCOCCOCCOCCOCCOCCN=[N+]=[N-])OCC]

The compound 6l was prepared by general procedure E, starting from compound 6k (0.21 g, 0.21 mmol), sodium azide (NaN$_3$) (0.03 g, 0.4 mmol). The product was obtained as a pale yellow liquid (0.15 g, 0.17 mmol, 85%), Rf=0.45 in 5% MeOH/DCM. The obtained product was used for next step without purification.

6.1.13: Synthesis of Diethyl (47-amino-3,6,9,12,15,18,21,24,27,30,33,36,39,42,45-pentadecaoxaheptatetracontyl)phosphonate

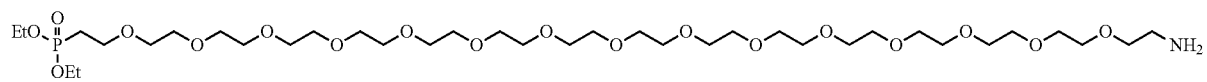 [SMILES: CCOP(=O)(CCOCCOCCOCCOCCOCCOCCOCCOCCOCCOCCOCCOCCOCCOCCOCCN)OCC]

The compound 6m was prepared by general procedure F, starting from compound 6l (0.16 g, 0.17 mmol) and PPh$_3$ (0.072 g, 0.2 mmol). The product obtained was pale yellow liquid (0.14 g, 0.15 mmol 89%), Rf=0.59 in of 2% triethylamine in 5% MeOH/DCM. $^1$H NMR (400 MHz, D$_2$O): $^\delta$H 4.18-4.11 (m, 4H), 3.83-3.63 (m, 61H), 2.30-2.19 (m, 2H), 1.32 (t, J=7.2 Hz, 6H). $^{13}$C NMR (100 MHz, CDCl3): $^\delta$C 69.95, 69.61, 69.47, 69.41, 64.25, 63.41, 63.34, 39.59, 25.80, 24.42, 15.64, 15.58. MALDI-TOF MS(M+K): 880.45.

Example 4.2. Synthesis of G1-G2 Bromide

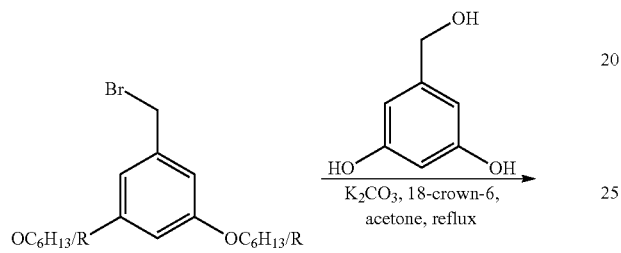

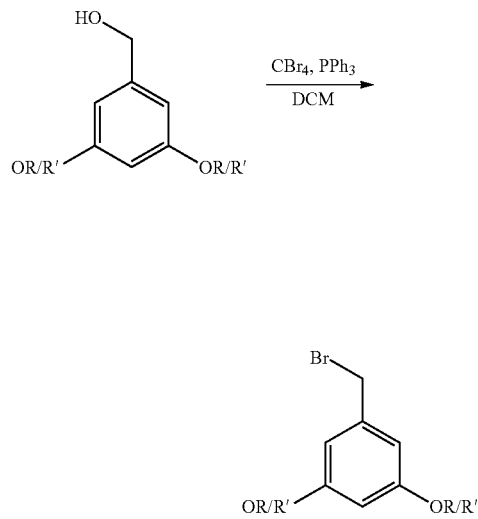

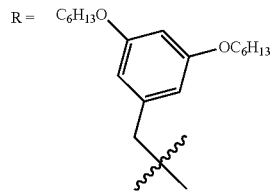

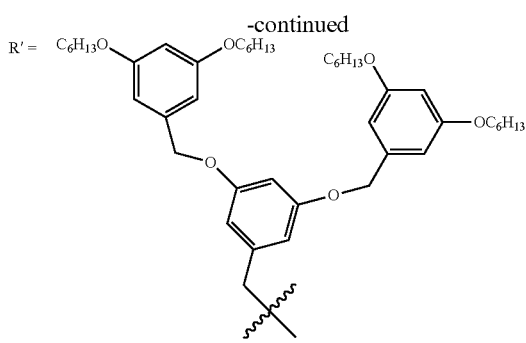

Alkylation of Gn generation bromide by 2,3 dihydroxy benzyl alcohol in presence of K2CO3 resulted in to Gn+1 alcohol. Subsequent bromination of this alcohol gave Gn+1 bromide.

7.1.3.1 Synthesis of Individual Molecules 7.1.3.2 Synthesis of Ethyl 3,5-bis(hexyloxy)benzoate

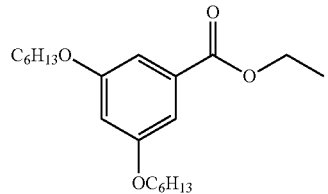

To the oven dried RBF ethyl 3, 5-dihydroxy benzoate (5.0 g, 27 mmol), K$_2$CO$_3$ (11.5 g, 82 mmol), 1-hexyl bromide (11.5 g, 70 mmol) were taken. DMF was added under stirring and heated at 75° C. for 12 hours. Upon completion, reaction mixture was neutralised with 1NHCl solution. Resulting solution was then extracted thrice with ethyl acetate. Combined organic layers was dried over Na$_2$SO$_4$ and concentrated under reduced pressure to get crude product which was then purified using silica gel column chromatography using EtOAC/hexane to afford the compound (9.0 g, 25 mmol 96%) as colourless liquid. Rf=0.46 in 5% ethyl acetate/hexane. $^1$H NMR (400 MHz, CDCl$_3$): $^\delta$H 7.16 (d, J=2.4 Hz, 2H), 6.63 (t, J=2.4 Hz, 1H), 4.34 (q, J=7.2 Hz, 2H), 3.97 (t, J=6.8 Hz, 4H), 1.77 (quint, J=6.8 Hz, 4H), 1.49-1.31 (m, 15H), 0.90 (t, J=6.8 Hz, 6H). $^{13}$C NMR (100 MHz, CDCl$_3$): $^\delta$C 166.67, 160.25, 132.32, 107.74, 106.41, 68.43, 61.21, 31.70, 29.29, 25.83, 22.74, 14.47, 14.18. MALDI-ToFMS: (M+K+) 389.20.

7.1.3.3. Synthesis of (3, 5-bis(hexyloxy)phenyl)methanol

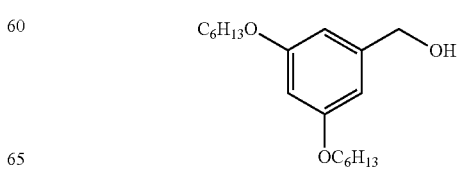

In an oven dried RBF, ethyl 3, 5-bis(hexyloxy)benzoate (40.0 g, 114 mmol) was taken and dissolved in THF with stirring at 0° C. Then lithium aluminium hydride (LAH) (19.0 g, 500 mmol) was added in small portions, maintaining reaction temperature 0° C. After 10 minutes, stirring was continued at RT for 2 hours. Upon completion of reaction, excess of LAH was quenched with dropwise addition of water at 0° C. Resulting mixture was stirred at RT until off-white precipitate forms. Aqueous hydrochloric acid (HCl) (4N) was then added to get clear solution. Resulting content was extracted in ethyl acetate thrice. Combined organic layers was dried over $Na_2SO_4$ and concentrated under reduced pressure to get crude product which was purified using silica gel column chromatography to afford the respective alcohol (30.0 g, 97 mmol, 85%) as colourless liquid. Rf=0.32 in 10% EtOAC/hexane. $^1$H NMR (400 MHz, $CDCl_3$): $\delta$H 6.49 (d, J=2.4 Hz, 2H), 6.38 (t, J=2.4 Hz, 1H), 4.61 (s, 2H), 3.93 (t, J=6.8 Hz, 4H), 1.76 (quint, J=6.4 Hz, 4H), 1.48-1.39 (m, 4H), 1.37-1.30 (m, 8H), 0.91 (t, J=6.8 Hz, 6H). 13C NMR (100 MHz, $CDCl_3$): $\delta$C 160.61, 143.34, 105.13, 100.68, 68.16, 65.52, 31.70, 29.33, 25.84, 22.74, 14.17. HRMS: (M+H+) 308.24.

7.1.3.4 Synthesis of 1-(bromomethyl)-3,5-bis(hexyloxy)benzene

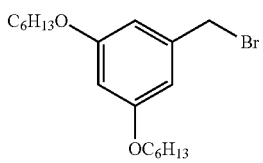

The compound was synthesized starting from above alcohol (5.0 g, 16 mmol), $CBr_4$ (6.1 g, 18 mmol) and $PPh_3$ (4.8 g, 18 mmol) in DCM. The product was obtained as a colourless liquid (6.1 g, 16 mmol, 99%) after purification by silica gel column chromatography using ethyl acetate/hexane as eluent, Rf=0.49 in 5% EtOAC/hexane. $^1$H NMR (400 MHz, $CDCl_3$): $\delta$H 6.52 (d, J=2 Hz, 2H), 6.38 (t, J=2 Hz, 1H), 4.41 (s, 2H), 3.92 (t, J=6.8 Hz, 4H), 1.76 (quint, J=6.4 Hz, 4H), 1.48-1.39 (m, 4H), 1.37-1.30 (m, 8H), 0.91 (t, J=6.8 Hz, 6H). $^{13}$C NMR (100 MHz, CDCl3): $\delta$C 160.53, 139.66, 107.43, 101.50, 68.21, 33.95, 31.70, 29.31, 25.84, 22.74, 14.18; MALDI-ToF MS(M+Na+): 393.11.

7.1.3.5 Synthesis of(3,5-bis((3,5-bis(hexyloxy)benzyl)oxy)phenyl)methanol

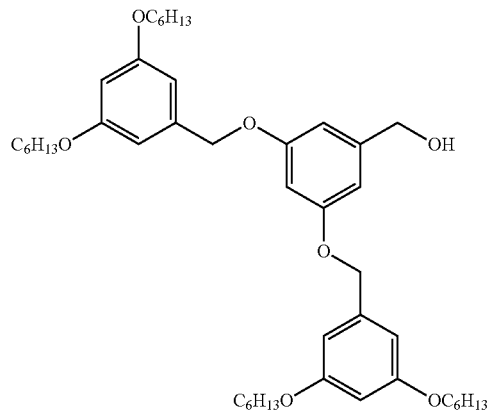

The compound was synthesized starting from 3,5-dihydroxybenzyl alcohol (2.3 g, 16 mmol), G0-bromide (14.0 g, 37 mmol), $K_2CO_3$ (5.2 g, 37 mmol), crown ether (0.70 g, 2 mmol) in acetone. The product was obtained as a yellowish liquid (10.8 g, 15 mmol, 90%) after purification by silica gel column chromatography using EtOAC/hexane as eluent. Rf=0.2 in 5% ethyl acetate/hexane. $^1$HNMR (400 MHz, $CDCl_3$): $\delta$H 6.60 (d, J=2 Hz, 2H), 6.55-6.53 (m, 5H), 6.40 (t, J=2 Hz, 2H), 4.95 (s, 4H), 4.62 (s, 2H), 3.93 (t, J=6.8 Hz, 8H), 1.764 (quint, J=6.8 Hz, 8H), 1.48-1.41 (m, 8H) 1.13-1.29 (m, 16H) 0.91 (t, J=6.8 Hz, 12H). $^{13}$C NMR (100 MHz, CDCl3): $\delta$C 160.60, 160.31, 143.52, 139.14, 105.86, 101.51, 105.89, 70.27, 68.21, 65.48, 31.72, 29.35, 25.82, 22.74, 14.44. MALDI-ToF MS(M+K+): 759.36.

7.1.3.6 Synthesis of 5,5'-(((5-(bromomethyl)-1,3-phenylene) bis(oxy))bis(methylene))bis(1,3-bis(hexyloxy)benzene)

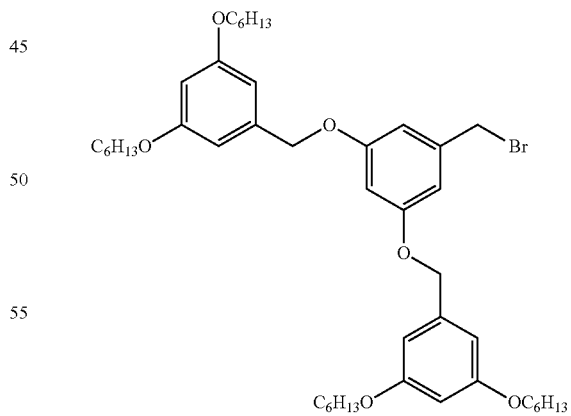

The compound was synthesized from general procedure, starting from G1-alcohol (5.0 g, 7 mmol), $CBr_4$ (3.0 g, 9 mmol) and $PPh_3$ (2.3 g, 9 mmol) in DCM. The product was obtained as a colourless liquid (5.2 g, 6.6 mmol, 97%) after purification by silica gel column chromatography using ethyl acetate/hexane as eluent, Rf=0.5 in 5% EtOAC/hexane. 1H NMR (400 MHz, $CDCl_3$): $\delta$H 6.60 (d, J=2 Hz, 2H), 6.55-6.53 (m, 5H), 6.40 (t, J=2 Hz, 2H), 4.95 (s, 4H), 4.40 (s, 2H), 3.93 (t, J=6.8 Hz, 8H), 1.76 (quint, J=6.8 Hz, 8H), 1.48-1.41 (m, 8H) 1.29-1.35 (m, 16H) 0.91 (t, J=6.8 Hz, 12H). $^{13}$C NMR (100 MHz, CDCl$_3$): $\delta$C160.60, 160.19, 139.84, 138.91, 108.30, 105.89, 102.38, 101.05, 70.37, 68.21, 65.48, 31.72, 29.35, 25.82, 22.74, 14.44. MALDI-ToF MS (M+K+): 823.58

7.1.3.7 Synthesis of (3,5-bis((3,5-bis((3,5-bis (hexyloxy) benzyl)oxy)benzyl)oxy)phenyl)methanol

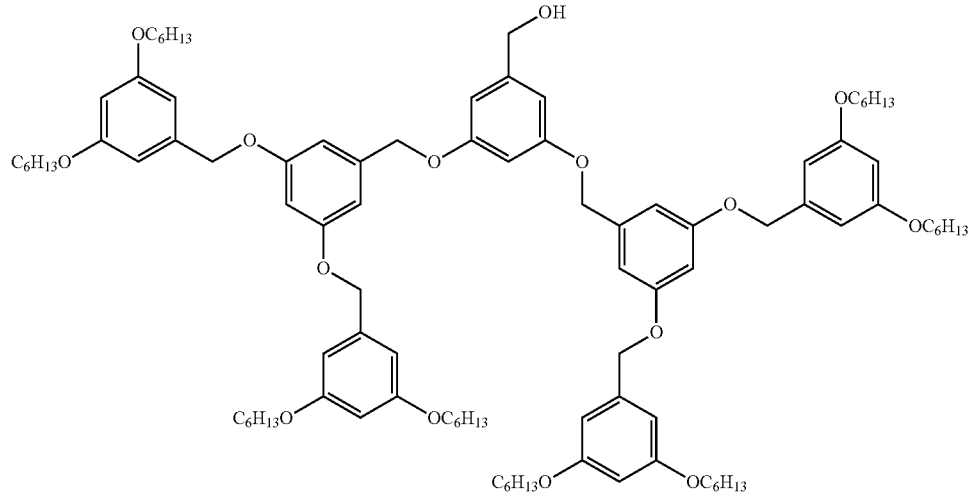

The compound was synthesized starting from 3, 5-dihydroxybenzyl alcohol (0.75 g, 5.3 mmol), G1-bromide (9.8 g, 12 mmol), K$_2$CO$_3$ (1.8 g, 13 mmol), crown ether (0.22 g, 0.8 mmol) in acetone. The product was obtained as a yellowish liquid (8.0 g, 5.0 mmol, 94%) after purification by silica gel column chromatography using EtOAC/hexane as eluent. Rf=0.4 in 25% ethylacetate/hexane. 1H NMR (400 MHz, CDCl$_3$): $\delta^H$ 6.71-6.46 (m, 21H), 4.96 (s, 12H), 4.61 (s, 2H), 3.97 (t, J=6.4 Hz, 16H), 1.81 (quint, J=6.4 Hz, 16H), 1.57-1.32 (m, 48H), 0.98 (m, 24H). 13C NMR (100 MHz, CDCl$_3$): $\delta$C 160.61, 160.24, 160.17, 143.58, 139.31, 139.03, 106.42, 105.83, 101.67, 101.32, 100.92, 70.26, 70.08, 68.18, 65.41, 31.71, 29.34, 25.85, 22.74, 14.19. MALDI-ToF MS (M+K+): 1585.01.

7.1.3.8 Synthesis of 5,5',5'',5'''-((((((5-(bromomethyl)-1,3-phenylene) bis(oxy))bis(methylene))bis (benzene-5,1,3-(triyl)) Tetrakis (oxy)) Tetrakis (methylene)) Tetrakis(1,3-bis(hexyloxy)benzene)

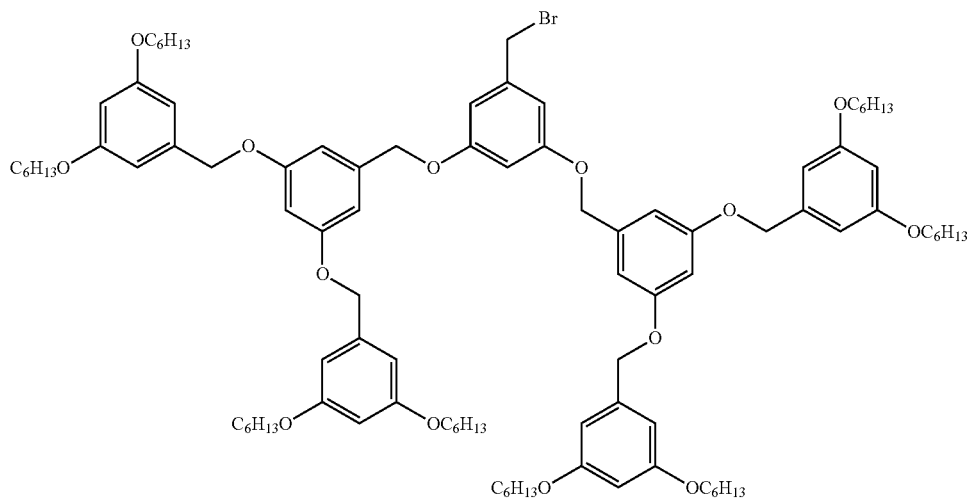

The compound was synthesized, starting from G2-alcohol (7.5 g, 5.0 mmol), CBr$_4$ (2.1 g, 6.3 mmol) and PPh$_3$ (1.7 g, 6.3 mmol) in DCM. The product was obtained as a colourless liquid (7.1 g, 4.4 mmol, 92%) after purification by silica gel column chromatography using ethyl acetate/hexane as eluent, Rf=0.4 in 5% EtOAC/hexane. 1H NMR (400 MHz, CDCl$_3$): $\delta$H 6.69-6.44 (m, 21H), 4.98 (s, 12H), 4.43 (s, 2H), 3.96 (t, J=6.4 Hz, 16H), 1.78 (quint, J=6.4 Hz, 16H), 1.56-1.33 (m, 48H), 0.93 (t, J=6.8 Hz, 24H). $^{13}$C NMR (100 MHz, CDCl$_3$): $\delta$C160.63, 160.27, 160.10, 139.89, 139.02, 108.24, 106.52, 105.84, 102.31, 101.78, 100.95, 77.16, 70.28, 70.19, 68.17, 31.71, 29.35, 25.85, 22.77, 14.16. MALDI-ToF MS (M+K+): 1648.02.

Example 7.2: Synthesis of Photo-Sensitive Macromolecular AABP (19'f)

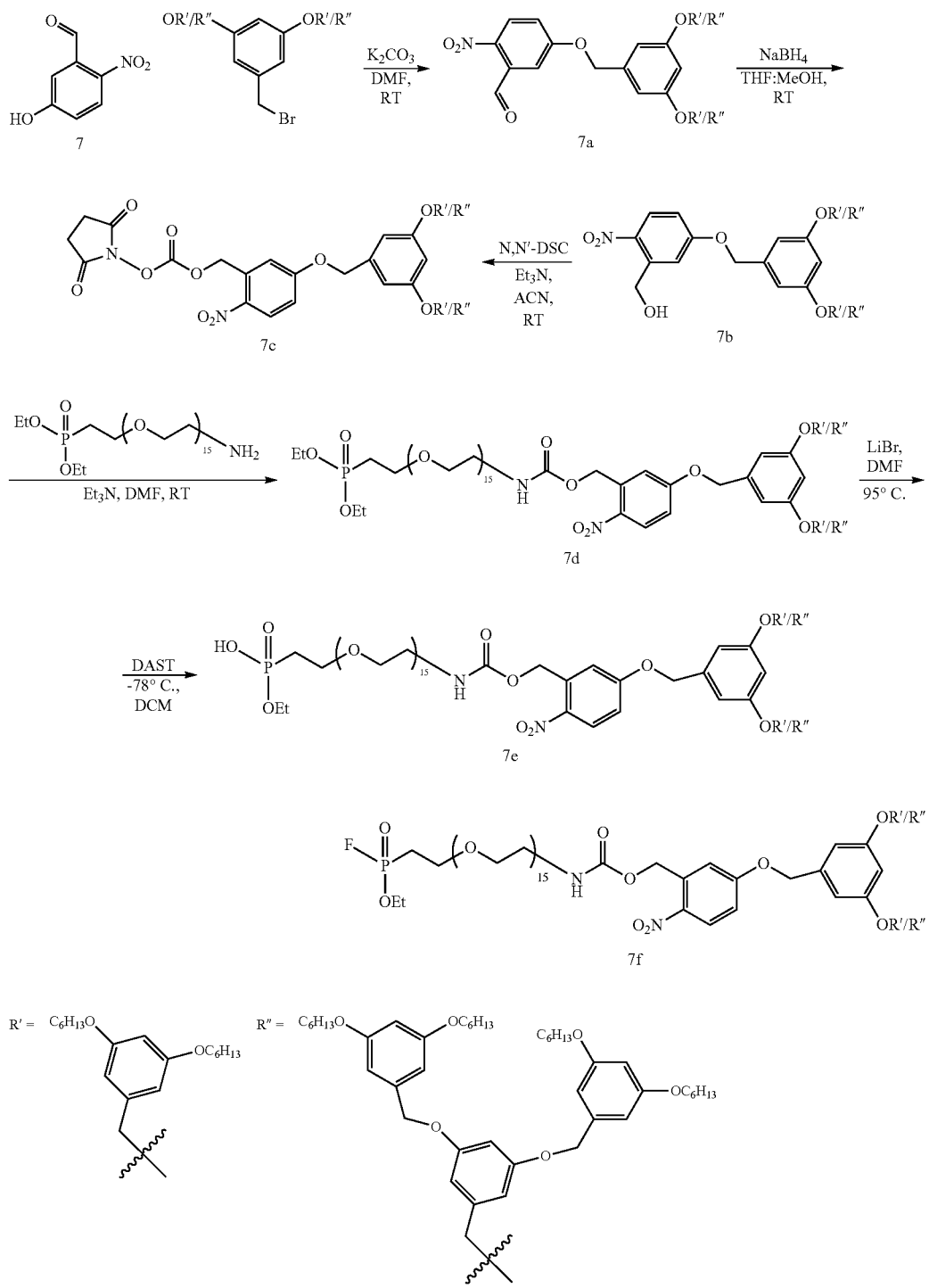

7.2.1: Synthesis of 5-((3,5-bis((3,5-bis(hexyloxy)benzyl)oxy)benzyl)oxy)-2-nitrobenzaldehyde

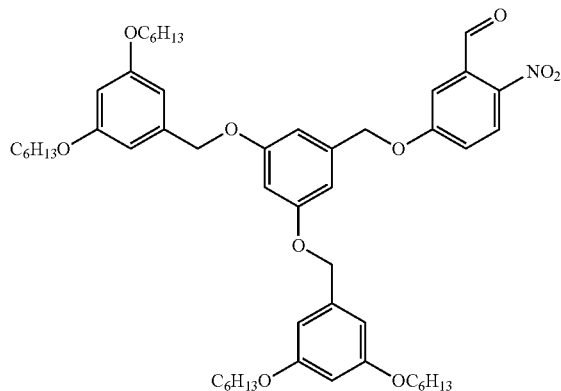

The compound 19a was prepared by general procedure G, starting from 5-hydroxy-2-nitrobenzaldehyde (0.7 g, 4 mmol), K2CO3 (0.7 g, 5 mmol) and G1 bromide (3.3 g, 4.2 mmol). The product obtained as pale solid (3.3 g, 3.8 mmol, 90%), Rf=0.52 in 20% EtOAc/hexane. 1H NMR (400 MHz, CDCl$_3$): $^\delta$H 10.47 (s, 1H), 8.11 (d, J=8.9 Hz, 1H), 7.37 (d, J=8.9, 2.8 Hz, 1H), 7.14 (d, J=2.8 Hz, 1H), 6.61-6.40 (m, 9H), 5.12 (s, 2H), 4.96 (s, 4H), 3.93 (t, J=6.4 Hz, 4H), 1.77-1.53 (m, 8H), 1.53-1.26 (m, 24H), 0.91 (t, J=7.2 Hz, 12H). $^{13}$C NMR (100 MHz, CDCl$_3$): 188.56, 163.05, 160.65, 160.29, 142.48, 138.83, 137.35, 134.40, 127.23, 119.27, 114.52, 106.37, 105.78, 100.85, 70.95, 70.30, 70.01, 68.20, 31.71, 29.34, 25.85, 22.73, 14.18. MALDI-TOF MS (M+K): 908.31.

7.2.2: Synthesis of (5-((3,5-bis((3,5-bis(hexyloxy)benzyl)oxy)benzyl)oxy)-2-nitrophenyl)methanol

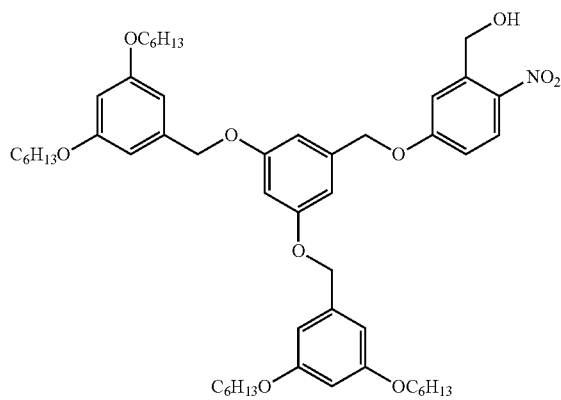

The compound 19b was prepared by general procedure H, starting from compound 19a (0.9 g, 1 mmol), NaBH$_4$ (0.09 g, 1.5 mmol). The product obtained as a pale yellow solid (0.8 g, 0.9 mmol, 90%), Rf=0.20 in 20% EtOAc/hexane. $^1$H NMR (400 MHz, CDCl$_3$): $^\delta$H 8.13 (d, J=8.9 Hz, 1H), 7.34 (d, J=8.9, 2.8 Hz, 1H), 7.18 (d, J=2.8 Hz, 1H), 6.62-6.41 (m, 9H), 5.14 (s, 2H), 4.94 (s, 4H), 3.93 (t, J=6.4 Hz, 4H), 1.78-1.52 (m, 8H), 1.53-1.26 (m, 24H), 0.90 (t, J=7.2 Hz, 12H). MALDI-TOF MS (M+K): 910.43.

7.2.3: Synthesis of 5-((3,5-bis((3,5-bis(hexyloxy)benzyl)oxy)benzyl)oxy)-2-nitrobenzyl (2,5-dioxopyrrolidin-1-yl) carbonate

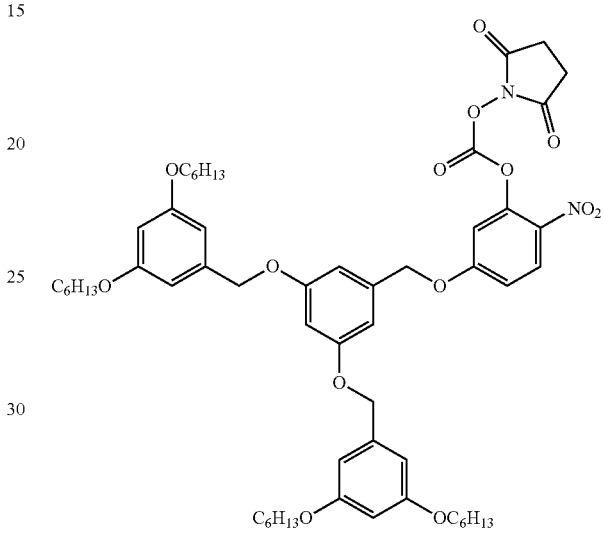

The compound 19c was prepared by general procedure I, starting from compound 19b (0.75 g, 0.8 mmol) and N,N'-DSC (3.3 g, 12 mmol) and, Et3N (1.30 g, 12 mmol). The product obtained as a pale yellow solid (0.40 g, 0.4 mmol, 50%), Rf=0.18 in 25% EtOAc/hexane. 1H NMR (400 MHz, CDCl3): $^\delta$H 8.21 (d, J=8.9 Hz, 1H), 7.19 (dd, J=8.9, 2.8 Hz, 1H), 6.96 (d, J=2.8 Hz, 1H), 6.69-6.40 (m, 12H), 5.80 (s, 2H), 5.17 (s, 2H), 3.93 (t, J=6.4 Hz, 4H), 2.78 (s, 4H), 1.81-1.72 (m, 10H), 1.47-1.28 (m, 35H), 0.9 (t, J=7.2 Hz, 18H). $^{13}$C NMR (100 MHz, CDCl$_3$): 160.62, 138.91, 113.99, 106.33, 105.82, 100.86, 70.28, 68.23, 51.98, 31.70, 29.33, 25.84, 25.52, 25.22, 22.78, 20.20, 14.22, 13.73. MALDI-TOF MS (M+K):1053.73.

7.2.4: Synthesis of 5-((3,5-bis((3,5-bis(hexyloxy)benzyl)oxy)benzyl)oxy)-2-nitrobenzyl (47-(diethoxyphosphoryl)-3, 6, 9, 12, 15, 18, 21, 24, 27, 30, 33, 36, 39, 42,45-penta Deca Oxa Heptatetracontyl)carbamate

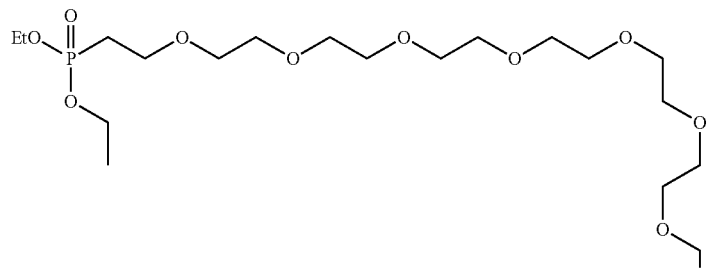

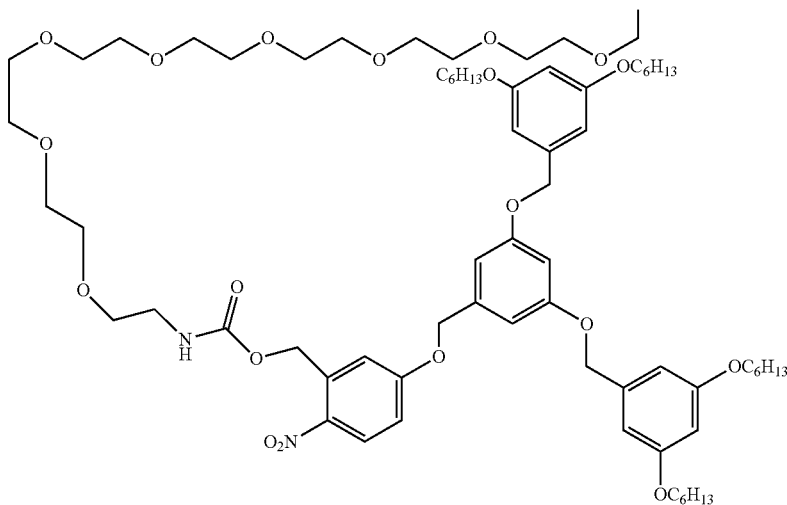

The compound 19'd was prepared by general procedure J, starting from compound 19'c (0.6 g, 0.6 mmol), compound 5m (0.4 g, 0.0.4 mmol) and, Et3N (0.06 g, 0.6 mmol). The obtained product was pale yellow liquid (0.35 g, 0.2 mmol, 35%), Rf=0.40 in 5% MeOH/DCM. $^1$H NMR (400 MHz, CDCl$_3$) 8.08 (d, J=8.9 Hz, 1H), 7.10 (dd, J=8.9, 2.8 Hz, 1H), 6.82 (d, J=2.8 Hz, 1H), 6.57-6.33 (m, 12H), 5.46 (s, 2H), 5.23 (s, 2H), 4.88 (s, 2H), 3.85 (t, J=6.4 Hz, 8H), 3.76-3.46 (m, 67H), 2.25-2.11 (m, 2H), 1.72-1.61 (m, 12H), 1.46-1.14 (m, 62H), 0.82 (t, J=6.8 Hz, 18H). $^{13}$C NMR (100 MHz, CDCl$_3$): 162.49, 160.42, 138.67, 127.78, 113.14, 106.31, 105.61, 101.68, 100.59, 70.43, 70.21, 70.04, 69.78, 67.95, 36.08, 31.76, 31.48, 31.31, 29.56, 29.11, 25.63, 22.59, 14.04. MALDI-TOF MS (M+K): 1777.10.

7.2.4: Synthesis of 5-((3,5-bis((3,5-bis(hexyloxy) benzyl)oxy)benzyl)oxy)-2-nitrobenzyl (47-(ethoxy (hydroxy)phosphoryl)-3, 6, 9, 12, 15, 18, 21, 24, 27, 30, 33, 36, 39, 42, 45-penta Deca Oxa Hepta Tetracontyl) Carbamate

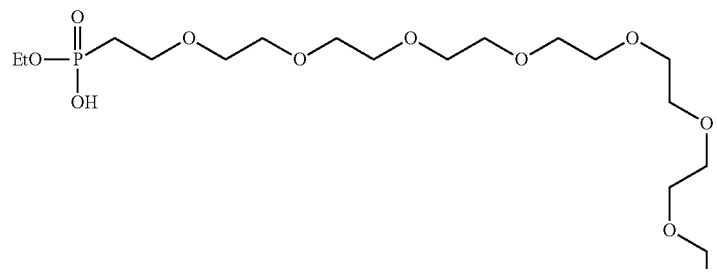

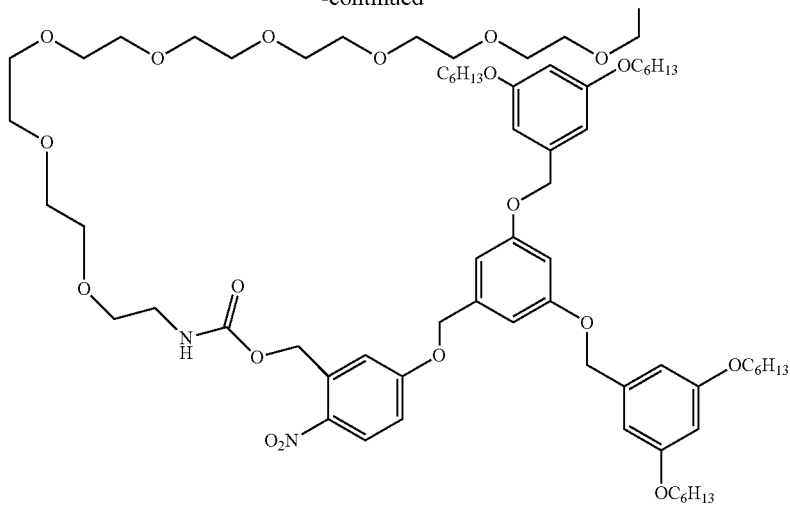
The compound 19'e was prepared by general procedure K, starting from compound 19'd (0.25 g, 0.14 mmol) and, LiBr (0.25 g, 2 mmol) was added. The obtained product was carried to the next step without further purification.
7.2.5: Synthesis of 5-((3,5-bis((3,5-bis(hexyloxy)benzyl)oxy)benzyl)oxy)-2-nitrobenzyl (47-(ethoxyfluorophosphoryl)-3, 6, 9, 12, 15, 18, 21, 24, 27, 30, 33, 36, 39,42,45-penta decaoxaheptatetracontyl)carbamate
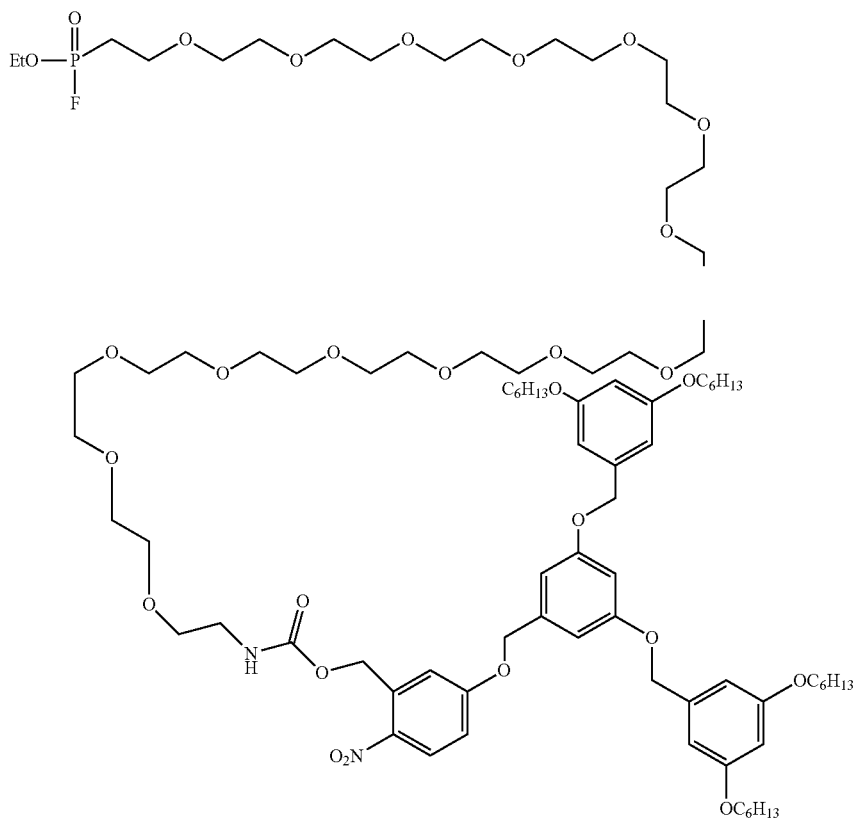

The compound 19'f was prepared by general procedure L, starting from compound 19'e (0.1 g, 0.050 mmol), DAST (0.040 g, 0.2 mmol). The product was utilized for conjugation without further purification. $^{19}$F NMR (400 MHz, CDCl$_3$): $\delta$F −59.91, −62.74. MALDI-TOF MS (M+K): 1753.10.

7.3: Synthesis of 5-((3,5-bis((3,5-bis((3,5-bis(hexyloxy)benzyl)oxy)benzyl)oxy)benzyl)oxy)-2-nitro Benzaldehyde (20'a)

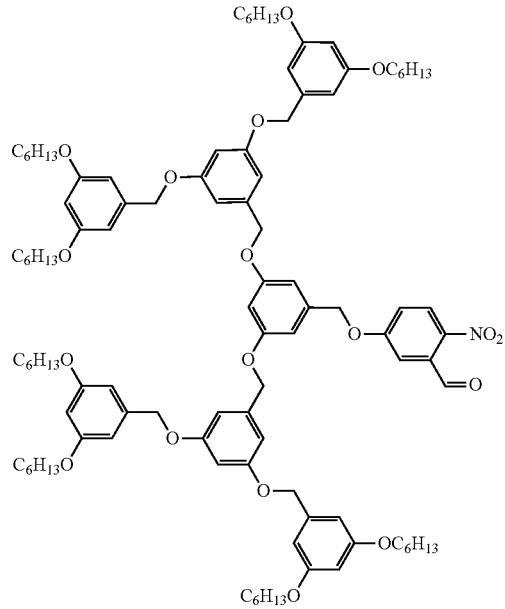

The compound 20'a was prepared by general procedure G, starting from 5-hydroxy-2-nitrobenzaldehyde(0.018 g, 0.10 mmol), K$_2$CO$_3$ (0.02 g, 0.12 mmol) and G2 bromide (0.17 g, 0.10 mmol). The product obtained as pale solid (0.10 g, 0.06 mmol, 65%), Rf=0.52 in 20% EtOAc/hexane. $^1$H NMR (400 MHz, CDCl$_3$): $\delta$H 10.46 (s, 1H), 8.11 (d, J=8.9 Hz, 1H), 7.37 (d, J=8.9, 2.8 Hz, 1H), 7.12 (d, J=2.8 Hz, 1H), 6.65-6.39 (m, 21H), 5.13 (s, 2H), 4.97-4.94 (m, 12H), 3.93 (t, J=6.4 Hz, 16H), 1.83-1.70 (m, 16H), 1.46-1.32 (m, 52H), 0.90 (t, J=7.2 Hz, 24H). $^3$C NMR (100 MHz, CDCl$_3$): 188.54, 163.02, 160.62, 160.27, 138.95, 134.39, 127.34, 114.43, 70.91, 70.18, 68.17, 31.70, 29.33, 25.85, 22.73, 14.18. MALDI-TOFMS (M+K): 1734.21

7.3.1 Synthesis (5-((3,5-bis((3,5-bis((3,5-bis (hexyloxy) benzyl) oxy) benzyl)oxy)benzyl)oxy)-2-nitro phenyl) Methanol (20'b)

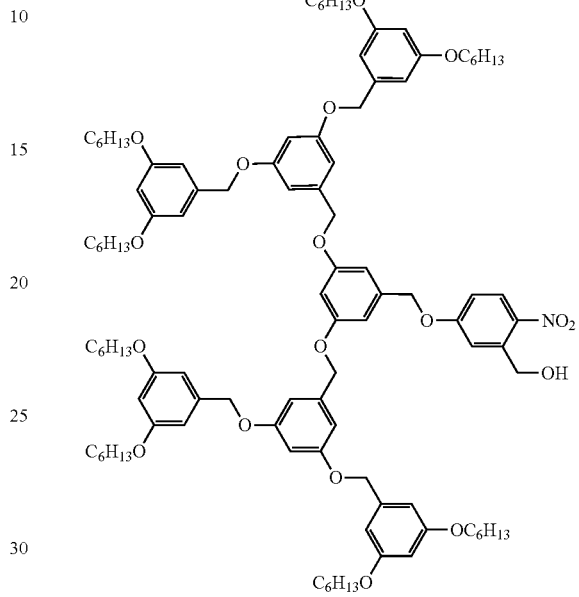

The compound 20'b was prepared by general procedure H, starting from compound 20'a (0.13 g, 0.09 mmol), NaBH$_4$ (0.045 g, 1.1 mmol). The product obtained as a pale yellow solid (0.090 g, 0.056 mmol, 70%), Rf=0.20 in 20% EtOAc/hexane. 1H NMR (400 MHz, CDCl$_3$): $\delta$H 8.11 (d, J=8.9 Hz, 1H), 7.14 (dd, J=8.9, 2.8 Hz, 1H), 6.86 (d, J=2.8 Hz, 1H), 6.62-6.38 (m, 21H), 5.61 (s, 2H), 5.03 (s, 2H), 4.90 (s, 12H), 3.90 (t, J=6.4 Hz, 15H), 1.77-1.70 (m, 16H), 1.45-1.25 (m, 50H), 0.88 (t, J=7.2 Hz, 24H). $^{13}$CNMR (100 MHz, CDCl$_3$): 160.64, 160.28, 138.96, 105.89, 100.92, 99.96, 77.16, 70.31, 68.21, 31.72, 29.35, 25.86, 22.75, 14.19. MALDI-TOF MS (M+K): 1735.30.

7.3.2 Synthesis of 5-((3,5-bis((3,5-bis((3,5-bis (hexyloxy) benzyl) oxy) benzyl)oxy)benzyl)oxy)-2-nitro Benzyl (2,5-dioxopyrrolidin-1-yl) Carbonate

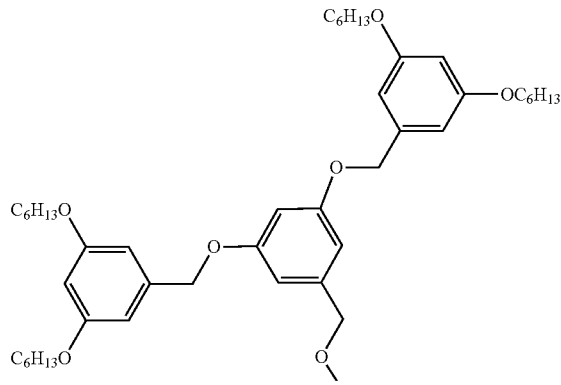

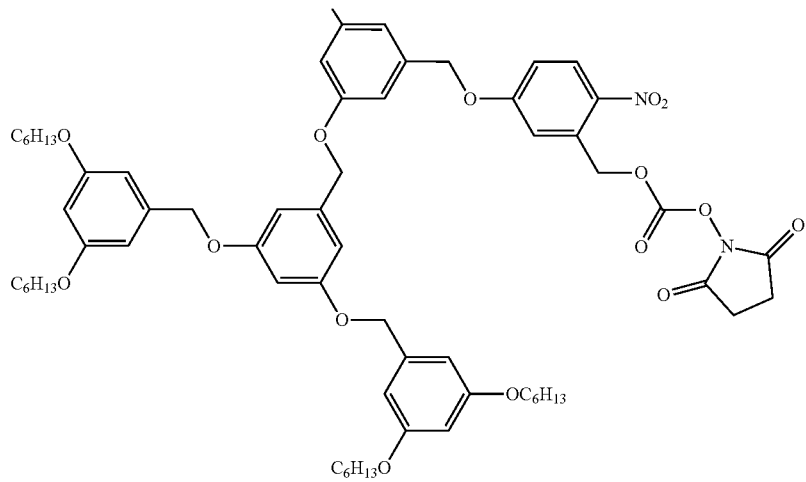

The compound 20'c was prepared by general procedure I, starting from compound 20'b (0.048 g, 0.03 mmol), N,N'-DSC (0.2 g, 0.80 mmol) and Et3N (0.10 g, 0.1 mmol). The product obtained as a pale yellow solid (0.03 g, 0.019 mmol, 66%), Rf=0.18 in 25% EtOAc/hexane. $^1$HNMR (400 MHz, CDCl$_3$):$^\delta$H 8.20 (d, J=8.9 Hz, 1H), 7.18 (dd, J=8.9, 2.8 Hz, 1H), 6.98 (d, J=2.8 Hz, 1H), 6.70-6.40 (m, 21H), 5.80 (s, 2H), 4.98-4.94 (m, 12H), 3.93 (t, J=6.4 Hz, 16H), 2.71 (s, 4H), 1.84-1.68 (m, 18H), 1.47-1.22 (m, 56H), 0.89 (t, J=7.2 Hz, 27H). $^{13}$C NMR (100 MHz, CDC$_{l3}$): 168.57, 163.39, 160.59, 160.30, 160.21, 139.44, 139.18, 138.94, 106.44, 106.20, 105.83, 101.55, 100.84, 70.60, 70.22, 70.07, 69.19, 68.14, 31.67, 29.30, 25.82, 22.70, 14.14.

7.3.3 Synthesis of 5-((3,5-bis((3,5-bis((3,5-bis (hexyloxy)benzyl)oxy)benzyl)oxy)benzyl)oxy)-2-nitrobenzyl (47-(diethoxy phosphoryl)-3,6,9,12,15, 18,21,24,27,30,33,36,39,42,45-penta Deca Oxa Hepta Tetracontyl) Carbamate

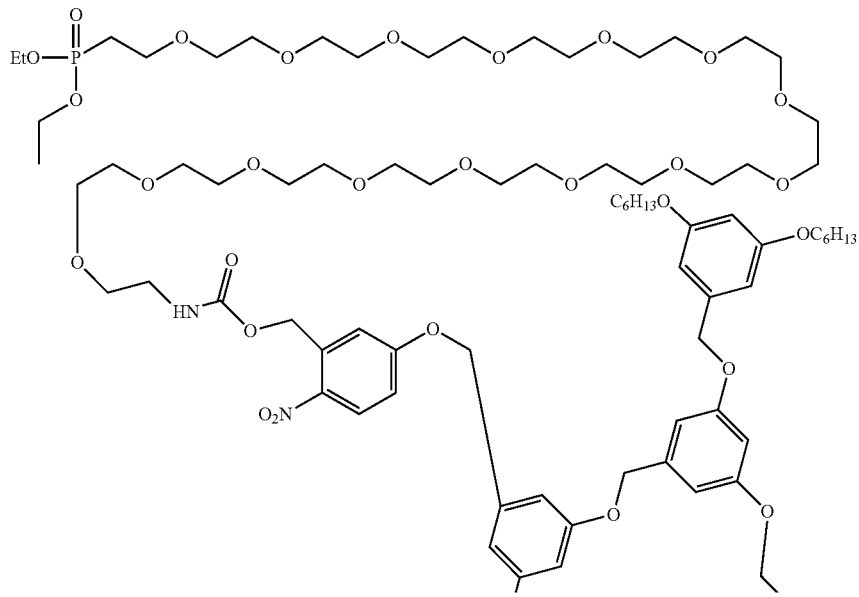

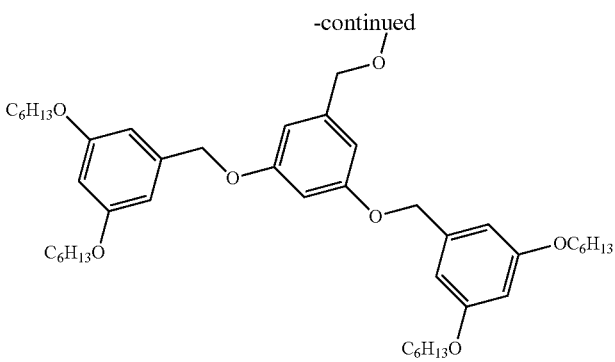

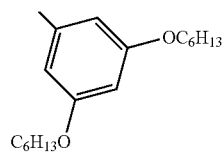

The compound 20'd was prepared by general procedure J, starting from compound 20'c (0.10 g, 0.05 mmol), compound 5m (0.04 g, 0.05 mmol) and, Et₃N (0.005 g, 0.05 mmol). The product obtained was pale yellow liquid (0.1 g, 0.04 mmol, 60%), Rf=0.40 in 5% MeOH/DCM. 8.15 (d, J=8.9 Hz, 1H), 7.17 (dd, J=8.9, 2.8 Hz, 1H), 6.91 (d, J=2.8 Hz, 1H), 6.66-6.39 (m, 27H), 5.53 (s, 2H), 5.08 (s, 2H), 5.00-4.86 (m, 16H), 4.14-4.06 (m, 4H), 3.90 (t, J=6.4 Hz, 20H), 3.75-3.49 (m, 77H), 2.19-2.06 (m, 2H), 1.86-1.66 (m, 22H), 1.50-1.18 (m, 88H), 0.89 (t, J=7.2 Hz, 36H). $^{13}$C NMR (100 MHz, CDCl₃): 160.59, 160.19, 138.92, 106.63, 105.84, 100.85, 70.61, 70.25, 70.16, 68.15, 65.19, 61.81, 31.67, 29.79, 29.30, 25.82, 22.70, 16.55, 16.41, 14.15. MALDI-TOF MS (M+K): 2602.39

7.3.4: Synthesis of 5-((3,5-bis((3,5-bis((3,5-bis (hexyloxy) benzyl) oxy) benzyl) oxy) benzyl)oxy)-2-nitrobenzyl (47-(ethoxy(hydroxy)phosphoryl)-3, 6, 9, 12, 15, 18, 21, 24,27,30,33,36,39,42,45-penta Deca Oxaheptatetracontyl)carbamate

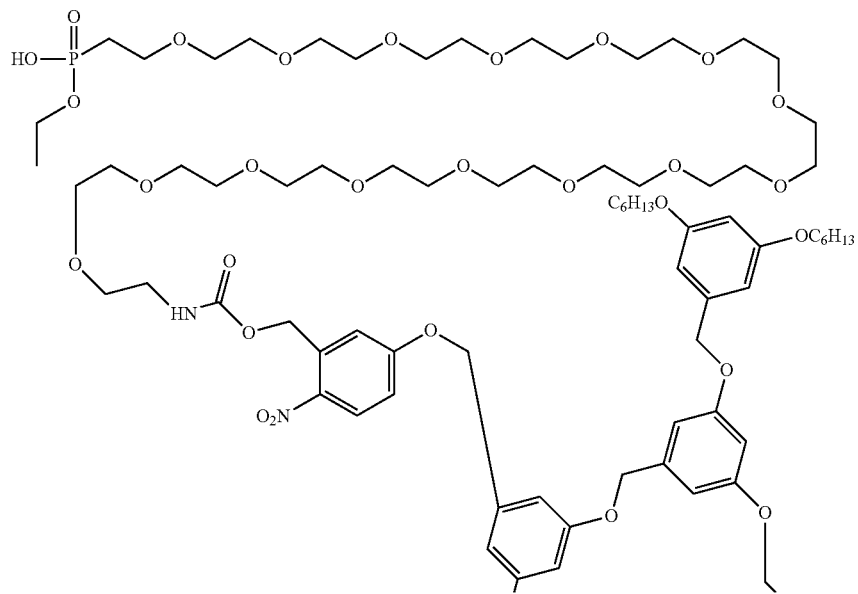

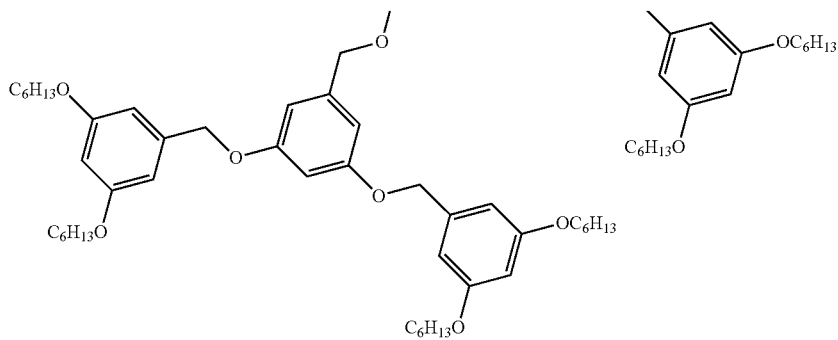

The compound 20'e was prepared by general procedure K, starting from compound 20'd (0.070 g, 0.02 mmol) and, LiBr (0.040 g, 0.5 mmol). The obtained product was carried to the next step without further purification.

7.3.5: Synthesis of 5-((3,5-bis((3,5-bis((3,5-bis(hexyloxy)benzyl)oxy)benzyl)oxy)benzyl)oxy)-2-nitrobenzyl (47-(ethoxyfluorophosphoryl)-3,6,9,12,15,18,21,24,27,30,33,36,39,42,45-pentadecaoxaheptatetracontyl)carbamate

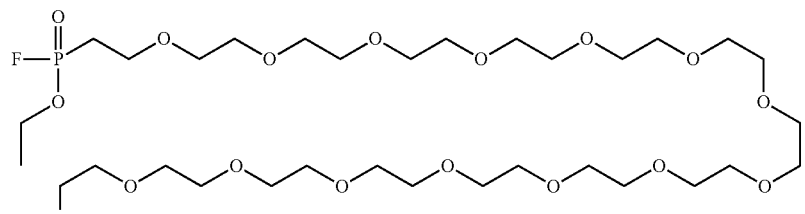

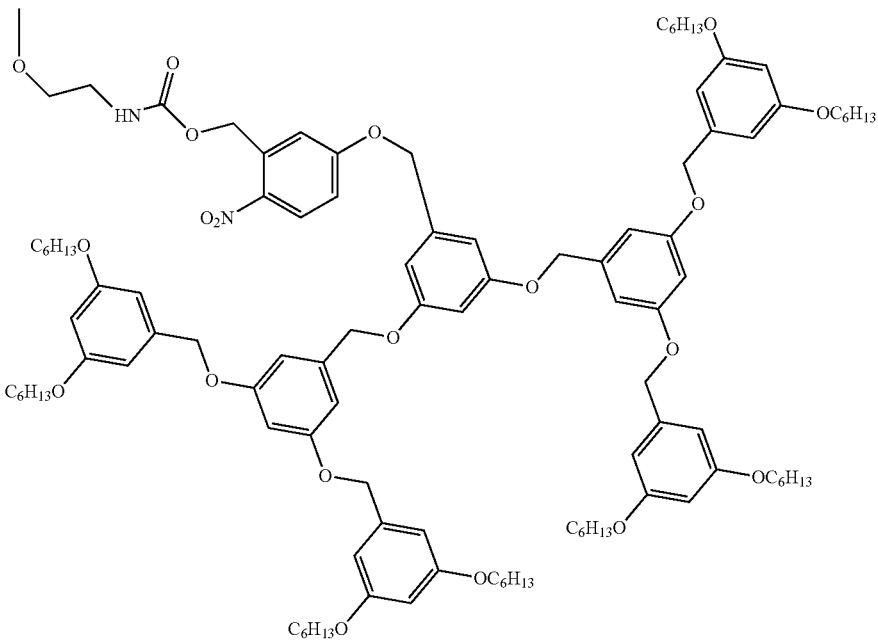

The compound 20'f was prepared by general procedure L, starting from compound 20'e (0.04 g, 0.01 mmol), DAST (0.01 g, 0.05 mmol). The obtained product was utilized for conjugation without further purification. $^{19}$F NMR (400 MHz, CDCl$_3$): $\delta$F −59.91, −62.74.

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:
1. Stimuli-sensitive protein conjugates that make supramolecular assemblies of general Formula (IA);

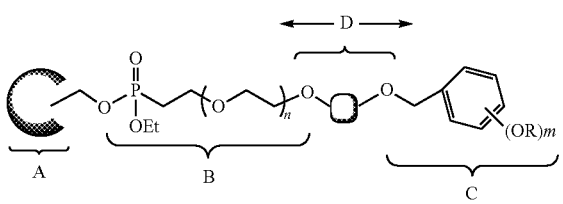

comprising;
a hydrophilic protein head group (A) with a length of up to 500 amino acids selected from the group consisting of serine proteases, cysteine proteases, aspartic proteases, metalloproteases, and mixtures thereof;

a hydrophilic spacer (B) comprising phosphonate ester of oligoethylene glycol;

hydrophobic tails or dendrons (C) wherein 'R' represents C4-C20 unsubstituted or substituted straight, branched, cyclic or acyclic aliphatic, aromatic or alkyl or alkoxy aryl moieties; linear or branched polymers, dendrimers, hydrophobic peptides or proteins;

the stimuli-sensitive moiety (D) that can be located anywhere in the supramolecular protein assembly, wherein the stimuli-sensitive probe (D) is selected from the group consisting of:
(i) a photo-sensitive nitrobenzyl functionalized oligoethylene glycol (OEG) probe
(ii) a pH-sensitive hydrazine functionalized oligoethylene glycol (OEG) probe; and
(iii) a multi-stimuli sensitive nitrobenzyl functionalized cetylethylene glycol probe;

'n' represents the integer 1 to 20;

'm' represents the integer 1 to 4;

wherein said stimuli-sensitive protein conjugate disassembles in response to exogenous or endogenous stimuli or combination thereof.

2. The stimuli-sensitive protein conjugate as claimed in claim 1, wherein said protein conjugate is photosensitive of formula (IA');

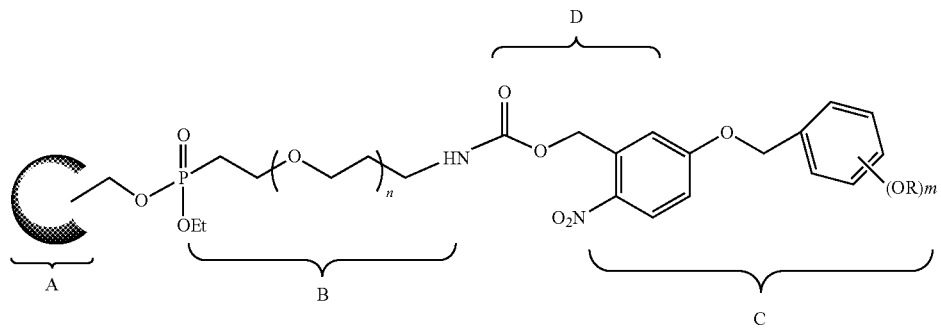

which comprises;
a hydrophilic protein head group (A) with a length of up to 500 amino acids selected from the group consisting of serine proteases, cysteine proteases, aspartic proteases, metalloproteases, and mixtures thereof;
a hydrophilic spacer (B) comprising phosphonate ester of oligoethylene glycol;
hydrophobic tails or dendrons (C) wherein 'R' represents C4-C20 unsubstituted or substituted straight, branched, cyclic or acyclic aliphatic, aromatic or alkyl or alkoxy aryl moieties; linear or branched polymers, dendrimers, hydrophobic peptides or proteins;
the photosensitive 2-nitrobenzyl moiety (D) located between the hydrophilic portion (B) and the hydrophobic tail (C);
'n' represents the integer 1 to 20;
'm' represents the integer 1 to 4;
wherein said supramolecular protein assembly disassembles upon exposure to light/photoirradiation.

3. The stimuli-sensitive protein conjugate as claimed in claim 1, wherein said protein conjugate is pH sensitive of formula (IA");

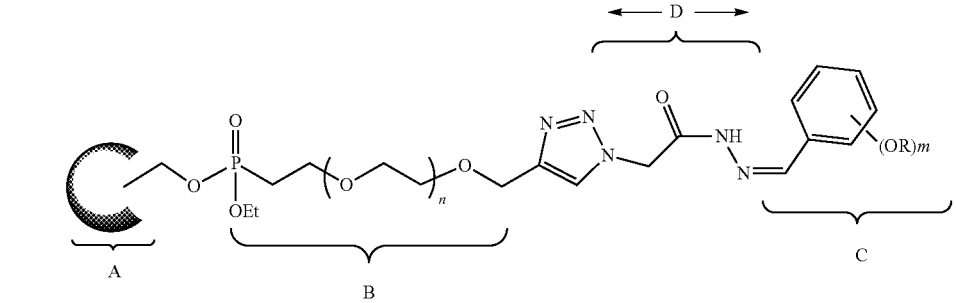

which comprises;
a hydrophilic protein head group (A) with a length of up to 500 amino acids selected from the group consisting of serine proteases, cysteine proteases, aspartic proteases, metalloproteases, and mixtures thereof;
a hydrophilic spacer (B) comprising phosphonate ester of oligoethylene glycol;
hydrophobic tails or dendrons (C) comprising substituted benzyl ether wherein 'R' represents C4-C20 unsubstituted or substituted straight, branched, cyclic or acyclic aliphatic, aromatic or alkyl or alkoxy phenyl moieties;
the pH sensitive hydrazine moiety (D) located between the hydrophilic portion (B) and the hydrophobic tail (C);
'n' represents the integer 1 to 20;
'm' represents the integer 1 to 4;
wherein said supramolecular protein assembly disassembles in response to pH change.

4. The stimuli-sensitive protein conjugate as claimed in claim 1, wherein said protein conjugate is sensitive to multiple stimuli of formula (IA''');

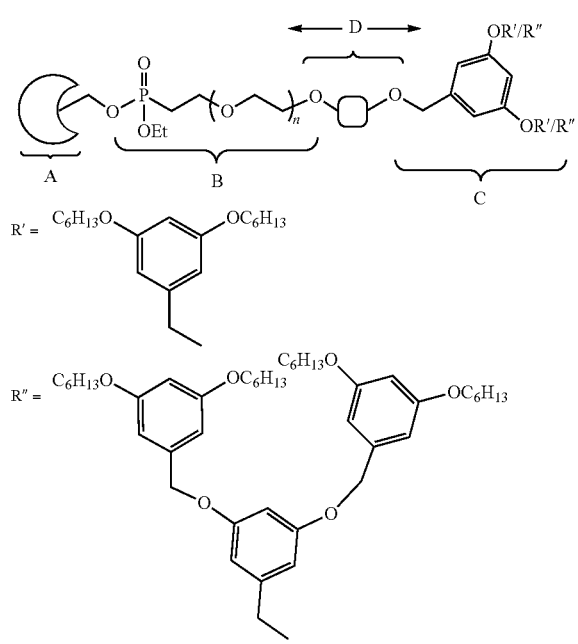

which comprises;
a hydrophilic protein head group (A) with a length of up to 500 amino acids selected from the group consisting of serine proteases, cysteine proteases, aspartic proteases, metalloproteases, and mixtures thereof;
a hydrophilic spacer (B) comprising phosphonate ester of oligoethylene glycol;
hydrophobic Gn dendron (C) represented by groups R' and R";
the multi stimuli-sensitive nitrobenzyl functionalized cetylethylene glycol moiety moiety (D) located between the hydrophilic portion (B) and the hydrophobic dendrimer tail (C);
'n' is the integer 1 to 20;
wherein said supramolecular protein assembly disassembles in response to any exogenous or endogenous stimuli.

5. A stimuli-sensitive protein conjugate selected from the group consisting of;
(i) a conjugate formed by conjugating trypsin with the photosensitive probe 5-((3,5-bis(dodecyloxy)benzyl)oxy)-2-nitrobenzyl(2-(2-(ethoxyfluoro phosphoryl) ethoxy) ethyl) carbamate;
(ii) a conjugate formed by conjugating trypsin with the pH sensitive probe ethyl (E)-(2-(2-((1-(2-(3,5-bis(dodecyloxy)benzylidene)hydrazine-1-carbonyl)-1H-I,2,3-triazol-4-yl) methoxy)ethoxy) ethyl) phosphonofluoridate;
(iii) a conjugate formed by conjugating chymotrypsin with the photosensitive probe 5-((3,5-bis((3,5-bis(hexyloxy)benzyl)oxy)benzyl)oxy)-2-nitrobenzyl (47-(ethoxy fluoro phosphoryl)-3,6,9,12,15,18,21,24,27,30,33,36,39,42,45-penta deca oxa hepta tetra contyl) carbamate; and
(iv) a conjugate formed by conjugating chymotrypsin with the photosensitive probe 5-((3,5-bis((3,5-bis((3,5-bis(hexyloxy)benzyl)oxy)benzyl)oxy)benzyl)oxy)-2-nitrobenzyl (47-(ethoxyfluoro phosphoryl)-3,6,9,12,15,18,21,24,27,30,33,36,39,42,45-pentadecaoxaheptatetracontyl) carbamate.

6. A supramolecular protein assembly in the form of a particle comprising the protein conjugate of claim 1, wherein the particle has a particle size in the range of 10-100 nm.

7. A composition comprising;
(i) an active pharmaceutical ingredient in association with the protein conjugate of claim 1; and
(ii) at least one component selected from the group consisting of an excipient, a surfactant, an acid, a base, a buffer system, an inorganic particle, a UV absorber, and a mixture thereof.

8. The process for obtaining the supramolecular protein assemblies of claim 1, comprising:
(A) providing a stimuli sensitive amphiphilic activity based probe composed of a flurophosphonate (FP) as a reactive group, hydrophilic linker, hydrophobic dendrimer or tails, and stimuli-sensitive group, wherein the stimuli-sensitive group is selected from the group consisting of:
(i) a photo-sensitive nitrobenzyl functionalized oligoethylene glycol (OEG);
(ii) a PH-sensitive hydrazine functionalized oligoethylene glycol; and
(iii) a multi-stimuli sensitive nitrobenzyl functionalized cetylethylene glycol;
(B) separately providing a protein in solution;
(C) homogenizing the stimuli sensitive amphiphilic activity-based probes (AABP) provided in (A) in Triton X-100 and sodium phosphate buffer at pH 7.4 followed by addition of the protein solution provided in (B) to the homogenized solution in sodium phosphate buffer at pH 7.4 and allowing said components to react together;
(D) removing Triton X-100 from the mixture Produced in step (ii) using ion exchange chromatography (IEX) and eluting the native and supramolecular protein complex using eluting buffer solution;
(E) removing the native protein in high salt concentration using size exclusion chromatography followed by desalting and lyophilizing to obtain pure protein conjugate of formula (IA).

9. The process as claimed in claim 8, wherein the stimuli sensitive protein conjugate comprises;
   (i) a protein conjugate made from the photo-sensitive probe 5-((3,5-bis(dodecyloxy)benzyl)oxy)-2-nitrobenzyl(2-(2-(ethoxyfluoro phosphoryl) ethoxy) ethyl) carbamate (9) conjugated to a protein;
   (ii) a protein conjugate made from the pH sensitive probe ethyl (E)-(2-(2-((1-(2-(3,5-bis(dodecyloxy)benzylidene)hydrazine-I-carbonyl)-IH-I,2,3-triazol-4-yl) methoxy) ethoxy) ethyl) phosphonofluoridate (17') conjugated to a protein;
   (iii) a protein conjugate made from the multi stimuli-sensitive probe selected from 5-((3,5-bis((3,5-bis(hexyloxy)benzyl)oxy)benzyl)oxy)-2-nitrobenzyl (47-(ethoxyfluorophosphoryl)-3,6,9,12,15,18,21,24,27,30,33,36,39,42,45-penta deca oxa hepta tetra contyl) carbamate (19'f) and 5-((3,5-bis((3,5-bis((3,5-bis(hexyloxy)benzyl)oxy)benzyl) oxy)benzyl)oxy)-2-nitrobenzyl (47-(ethoxyfluorophosphoryl)-3,6,9,12,15,18,21,24,27,30,33,36,39,42,45-pentadecaoxaheptatetracontyl)carbamate (20'f) conjugated to a protein.

10. The process for preparing the photosensitive probe 5-((3,5-bis(dodecyloxy)benzyl)oxy)-2-nitrobenzyl(2-(2-(ethoxyfluoro phosphoryl) ethoxy) ethyl) carbamate (9) comprising;
   (i) reacting 3-hydroxybenzaldehyde with ethyl chloroformate in anhydrous pyridine to obtain ethyl (3-formylphenyl) carbonate (1); nitrating the compound (1) with nitrating agent at 0° C. to obtain nitro compound (2)

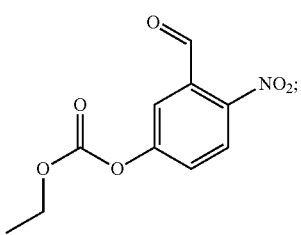

2

(ii) hydrolysing nitro compound (2) in presence of base to obtain phenolic compound (3)

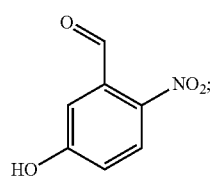

3 reacting compound (3) with di-substituted benzyl bromide

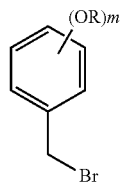

in presence of base to obtain compound (4)

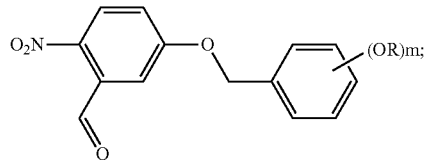

4

(iii) reducing compound (4) in presence of alkali metal borohydride in solvent mixture to yield alcohol (5)

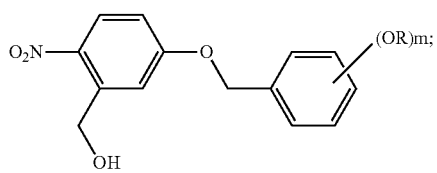

5 esterifying alcohol (5) with N,N'-disuccinimidyl carbonate in presence of base and solvent to obtain ester (6)

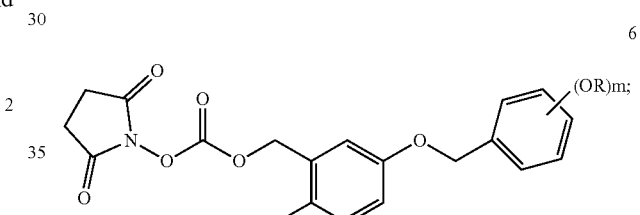

6

(iv) condensing ester (6) with diethyl (2-(2-(2-aminoethoxy) ethoxy) ethyl) phosphonate in presence of base to obtain diphosphonate ester (7)

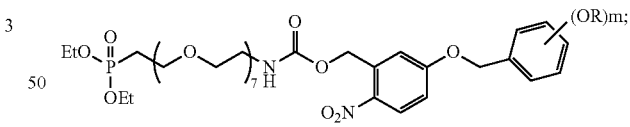

7 and (v) deprotecting diphosphonate ester (7) in presence of LiBr to mono phosphonate compound (8)

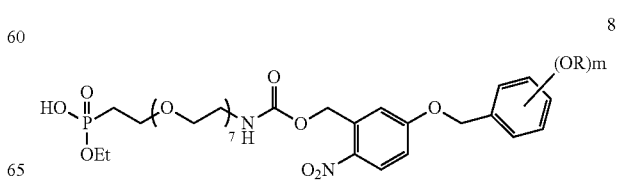

8 and fluorinating the mono phosphonate ester (8) with diethylaminosulfur trifluoride (DAST) to obtain photosensitive probe (9)

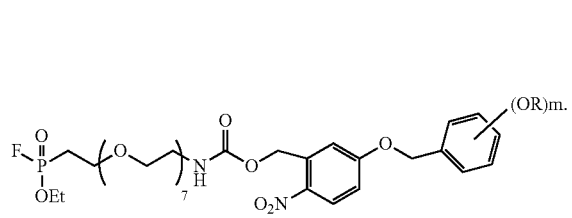

9

11. The process for preparing the pH sensitive probe ethyl (E)-(2-(2-((1-(2-(3,5-bis(dodecyloxy)benzylidene)hydrazine-1-carbonyl)-1H-1,2,3-triazol-4-yl) methoxy) ethoxy) ethyl) phosphonofluoridate (17') comprising;
(i) azidation of ethyl bromo acetate in 1:3 water-acetone mixture to yield ethyl 2-azidoacetate followed by reacting with alkyne terminated oligoethylene glycol spacer (12') using click chemistry to obtain triazole ester compound (13')

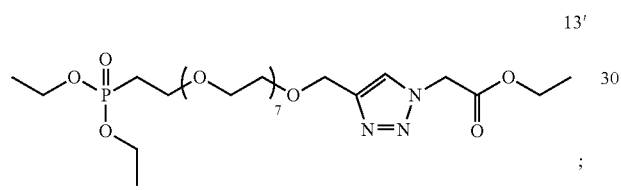

13'

(ii) reacting above ester (13') with hydrazine in absolute alcohol to obtain triazole phosphate compound (14)

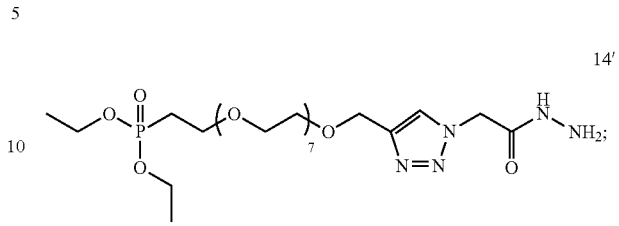

14'

(iii) reacting triazole phosphate compound (14) and substituted benzaldehyde

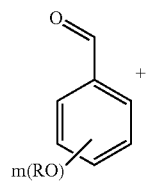

in alcohol followed by addition of acid to obtain imine (15);
(iv) deprotecting partially the imine (15)

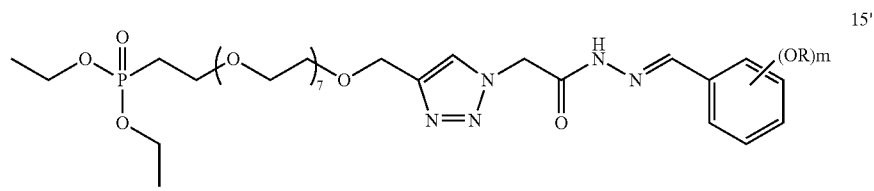

15' with sodium azide to obtain monophosphonate ester (16)

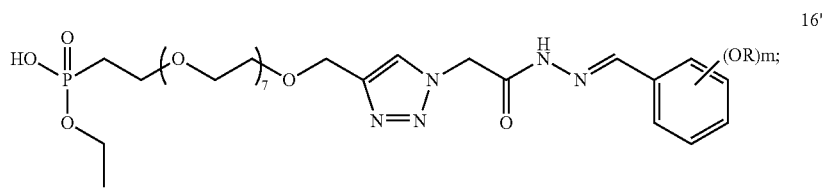

16' and (v) fluorinating the mono phosphonate ester (16) with diethylaminosulfur trifluoride (DAST) to obtain fluorinated mono phosphonate ester of pH sensitive probe (17)

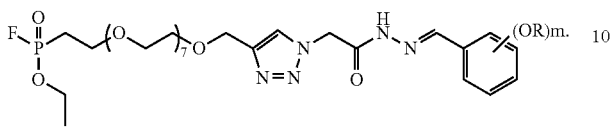

12. The process for preparing multi-stimuli sensitive probe of the formula

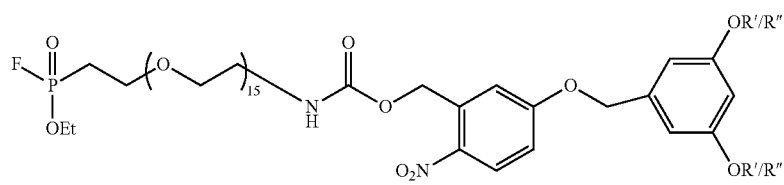

wherein R' is

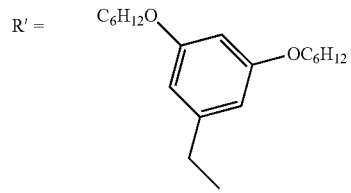

and R" is

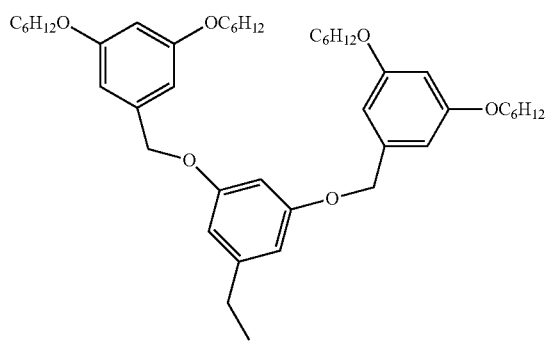

comprising;

(i) alkylation of

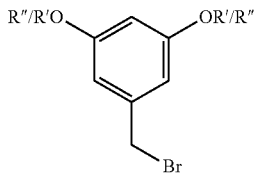

with 5-hydroxy-2-nitrobenzaldehyde in presence of base and solvent to obtain aldehyde

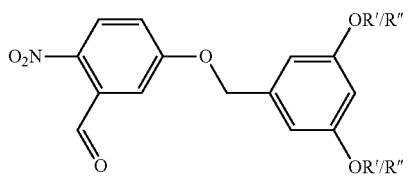

followed by reducing the aldehyde to an alcohol

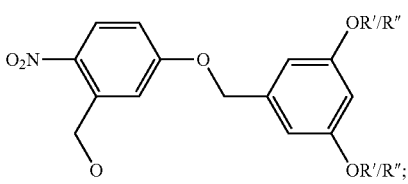

(ii) activating the alcohol of step (i) with N,N'-Disuccinimidyl carbonate in base and solvent to give activated ester

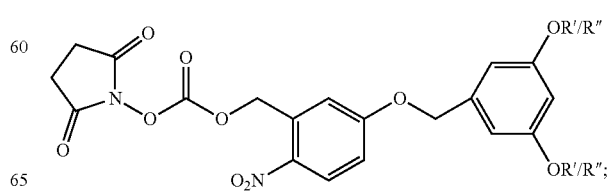

(iii) reacting the activated ester of step (ii) with the amine terminated cetyl oligoethylene spacer
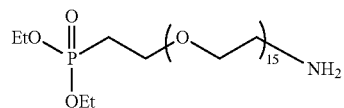
to give the diphosphonate ester
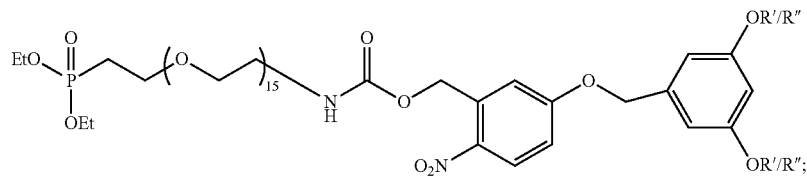
and
(iv) converting diphosphonate ester of step (iii) to monophosphonate
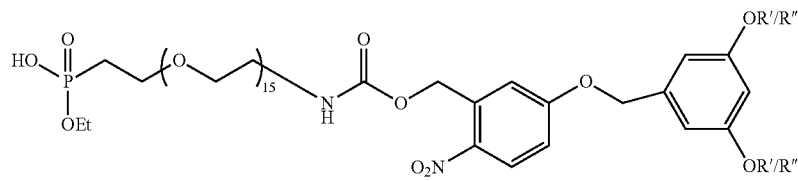
and fluorinating with diethylaminosulfur trifluoride (DAST) to yield fluorinated compound
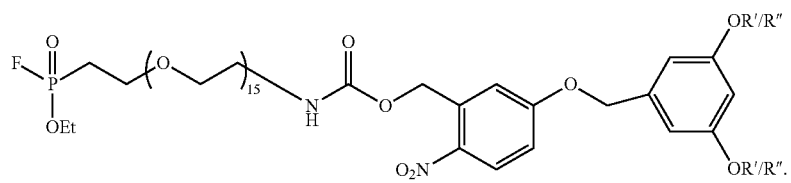
* * * * *